US009023984B2

(12) United States Patent
Hutton et al.

(10) Patent No.: US 9,023,984 B2
(45) Date of Patent: May 5, 2015

(54) DIAGNOSTIC AND THERAPEUTIC TARGET FOR AUTOIMMUNE DISEASES AND USES THEREOF

(75) Inventors: John C. Hutton, Denver, CO (US); Janet M. Wenzlau, Greenwood Village, CO (US); Jan Jensen, Shaker Heights, OH (US); Howard Davidson, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 1007 days.

(21) Appl. No.: 12/521,022

(22) PCT Filed: Dec. 28, 2007

(86) PCT No.: PCT/US2007/089125

§ 371 (c)(1), (2), (4) Date: Feb. 11, 2010

(87) PCT Pub. No.: WO2008/083331

PCT Pub. Date: Jul. 10, 2008

(65) Prior Publication Data

US 2010/0143374 A1 Jun. 10, 2010

Related U.S. Application Data

(60) Provisional application No. 60/882,815, filed on Dec. 29, 2006.

(51) Int. Cl.

| | |
|---|---|
| *C07K 14/00* | (2006.01) |
| *C07K 14/705* | (2006.01) |
| *C07K 14/47* | (2006.01) |
| *G01N 33/564* | (2006.01) |

(52) U.S. Cl.

CPC ............... *C07K 14/705* (2013.01); *C07K 14/47* (2013.01); *G01N 33/564* (2013.01); *G01N 2800/042* (2013.01); *G01N 2800/52* (2013.01)

(58) Field of Classification Search

None

See application file for complete search history.

(56) References Cited

U.S. PATENT DOCUMENTS

| | | | | |
|---|---|---|---|---|
| 5,820,866 | A | 10/1998 | Kappler et al. | |
| 7,851,164 | B2 * | 12/2010 | Seve et al. | 435/7.1 |
| 2006/0246442 | A1 | 11/2006 | Seve et al. | |

FOREIGN PATENT DOCUMENTS

| | | |
|---|---|---|
| CN | 1738900 | 2/2006 |
| EP | 0194276 | 9/1986 |
| EP | 0239400 | 9/1987 |
| EP | 0451216 | 10/1991 |
| EP | 0460617 | 12/1991 |
| WO | WO 86/01533 | 3/1986 |
| WO | WO 90/07861 | 7/1990 |
| WO | WO 01/94409 | 12/2001 |
| WO | WO 2004/046355 | 6/2004 |

OTHER PUBLICATIONS

English translation of Official Action for China Patent Application No. 200780051859.3, dated Jul. 19, 2011 3 pages.

Ablamunits et al., "The pathogenicity of islet-infiltrating lymphocytes in the non-obese diabetic (NOD) mouse," Clinical and Experimental Immunology, 1999, vol. 115, pp. 260-267.

Abraham et al., "Co-expression of HLA DR3 and DQ8 results in the development of spontaneous insulitis and loss of tolerance to GAD65 in transgenic mice," Diabetes, 2000, vol. 49, pp. 548-554.

Abraham et al., "Type 1 diabetes-predisposing MHC alleles influence the selection of glutamic acid decarboxylase (GAD) 65-specific T cells in a transgenic model," Journal of Immunology, Jan. 15, 2001, vol. 166, No. 2, pp. 1370-1379.

Altschul et al., "Gapped Blast and PSI-Blast: a new generation of protein database search programs," Nucleic Acids Research, 1997, vol. 25, pp. 3389-3402.

Amrani et al., "Perforin-independent beta-cell destruction by diabetogenic CD8( +) T lymphocytes in transgenicnonobese diabetic mice," The Journal of clinical investigation, 1999, vol. 103, pp. 1201-1209.

André et al. "Checkpoints in the progression of autoimmune disease: lessons from diabetes models," Proceedings of the National Academy of Sciences of the United States of America, 1996, vol. 93, pp. 2260-2263.

Arden et al., "Imogen 38: a novel 38-kD islet mitochondrial auto antigen recognized by T cells from a newly diagnosed type 1 diabetic patient," The Journal of clinical investigation, 1996, vol. 97, pp. 551-561.

Arif et al., "Autoreactive T cell responses show proinflammatory polarization in diabetes but a regulatory phenotype in health," The Journal of clinical investigation, 2004, vol. 113, pp. 451-463.

Atkinson et al., "Cellular immunity to a determinant common to glutamate decarboxylase and coxsackie virus in insulin-dependent diabete," The Journal of clinical investigation, 1994, vol. 94, pp. 2125-2129.

Baker et al. "Restricted islet-cell reactive T cell repertoire of early pancreatic islet infiltrates in NOD mice," Proceedings of the National Academy of Sciences of the United States of America, 2002, vol. 99, pp. 9374-9379.

Beste et al., "Small antibody-like proteins with prescribed ligand specificities derived from the lipocalin fold," Proc. Natl. Acad. Sci., Mar. 1999, vol. 96, pp. 1898-1903.

Cardozo et al., "A comprehensive analysis of cytokine-induced and nuclear factor-kappa B-dependent genes in primary rat pancreatic beta-cells," The Journal of biological chemistry, Dec. 28, 2001, vol. 276, No. 52 pp. 48879-48886.

(Continued)

*Primary Examiner* — Anand Desai

(74) *Attorney, Agent, or Firm* — Sheridan Ross P.C.

(57) ABSTRACT

Described is the identification of ZnT8 as an autoantigen target in type I autoimmune diabetes (T1D), other autoimmune disease, and other diabetes-linked diseases and conditions. Also described are a variety of therapeutic, diagnostic, and prognostic tools and methods based on this discovery. The identification of genetic variation in ZnT8 as an important player in the initiation of the disease process and the progression of autoimmunity to clinical diabetes is disclosed.

12 Claims, 36 Drawing Sheets

(56) References Cited

OTHER PUBLICATIONS

Chen et al., "Evidence that a peptide spanning the B-C junction of proinsulin is an early Autoantigen epitope in the pathogenesis of type 1 diabetes," Journal of Immunology, Nov. 1, 2001, vol. 167, No. 9, pp. 4926-4935.

Chimienti et al., "Identification and cloning of a beta-cell-specific zinc transporter, ZnT-8, localized into insulin secretory granules," Diabetes, Sep. 2004, vol. 53, No. 9, pp. 2330-2337.

Daniel et al. "Protection of nonobese diabetic mice from diabetes by intranasal or subcutaneous administration of insulin peptide B-(9-23)," Proceedings of the National Academy of Sciences of the United States of America, 1996, vol. 93, pp. 956-960.

DiLorenzo et al., "Major histocompatibility complex class I-restricted T cells are required for all but the end stages of diabetes development in nonobese diabetic mice and use a prevalent T cell receptor alpha chain gene rearrangement," Proceedings of the National Academy of Sciences of the U.S.A., 1998, vol. 95, pp. 12538-12543.

Gradwohl et al. "Neurogenin3 is required for the development of the four endocrine cell lineages of the pancreas," Proceedings of the National Academy of Sciences of the United States of America, 2000, vol. 97, pp. 1607-1611.

Graser et al., "Identification of a CD8 T cell that can independently mediate autoimmune diabetes development in the complete absence of CD4 T cell helper functions," Journal of Immunology, Apr. 1, 2000, vol. 164, No. 7, pp. 3913-3918.

Haskins et al., "Pancreatic islet-specific T-cell clones from nonobese diabetic mice," Proceedings of the National Academy of Sciences of the United States of America, 1989, vol. 86, pp. 8000-8004.

Herold, "Achieving antigen-specific immune regulation," The Journal of clinical investigation, Feb. 2004, vol. 113, No. 3, pp. 346-349.

Honeyman et al., "T-cell epitopes in type 1 diabetes autoantigen tyrosine phosphatase IA-2: potential for mimicry with rotavirus and other environmental agents," Molecular Medicine, Apr. 1998, vol. 4, No. 4, pp. 231-239.

Iizuka et al., "Deficiency of carbohydrate-activated transcription factor ChREBP prevents obesity and improves plasma glucose control in leptin-deficient (ob/ob) mice," American Journal of Physiology. Endocrinology and Metabolism, Aug. 2006, vol. 291, No. 2, pp. E358-E364.

Kassem et al., "Beta-cell proliferation and apoptosis in the developing normal human pancreas and in hyperinsulinism of infancy," Diabetes, Aug. 2000, vol. 49, No. 8, pp. 1325-1333.

Kawasaki et al., "Definition of multiple ICA512/phogrin autoantibody epitopes and detection of intramolecular epitope spreading in relatives of patients with type 1 diabetes," Diabetes, May 1998, vol. 47, No. 5, pp. 733-742.

Kelemen et al., "T-cell epitope analysis on the auto antigen phogrin (IA-2beta) in the nonobese diabetic mouse," Diabetes, Aug. 2001, vol. 50, No. 8, pp. 1729-1734.

Kohler et al., "Continuous cultures of fused cells secreting antibody of predefined specificity," Nature, Aug. 7, 1975, vol. 256, pp. 495-497.

Kukreja et al. "Multiple immuno-regulatory defects in type-I diabetes," The Journal of clinical investigation, Jan. 2002, vol. 109, No. 1, pp. 131-140.

Larger et al. "Pancreatic islet beta cells drive T cell-immune responses in the nonobese diabetic mouse model," The Journal of experimental medicine, May 1995, vol. 181, No. 5, pp. 1635-1642.

Lieberman et al., "Identification of the {beta} cell antigen targeted by a prevalent population of pathogenic CD8+ T cells in autoimmune diabetes," Proceedings of the National Academy of Sciences of the United States of America, 2003, vol. 100, pp. 8384-8388.

Lilla et al., "Differential gene expression in well-regulated and dysregulated pancreatic beta-cell (MIN6) sublines," Endocrinology, Apr. 2003, vol. 144, No. 4, pp. 1368-1379.

Meinkoth et al., "Hybridization of Nucleic Acids Immobilized on Solid Supports," Analytical Biochemistry, 1984, vol. 138, pp. 267-284.

Mukherjee et al., "Identification of CD4+ T cell-specific epitopes of islet-specific glueose-6-phosphatase catalytic subunit-related protein: a novel beta cell auto antigen in type 1 diabetes," The Journal of Immunology, May 2005, vol. 174, No. 9, pp. 5306-5315.

Mullins et al. "Identification of thyroid stimulating hormone receptor-specific T cells in Graves' disease thyroid using autoantigen-transfected Epstein-Barr virus-transformed B cell lines," The Journal of Clinical Investigation, Jul. 1995, vol. 9, No. 1, pp. 30-37.

Norris et al., "Timing of initial cereal exposure in infancy and risk of islet autoimmunity," JAMA : the journal of the American Medical Association, Oct. 1, 2003, vol. 290, No. 13, pp. 1713-1720.

Notkins et al., "Autoimmune type 1 diabetes: resolved and unresolved issues," The Journal of clinical investigation, Nov. 2001, vol. 108, No. 9, pp. 1247-1252.

Panagioitopoulos, et al, "Identification of a beta-cell-specific HLA class I restricted epitope in type 1 diabetes," Diabetes, Nov. 2003, vol. 52, No. 11, pp. 2647-2651.

Rossini, "Autoimmune diabetes and the circle of tolerance," Diabetes, Feb. 2004, vol. 53, No. 2, pp. 267-275.

Rudy et al., "Similar peptides from two beta cell autoantigens, proinsulin and glutamic acid decarboxylase, stimulate T cells of individuals at risk for insulin dependent diabetes," Molecular Medicine, Sep. 1995, vol. 1, No. 6, pp. 625-633.

Serreze et al., "B lymphocytes are critical antigen-presenting cells for the initiation of T cell-mediated autoimmune diabetes in nonobcsc diabetic mice," The Journal of Immunology, Oct. 15, 1998, vol. 161, No. 8, pp. 3912-3918.

Seve, et al., "In silico identification and expression of SLC30 family genes: an expressed sequence tag data mining strategy for the characterization of zinc transporters' tissue expression," BMC Genomics, May 23, 2004, vol. 5, No. 1, p. 32.

Staiger et al., "Polymorphisms within novel risk loci for type 2 diabetes determine beta-cell function.," PLoS One, Sep. 5, 2007, vol. 2, No. 9, E832, pp. 1-6.

Stribling et al., "Aerosol gene delivery in vivo," Proc. Natl. Acad. Sci. USA, Dec. 1992, vol. 189, pp. 11277-11281.

Takaki et al., "HLA-A*0201-restricted T cells from humanized NOD mice recognize autoantigens of potential clinical relevance to type 1 diabetes," Journal of Immunology, Mar. 1, 2006, vol. 176, No. 5, pp. 3257-3265.

Tatusova et al.,"Blast 2 sequences—a new tool for comparing protein and nucleotide sequences," FEMS Microbiology Letters, 1999, vol. 174, pp. 247-250.

Tian et al., "The frequency of high avidity T cells determines the hierarchy of determinant spreading," Journal of Immunology, Jun. 15, 2001, vol. 166, No. 12, pp. 7144-7150.

Trudeau et al., "Prediction of spontaneous autoimmune diabetes in NOD mice by quantification of autoreactive T cells in peripheral blood," The Journal of Clinical Investigation, Jan. 2003, vol. 111, No. 2, pp. 217-223.

Wenzlau et al., "The cation efflux transporter ZnT8 (S1c30A8) is a major autoantigen in human type 1 diabetes," Proceedings of the National Academy of Sciences of the U.S.A., Oct. 2007, vol. 104(43), pp. 17040-17045.

Wenzlau et al., "Identification of a major humoral epitope in S1c30A8 (ZnT8)," Annals of the New York Academy of Sciences, Dec. 2008, vol. 1150, pp. 252-255.

Wenzlau et al., "S1C30A8 is a major target of humoral autoimmunity in type 1 diabetes and a predictive marker in prediabetes," Annals of the New York Academy of Sciences, Dec. 2008, vol. 1150, pp. 256-259.

Wong et al., "CD8 T cell clones from young nonobese diabetic (NOD) islets can transfer rapid onset of diabetes in NOD mice in the absence of CD4 cells," The Journal of experimental medicine, Jan. 1, 1996, vol. 183(1), pp. 67-76.

Zekzer et al., "GAD-reactive CD4+ Th1 cells induce diabetes in NOD/SCID mice," The Journal of Clinical Investigation, Jan. 1, 1998, vol. 101(1), pp. 68-73.

Ziegler et al. "Early infant feeding and risk of developing type 1 diabetes-associated autoantibodies," JAMA : The journal of the American Medical Association, Oct. 1, 2003, vol. 290(13), pp. 1721-1728.

(56) References Cited

OTHER PUBLICATIONS

International Search Report for International (PCT) Application No. PCT/US2007/089125, mailed Aug. 8, 2008.
Written Opinion for International (PCT) Application No. PCT/US2007/089125, mailed Aug. 8, 2008.
International Preliminary Report on Patentability for International (PCT) Application No. PCT/US2007/089125, issued Jun. 30, 2009.
Supplementary European Search Report for European Patent Application No. 07870089.5, dated May 21, 2010.
English translation of Official Action for China Patent Application No. 200780051859.3, dated Mar. 29, 2012 5 pages.
Amrani et al., "Progression of autoimmune diabetes driven by avidity maturation of a T-cell population," Nature, 2000, vol. 406, pp. 739-742.
Atkinson et al., "The NOD mouse model of type 1 diabetes: as good as it gets?" Nat Med, 1999, vol. 5, pp. 601-604 (Abstract Only).
Backkcskov et al., "Identification of the 64K autoantigen in insulin-dependent diabetes as the GABA-synthesizing enzyme glutamic acid decarboxylase," Nature, 1990, vol. 347, pp. 151-156.
Baekkeskov et al., "Autoantibodies in newly diagnosed diabetic children immunoprecipitate human pancreatic islet cell proteins," Nature, 1982, vol. 298, pp. 167-169.
Bednarek et al., "Steroid 21-hydroxylase is a major autoantigen involved in adult onset autoimmune Addison's disease," FEBS Letters, 1992, vol. 309, pp. 51-55.
Benoist et al., "Autoimmunity provoked by infection: How good is the case for T cell epitope mimicry?" Nat Immunol, 2001, vol. 2, pp. 797-801.
Bonifacio et al., "Identification of protein tyrosine phosphatase-like IA2 (islet cell antigen 512) as the insulin-dependent diabetes-related 37/40K autoantigen and a target of islet-cell antibodies," Journal of Immunology, Dec. 1, 1995, vol. 155, No. 11, pp. 5419-5426.
Bowie et al., "Generation and maintenance of autoantigen-specific CD8(+) T cell clones isolated from NOD mice," Journal of Immunological Methods, 1999, vol. 228, pp. 87-95.
Buschard et al., "Sulphatide and sulphatide antibodies in insulin-dependent diabetes mellitus," The Lancet, 1993, vol. 342, No. 8875, p. 840.
Castano et al., "Identification and cloning of a granule auto antigen (carboxypeptidase-H) associated with type I diabetes," The Journal of clinical endocrinology and metabolism, Dec. 1991, vol. 73, No. 6 pp. 1197-1201.
Christianson et al., "Adoptive transfer of diabetes into immunodeficient NOD-scid/scid mice. Relative contributions of CD4+ and CD8+ T-cells from diabetic versus prediabetic NOD. NON-Thy-1a donors," Diabetes, Jan. 1993, vol. 42, No. 1, pp. 44-55.
Daniel et al., "Epitope specificity, cytokine production profile and diabetogenic activity of insulin-specific T cell clones isolated from NOD mice," European journal of Immunology, Apr. 1995, vol. 25, No. 4, pp. 1056-1062.
Eisenbarth et al., "Insulin autoimmunity: prediction/precipitation/prevention type 1A diabetes," Autoimmunity Reviews, May 2002, vol. 1, No. 3, pp. 139-145.
Gelber et al., "Isolation of nonobese diabetic mouse T-cells that recognize novel autoantigens involved in the early events of diabetes," Diabetes, Jan. 1994, vol. 43, No. 1, pp. 33-39.
Härkönen et al., "Enterovirus infection can induce immune responses that cross-react with beta-cell autoantigen tyrosine phosphatase IA-2/IAR," Journal of Medical Virology, Mar. 2002, vol. 66, No. 3, pp. 340-350.
Haskins et al., "Acceleration of diabetes in young NOD mice with a CD4+ islet-specific T cell clone," Science, 1990, vol. 249, pp. 1433-1436.
Inaba et al., "Double-step and inverse polymerase chain reaction for sensitive detection and cloning of T cell receptor variable regions sequences," International Immunology, Oct. 1991, vol. 3, No. 10, pp. 1053-1057.
Kallan et al., "Beta-cell reactive T-cell clones from type I diabetes patients are not beta cell specific and recognize multiple antigens," Journal of Autoimmunity, Dec. 1995, vol. 8, pp. 887-899 (pp. 887-889 provided).
Kash et al., "Glutamate decarboxylase and GABA in pancreatic islets: lessons from knock-out mice," Hormone and metabolic research = Hormon- und Stoffwechselforschung = Hormones et métabolisme, May 1999, vol. 31, No. 5, pp. 340-344.
Kaufman et al., "Spontaneous loss of T-cell tolerance to glutamic acid decarboxylase in murine insulin-dependent diabetes," Nature, 1993, vol. 366, pp. 69-72.
Kawasaki et al., "Autoantibodies to protein tyrosine phosphatase-like proteins in type I diabetes. Overlapping specificities to phogrin and ICA512/IA-2," Diabetes, Oct. 1996, vol. 45, No. 10, pp. 1344-1349.
Kelemen et al., "HLA-DQ8-associated T cell responses to the diabetes autoantigen phogrin (IA-2 beta) in human prediabetes," J Immunoll, 2004, vol. 172, pp. 3955-3962.
Malarkannan et al. "Generation of antigen-specific, lacZ—inducible T-cell hybrids," Methods in molecular biology, 2001, vol. 156, pp. 265-272.
Martin et al., "Islet cell auto antigen 69 antibodies in IDDM," Diabetologia, Jun. 1996, vol. 39, No. 6, p. 747.
Nagata et al., "Evidence for the role of CD8+ cytotoxic T cells in the destruction of pancreatic beta-cells in nonobese diabetic mice," The Journal of Immunology, Feb. 15, 1994, vol. 152, No. 4, pp. 2042-2050.
Nakayama et al., "Prime role for an insulin epitope in the development of type 1 diabetes in NOD mice," Nature, 2005, vol. 435, pp. 220-223.
Neophytou et al., "Development of a procedure for the direct cloning of T-cell epitopes using bacterial expression systems," Journal of immunological methods, Sep. 13, 1996, vol. 196, No. 1, pp. 63-72.
Petersen et al., "Neonatal tolerization with glutamic acid decarboxylase but not with bovine serum albumin delays the onset of diabetes in NOD mice," Diabetes, Dec. 1994, vol. 43, No. 12, pp. 1478-1484.
Ramiya, et al, "Effect of oral and intravenous insulin and glutamic acid decarboxylase in NOD mice," Autoimmunity, 1997, vol. 26, No. 3, pp. 139-151.
Redondo et al., "Heterogeneity of type I diabetes: analysis of monozygotic twins in Great Britain and the United States," Diabetologia, Mar. 2001, vol. 44, No. 3, pp. 354-362.
Roep et al., "Molecular mimicry in type 1 diabetes: immune cross-reactivity between islet autoantigen and human cytomegalovirus but not Coxsackie virus," Annals of the New York Academy of Sciences, Apr. 2002, vol. 958, pp. 163-165.
Roep et al., "T-cell clones from a type-1 diabetes patient respond to insulin secretory granule proteins," Nature, 1990, vol. 345, pp. 632-634.
Rosmalen et al., "Islet abnormalities in the pathogenesis of autoimmune diabetes," Trends in endocrinology and metabolism: TEM, Jul. 2002, vol. 13, No. 5, pp. 209-214.
Sladek et al., "A genome-wide association study identifies novel risk loci for type 2 diabetes," Nature, Feb. 2007, vol. 445, pp. 881-885.
Sonderstrup et al., "Identification of auto antigen epitopes in MHC class II transgenic mice," Immunological Reviews, Aug. 1998, vol. 164, pp. 129-138.
Taneja et al., "HLA class 11 transgenic mice as models of human diseases," Immunological Reviews, Jun. 1999, vol. 169, pp. 67-79.
Tian et al., "Modulating autoimmune responses to GAD inhibits disease progression and prolongs islet graft survival in diabetes-prone mice," Nat Med, 1996, vol. 2, pp. 1348-1353.
Tisch et al., "Immune response to glutamic acid decarboxylase correlates with insulitis in non-obese diabetic mice," Nature, 1993, vol. 366, pp. 72-75.
Van Vliet et al., "Human T cell clones with specificity for insulinoma cell antigens," European Journal of Immunology, Jan. 1989, vol. 19, No. 1, pp. 213-216.
Wang et al. "The role of CD8+ T cells in the initiation of insulin-dependent diabetes mellitus," European Journal of Immunology, Aug. 1996, vol. 26, No. 8, pp. 1762-1769.

(56) References Cited

OTHER PUBLICATIONS

Wegmann et al., "Establishment of islet-specific T-cell lines and clones from islet isografts placed in spontaneously diabetic NOD mice," Journal of Autoimmunity, Oct. 1993, vol. 6, No. 5, pp. 517-527.
Wegmann et al., "Insulin-specific T cells are a predominant component of islet infiltrates in pre-diabetic NOD mice," European Journal of Immunology, Aug. 1994, vol. 24, No. 8, pp. 1852-1857.
Wolfe et al., "Endogenous expression levels of autoantigens influence success or failure of DNA immunizations to prevent type 1 diabetes: addition of IL-4 increases safety," European Journal of Immunology, Jan. 2002, vol. 32, No. 1, pp. 113-121.
Wong et al., "Identification of an MHC class I-restricted auto antigen in type 1 diabetes by screening an organ-specific cDNA library," Nat Med. 1999, vol. 5, pp. 1026-1031.
Yang et al., "Monoclonal T cells identified in early NOD islet infiltrates," Immunity, Feb. 1996, vol. 4, No. 2, pp. 189-194.
English translation of Final Official Action for China Patent Application No. 200780051859.3, dated Oct. 10, 2012 5 pages.
Official Action for European Patent Application No. 07870089.5, dated Oct. 15, 2012, 4 pages.
Official Action for Japanese Patent Application No. 2009-544308, mailed Apr. 2, 2013, 8 pages (includes English translation).
Achenbach et al., "Stratification of Type 1 Diabetes Risk on the Basis of Islet Autoantibody Characteristics," Diabetes, 2004, vol. 53, No. 2, pp. 384-392.
Chimienti et al., "In vivo expression and functional characterization of the zinc transporter ZnT8 in glucose-induced insulin secretion," Journal of Cell Science, 2006, vol. 119, Iss, 20, pp. 4199-4206.
Chimienti et al., "ZnT-8, A Pancreatic Beta-Cell-Specific Zinc Transporter," Biometals, 2005, vol. 18, Iss. 4, pp. 313-317.
Månsson et al., "Islet Cell Antibodies Represent Autoimmune Response Against Several Antigens," International Journal of Experimental Diabetes Research, 2001, vol. 2, Iss. 2, pp. 85-90.
Notice of Intention to Grant for European Patent Application No. 07870089.5, dated Apr. 25, 2014, 7 pages.
Official Action for Japanese Patent Application No. 2009-544308, mailed Apr. 8, 2014, 8 pages (includes English translation).
Official Action for Indian Patent Application No. 4827/DELNP/2009 dated Mar. 27, 2014, 2 pages.

* cited by examiner

Ref: NP_776250.2

Alternative splicing at 5'end

| EST | Tissue | 5'UTR | Ex1 | Ex2 | Ex3 | Ex4 | Start |
|---|---|---|---|---|---|---|---|
| Hs#S1607587 | unknown | 201 | | | | | MYHCH |
| Hs#S28540510 | kidney | 391 | | | | | MEFLER |
| Hs#S4285174 | unknown | 229 | | | | | MYHCH |
| Hs#S4429920 | insulinoma | 251 | | | | | MEFLER |
| Hs#S4432322 | insulinoma | 261 | | | | | MEFLER |
| Hs#S4551898 | HR85 islet | 230 | | | | | MYHCH |
| Hs#S4717409 | insulinoma | 311 | | | | | MEFLER |
| Hs#S5973587 | insulinoma | 267 | | | | | MYHCH |
| Hs#S5975844 | HR85 islet | 230 | | | | | MEFLER |
| Hs#S7104928 | HR85 islet | 230 | | | | | MEFLER |
| Hs#S11062701 | unknown | 230 | | | | | MEFLER |
| HS#S4077144 | insulinoma | 261 | | | | | MEFLER |
| HS#S4077148 | insulinoma | 261 | | | | | MEFLER |
| HS#S4005605 | insulinoma | 261 | | | | | MEFLER |

FIG. 11

| Antibody Status | INS/GAD/IA2 | ZnT8 INS/GAD/IA2 | ZnT8C GAD/IA2 |
|---|---|---|---|
| 5Ab | - | 16 | - |
| >4Ab | - | 34 | - |
| >3Ab | 44 | 64 | 42 |
| >2Ab | 72 | 78 | 72 |
| >1Ab | 86 | 92 | 92 |
| 0Ab | 14 | 8 | 8 |

| Antibody Status | ZnT8ORF | ZnT8C | IA2 | GAD65 | INS | Total |
|---|---|---|---|---|---|---|
| 5Ab | 8 | 8 | 8 | 8 | 8 | 8 |
| 4Ab | 0 | 9 | 9 | 9 | 9 | 9 |
| 3Ab | 2 | 9 | 12 | 12 | 10 | 15 |
| 2Ab | 0 | 2 | 4 | 6 | 2 | 7 |
| 1Ab | 1 | 3 | 1 | 3 | 0 | 8 |
| 0Ab | n/a | n/a | n/a | n/a | n/a | 3 |
| ICA+ only | 0 | 2 | 0 | 0 | 0 | 8 |

FIG. 15A
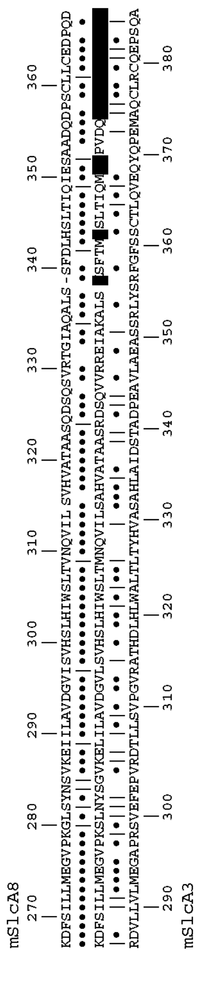
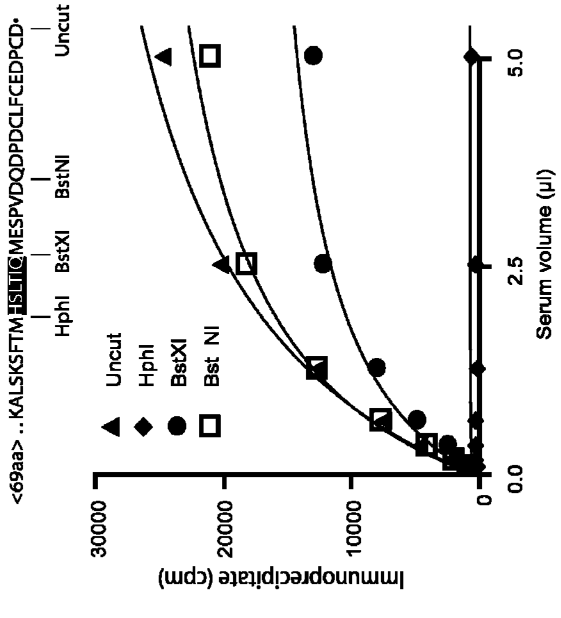
FIG. 15B
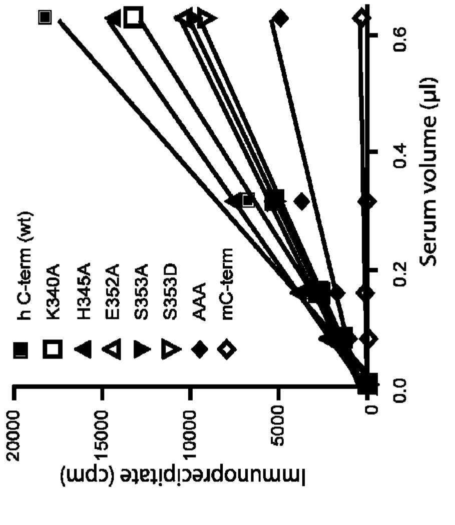
FIG. 15C

Slc30A8

| | | | |
|---|---|---|---|
| Human | VY | | Positions 342-358 of SEQ ID NO:2 |
| Monkey | VY | | SEQ ID NO:26 |
| Dog | Y V | A | SEQ ID NO:27 |
| Rat | DL I | AA | SEQ ID NO:28 |
| Mouse | DL I | AA | Positions 340-356 SEQ ID NO:4 |
| Cow | PV | SCSPTRI | SEQ ID NO:29 |
| Toad | PF V | PIE S | SEQ ID NO:30 |
| Chick | YSF I | GG E | SEQ ID NO:31 |
| Fish | YSF V | L PQA R | SEQ ID NO:32 |

Other CzcD

| | | | |
|---|---|---|---|
| hSlc30A2 | HF TV | I DYSEDM | SEQ ID NO:33 |
| hSlc30A3 | GFSSC L V | QYQPEM | SEQ ID NO:34 |
| Pyrococcus | GITHV | L TGRCKE | SEQ ID NO:35 |

Unrelated

| | | | |
|---|---|---|---|
| E.coli | VDGNQI | KI VQ | SEQ ID NO:36 |
| hREEP3 | SMHDLT | GDE G R | SEQ ID NO:37 |

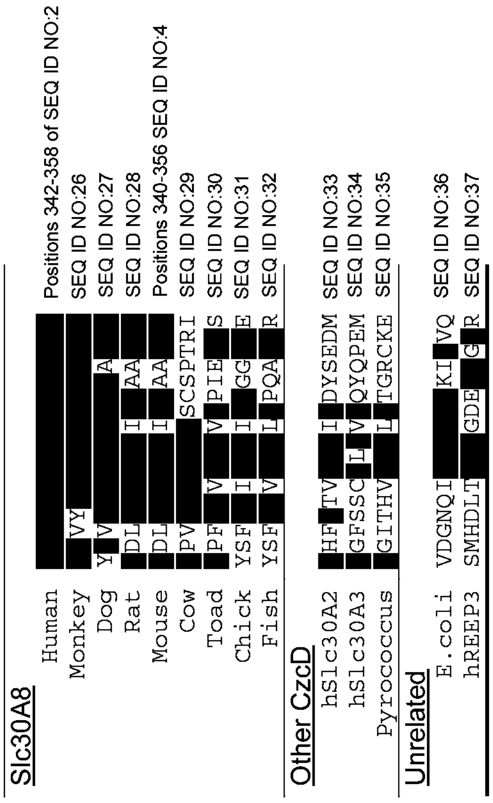

```
N-term
          10        20        30        40        50        60         70
  □   □ |□□□|□|□|□□□||         □  |□|| □   □  || || | □□□□|  □ | | |      □□ |□□
Mse MEFLERTYLVNDQATKMYAFPLDR  -ELRQKPVNKDQCPGDRP --EHPEAGGIYHCHNSAKAT -GNRSSKQAHAKWRLC
Hum MEFLERTYLVNDKAAKMYAFTLESVELQQKPVNKDQCPRERP   --EELESGGMYHCHSGSKPT -EKGANEYAYAKWKLC
Xen MKGSEEAYLVSDKATKMYSLT  -------- KDSEKNH -PSKPPLQDEENPQSKYHCHNNNKKAYDARQREQTFAKKKLC

Alternate Start (Hum)                           #


C-term
     270       280       290       300       310       320       330       340        350       360
      |         |         |         |         |         |         |         |          |         |
  |□|  |□□□□ □||| □| □□| □□  □□□□□ □□□□□□|□|□□|□□□□□□ □|□□   |□| |  |||| |   □  □□|□□□|□|  □□ □ □||□ |□ |
Mse KDFSILLMEGVPKGLSYNSVKEIILAVDGVISVHSLHIWSLTVNQVILSVHVATAASQDSQSVRTGIAQALS     -SFDLHSLTIQIESAADQDPSCLLCEDPQD*
Hum KDFSILLMEGVPK [redacted]DPDCLFCEDPCD*
Xen RDLLTVLMEGTPRGIHYSDVKQSILAVDGVKSVHSLHLWALTMNQVILSAHIATDIVGESKRILKDVTQNVFARFPFHSVTIQVEPIEDQSPECMFCYEPTQ*

Zn binding His                   #  #           #                         #
SNP Rs13266634 C>T                                      TAAS   WDS
```

FIG. 20

| | Slc30A1 | Slc30 A2 | Slc30A3 | Slc30A4 | Slc30A5 | Slc30A6 | Slc30A7 | Slc30A8 | Slc30A9 | Slc30A10 |
|---|---|---|---|---|---|---|---|---|---|---|
| Slc30A1 (507 aa) | | 29% (64%) | 23% (81%) | 26% (60%) | 27% (63%) | 26% (33%) | 21% (82%) | 25% (68%) | NS | 36% (96%) |
| Slc30A2 (372 aa) | 29% (74%) | | 55% (86%) | 40% (82%) | 23% (76%) | 21% (78%) | 21% (72%) | 52% (88%) | NS | 27% (46%) |
| Slc30A3 (388 aa) | 28% (62%) | 55% (86%) | | 39% (80%) | 21% (77%) | 24% (70%) | 22% (77%) | 42% (97%) | NS | 23% (65%) |
| Slc30A4 (429 aa) | 28% (67%) | 42% (75%) | 39% (73%) | | 26% (68%) | 21% (57%) | 24% (72%) | 41% (73%) | 24% (17%) | 25% (74%) |
| Slc30A5 (765 aa) | 29% (35%) | 24% (41%) | 23% (41%) | 27% (40%) | | 25% (42%) | 41% (42%) | 23% (39%) | NS | 33% (34%) |
| Slc30A6 (461 aa) | 27% (16%) | 21% (70%) | 24% (60%) | 20% (54%) | 24% (67%) | | 26% (61%) | 21% (53%) | NS | 21% (18%) |
| Slc30A7 (376 aa) | 25% (71%) | 21% (85%) | 22% (90%) | 22% (92%) | 52% (39%) | 22% (96%) | | 21% (80%) | NS | 27% (91%) |
| Slc30A8 (369 aa) | 26% (81%) | 52% (88%) | 42% (88%) | 41% (80%) | 22% (73%) | 23% (69%) | 20% (66%) | | NS | 28% (76%) |
| Slc30A9 (568 aa) | NS | NS | NS | 24% (13%) | 23% (25%) | NS | NS | NS | | NS |
| Slc30A10 (485 aa) | 36% (94%) | 27% (65%) | 23% (68%) | 29% (58%) | 34% (56%) | 21% (17%) | 26% (78%) | 28% (60%) | NS | |

FIG. 22A
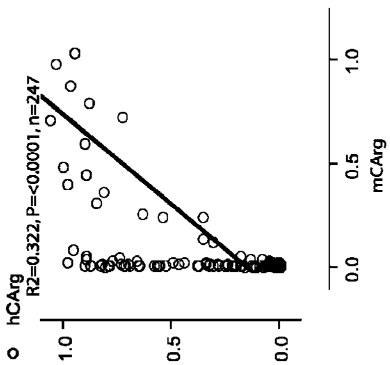
FIG. 22B
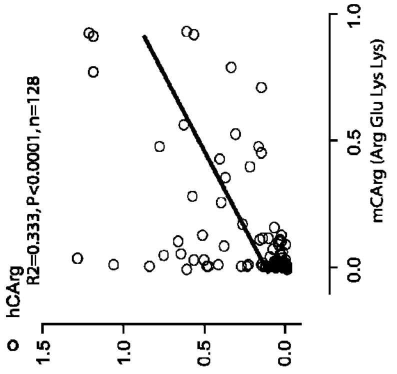
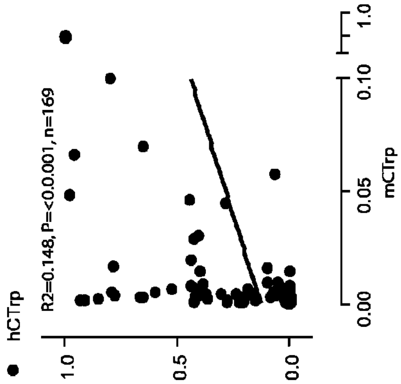
FIG. 22C
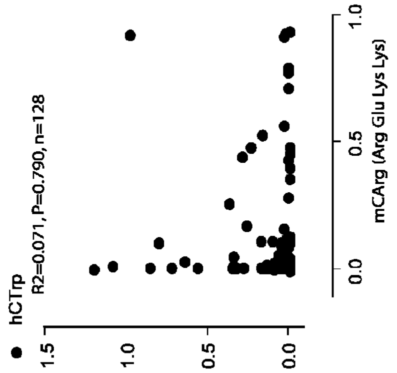
FIG. 22D

FIG. 25

| Reactivity to probes | Genotype | | | | | | | |
|---|---|---|---|---|---|---|---|---|
| | Any (300) | | CC (169) | | CT (108) | | TT (23) | |
| | n | % | n | % | n | % | n | % |
| Any | 198 | 66.0 | 116 | 68.6 | 63 | 58.4 | 19 | 82.6 |
| All | 96 | 32.0 | 58 | 34.3 | 33 | 30.6 | 5 | 21.7 |
| Gln | 113 | 37.7 | 69 | 40.8 | 38 | 35.2 | 6 | 26.1 |
| Arg | 179 | 59.7 | 115 | 68.0 | 57 | 52.8 | 7 | 30.4 |
| Trp | 138 | 46.0 | 64 | 37.9 | 55 | 50.9 | 19 | 82.6 |
| Gln only | 1* | 0.3 | 1 | 0.6 | 0 | 0.0 | 0 | 0.0 |
| Arg only | 47 | 15.7 | 41 | 24.3 | 6 | 5.6 | 0 | 0.0 |
| Trp only | 15 | 5.0 | 0 | 0.0 | 4 | 3.7 | 11 | 47.8 |
| Arg and Trp (Gln<0.02) | 13 | 4.3 | 2* | 1.2 | 11 | 10.2 | 0 | 0.0 |
| Arg>Gln | 55 | 18.3 | 50 | 29.6 | 5 | 4.6 | 0 | 0.0 |
| Trp>Gln | 17 | 5.7 | 1 | 0.6 | 12 | 11.1 | 4 | 17.4 |
| Arg>Gln & Trp>Gln | 3 | 1.0 | 1 | 0.6 | 2 | 1.9 | 0 | 0.0 |

Fisher Exact test: *Index <0.05; Row 1 P=0.046; TT vs CT 0.029; Row 2 P=0.441; Row 3 P=0.314; Row 4 P=0.0005; Row 5 P=0.0001; Row 6 P=0.678; Row 7 P=<0.0001; Row 8 P=<0.0001; Row 9 P=0.0009; Row 10 P<0.0001; Row 11 P<0.0001; Row 12 P=0.519

Parallel (9/19 cases)
C-term
N/C
C-pep
GADA
IA-2A
Days post onset

ZnTA slower (7/19 cases)

ZnTA faster (2/19 cases)

| | C-term | | N/C fusion | | C-peptide |
|---|---|---|---|---|---|
| | Onset | Follow-up | Onset | Follow-up | Follow-up |
| Prevalence % (n=60) | 69.5 | 27.1 | 49.2 | 17.0 | 27.1 |
| Ab Level % of initial | | 11.0± 15.3 (39) | | 12.9±14.5 (29) | |
| Antibody t1/2 (we eks) | | 60.2±39.3 (42) | | 60.8±49.5 (16) | |

SEQUENCE LISTING

```
<160> NUMBER OF SEQ ID NOS: 67

<210> SEQ ID NO 1
<211> LENGTH: 5373
<212> TYPE: DNA
<213> ORGANISM: Homo sapiens
<220> FEATURE:
<221> NAME/KEY: CDS
<222> LOCATION: (231)..(1340)

<400> SEQUENCE: 1

agcagttttt gtaggtgaaa acaatgaagc caggtaatat tgcaaggagg ctgtaatttt      60

agcagaccta ccaacaacac tgatgtagga agctcattat tttaatttct ggagcctttt     120

aatttttct ttagaaagtg tataaataat tgcagtgctg ctttgcttcc aaaactgggc     180

agtgagttca acaacaacga caacaacagc cgcagctcat cctggccgtc atg gag       236
                                                       Met Glu
                                                       1

ttt ctt gaa aga acg tat ctt gtg aat gat aaa gct gcc aag atg tat      284
Phe Leu Glu Arg Thr Tyr Leu Val Asn Asp Lys Ala Ala Lys Met Tyr
        5                   10                  15

gct ttc aca cta gaa agt gtg gaa ctc caa cag aaa ccg gtg aat aaa      332
Ala Phe Thr Leu Glu Ser Val Glu Leu Gln Gln Lys Pro Val Asn Lys
    20                  25                  30

gat cag tgt ccc aga gag aga cca gag gag ctg gag tca gga ggc atg      380
Asp Gln Cys Pro Arg Glu Arg Pro Glu Glu Leu Glu Ser Gly Gly Met
35                  40                  45                  50

tac cac tgc cac agt ggc tcc aag ccc aca gaa aag ggg gcg aat gag      428
Tyr His Cys His Ser Gly Ser Lys Pro Thr Glu Lys Gly Ala Asn Glu
                55                  60                  65

tac gcc tat gcc aag tgg aaa ctc tgt tct gct tca gca ata tgc ttc      476
Tyr Ala Tyr Ala Lys Trp Lys Leu Cys Ser Ala Ser Ala Ile Cys Phe
            70                  75                  80

att ttc atg att gca gag gtc gtg ggt ggg cac att gct ggg agt ctt      524
Ile Phe Met Ile Ala Glu Val Val Gly Gly His Ile Ala Gly Ser Leu
        85                  90                  95

gct gtt gtc aca gat gct gcc cac ctc tta att gac ctg acc agt ttc      572
Ala Val Val Thr Asp Ala Ala His Leu Leu Ile Asp Leu Thr Ser Phe
    100                 105                 110

ctg ctc agt ctc ttc tcc ctg tgg ttg tca tcg aag cct ccc tct aag      620
Leu Leu Ser Leu Phe Ser Leu Trp Leu Ser Ser Lys Pro Pro Ser Lys
115                 120                 125                 130

cgg ctg aca ttt gga tgg cac cga gca gag atc ctt ggt gcc ctg ctc      668
Arg Leu Thr Phe Gly Trp His Arg Ala Glu Ile Leu Gly Ala Leu Leu
                135                 140                 145

tcc atc ctg tgc atc tgg gtg gtg act ggc gtg cta gtg tac ctg gca      716
Ser Ile Leu Cys Ile Trp Val Val Thr Gly Val Leu Val Tyr Leu Ala
            150                 155                 160

tgt gag cgc ctg ctg tat cct gat tac cag atc cag gcg act gtg atg      764
```

-continued

```
Cys Glu Arg Leu Leu Tyr Pro Asp Tyr Gln Ile Gln Ala Thr Val Met
        165                 170                 175

atc atc gtt tcc agc tgc gca gtg gcg gcc aac att gta cta act gtg      812
Ile Ile Val Ser Ser Cys Ala Val Ala Ala Asn Ile Val Leu Thr Val
    180                 185                 190

gtt ttg cac cag aga tgc ctt ggc cac aat cac aag gaa gta caa gcc      860
Val Leu His Gln Arg Cys Leu Gly His Asn His Lys Glu Val Gln Ala
195                 200                 205                 210

aat gcc agc gtc aga gct gct ttt gtg cat gcc ctt gga gat cta ttt      908
Asn Ala Ser Val Arg Ala Ala Phe Val His Ala Leu Gly Asp Leu Phe
                215                 220                 225

cag agt atc agt gtg cta att agt gca ctt att atc tac ttt aag cca      956
Gln Ser Ile Ser Val Leu Ile Ser Ala Leu Ile Ile Tyr Phe Lys Pro
            230                 235                 240

gag tat aaa ata gcc gac cca atc tgc aca ttc atc ttt tcc atc ctg     1004
Glu Tyr Lys Ile Ala Asp Pro Ile Cys Thr Phe Ile Phe Ser Ile Leu
        245                 250                 255

gtc ttg gcc agc acc atc act atc tta aag gac ttc tcc atc tta ctc     1052
Val Leu Ala Ser Thr Ile Thr Ile Leu Lys Asp Phe Ser Ile Leu Leu
    260                 265                 270

atg gaa ggt gtg cca aag agc ctg aat tac agt ggt gtg aaa gag ctt     1100
Met Glu Gly Val Pro Lys Ser Leu Asn Tyr Ser Gly Val Lys Glu Leu
275                 280                 285                 290

att tta gca gtc gac ggg gtg ctg tct gtg cac agc ctg cac atc tgg     1148
Ile Leu Ala Val Asp Gly Val Leu Ser Val His Ser Leu His Ile Trp
                295                 300                 305

tct cta aca atg aat caa gta att ctc tca gct cat gtt gct aca gca     1196
Ser Leu Thr Met Asn Gln Val Ile Leu Ser Ala His Val Ala Thr Ala
            310                 315                 320

gcc agc cgg gac agc caa gtg gtt cgg aga gaa att gct aaa gcc ctt     1244
Ala Ser Arg Asp Ser Gln Val Val Arg Arg Glu Ile Ala Lys Ala Leu
        325                 330                 335

agc aaa agc ttt acg atg cac tca ctc acc att cag atg gaa tct cca     1292
Ser Lys Ser Phe Thr Met His Ser Leu Thr Ile Gln Met Glu Ser Pro
    340                 345                 350

gtt gac cag gac ccc gac tgc ctt ttc tgt gaa gac ccc tgt gac tag     1340
Val Asp Gln Asp Pro Asp Cys Leu Phe Cys Glu Asp Pro Cys Asp
355                 360                 365

ctcagtcaca ccgtcagttt cccaaatttg acaggccacc ttcaaacatg ctgctatgca   1400

gtttctgcat catagaaaat aaggaaccaa aggaagaaat tcatgtcatg gtgcaatgca   1460

cattttatct atttatttag ttccattcac catgaaggaa gaggcactga gatccatcaa   1520

tcaattggat tatatactga tcagtagctg tgttcaattg caggaatgtg tatatagatt   1580

attcctgagt ggagccgaag taacagctgt ttgtaactat cggcaatacc aaattcatct   1640

cccttccaat aatgcatctt gagaacacat aggtaaattt gaactcagga aagtcttact   1700

agaaatcagt ggaagggaca aatagtcaca aaattttacc aaaacattag aaacaaaaaa   1760

taaggagagc caagtcagga ataaaagtga ctctgtatgc taacgccaca ttagaacttg   1820

gttctctcac caagctgtaa tgtgattttt ttttctactc tgaattggaa atatgtatga   1880

atatacagag aagtgcttac aactaatttt tatttacttg tcacattttg gcaataaatc   1940

cctcttattt ctaaattcta acttgtttat ttcaaaactt tatataatca ctgttcaaaa   2000

ggaaatattt tcacctacca gagtgcttaa acactggcac cagccaaaga atgtggttgt   2060

agagacccag aagtcttcaa gaacagccga caaaaacatt cgagttgacc ccaccaagtt   2120

gttgccacag ataatttaga tatttacctg caagaaggaa taaagcagat gcaaccaatt   2180
```

-continued cattcagtcc acgagcatga tgtgagcact gctttgtgct agacattggg cttagcattg 2240
aaactataaa gaggaatcag acgcagcaag tgcttctgtg ttctggtagc aactcaacac 2300
tatctgtgga gagtaaactg aagatgtgca ggccaacatt ctggaaatcc tatgtcaatg 2360
ggtttggttt ggaacctgga cttctgcatt tttaaaagtt acccagagat gcttctaaag 2420
atgagccata gtctagaaga ttgtcaacca caggagttca ttgagtggga cagctagaca 2480
catacattgg cagctacaat agtatcatga attgcaatga tgtagtgggg tataaaagga 2540
aagcgatgga tattgccgga tgggcatggc cagtgatgtt tcacgtcatt gaggtgacag 2600
ctctgctgga ctttgaatta catatggagg ctctccagga agacgaagaa gagaaggaca 2660
ttctaggcaa aaagaagact aggcacaagg cacacttatg tttgtctgtt agcttttagt 2720
tgaaaaagca aaatacatga tgcaaagaaa cctctccacg ctgtgatttt taaaactaca 2780
tactttttgc aactttatgg ttatgagtat tgtagagaac aggagatagg tcttagatga 2840
tttttatgtt gttgtcagac tctagcaagg tactagaaac ctagcaggca ttaataattg 2900
ttgaggcaat gactctgagg ctatatctgg gccttgtcat tatttatcat ttatatttgt 2960
atttttttct gaaatttgag ggccaagaaa acattgactt tgactgagga ggtcacatct 3020
gtgccatctc tgcaaatcaa tcagcaccac tgaaataact acttagcatt ctgctgagct 3080
ttccctgctc agtagagaca aatatactca tccccccacct cagtgagctt gtttaggcaa 3140
ccaggattag agctgctcag gttcccaacg tctcctgcca catcgggttc tcaaaatgga 3200
aagaatggtt tatgccaaat cacttttcct gtctgaagga ccactgaatg gttttgtttt 3260
tccatatttt gcataggacg ccctaaagac taggtgactt ggcaaacaca caagtgttag 3320
tataattctt tgcttctgct tctttttgaa aatcatgttt agatttgatt ttaagtcaga 3380
aattcactga atgtcaggta atcattatgg agggagattt gtgtgtcaac caaagtaatt 3440
gtcccatggc cccagggtat ttctgttgtt tccctgaaat tctgcttttt tagtcagcta 3500
gattgaaaac tctgaacagt agatgtttat atggcaaaat gcaagacaat ctacaaggga 3560
gattttaagg attttgagat gaaaaaacag atgctactca ggggctttat gaaccatcca 3620
tcaattctga agttctgact ctcccattac cctttccctg gtgtggtcag aactccaggt 3680
cactggaagt tagtggaatc atgtagttga attctttact tcaagacatt gtattctctc 3740
cagctatcaa aacattaatg atcttttatg tctttttttt gttattgtta tactttaagt 3800
tctggggtac atgtgcggaa catgtaggtt tgttacatag gtatacatgt gccatggtgg 3860
tttgctgcac tcatcaacct gtcatctaca ttcttttatg tctgtctttc aaagcaacac 3920
tctgttcttc tgagtagtga aatcaggtca actttaccac cagcctccat ttttaatatg 3980
cttcaccatc atccagcacc tacttaagat ttatctaggg ctctgtggtg atgttaggac 4040
ccataaaaga aatttatgcc ttccatatgt ttggttacag atgggaaatg ggaatgttga 4100
aggacatgaa agaaaggatg tttacacatt aagcatcagt tctgaagcta gattgtctga 4160
gtttgaatct tagctcttcc ctttattagc tctgtgacct cgagctagtt acttaaatgc 4220
tctgatcctc tatttcctga tcagtgaaac ctccctattc aaatgtgtga gagtttaata 4280
aattaggaca cttaaaaatg ttggagcagt gcatagcatg tagtgttcag tacatgttaa 4340
atgttgtttt ttattatgta caaacatgag tgggcacaga attttaaatc atctcaactt 4400
ttgagaaatt ttgagttatc aacaccgttc ccacaagaca gtggcaaaat tattggtgag 4460
aattaaacag ctgtttctca gaggaagcaa tggaggcttg ctgggataaa ggcatttact 4520
gagaggctgt tacctagtga gagtgatgaa ttaattaaaa tagtcgaatc cctttctgac 4580

```
tgtctctgaa agcttccgct tttatctttg aagagcagaa ttgtcactcc aaggacattt   4640

attaataaaa agaacaactg tccagtgcaa tgaaggcaaa gtcataggtc tcccaagtct   4700

taccccattc ctgtgaaata tcaagttctt ggcttttctc tgtcatgtag cctcaacttt   4760

ctctgaccgg gtgcatttct ttctctggtt tctaaattgc cagtggcaaa tttggatcac   4820

ttacttaata tctgttaaat tttgtgaccc aacaaagtct tttagcactg tggtgtcaaa   4880

aagaaaaaca cctcccaggc atatacattt tatagattcc tggagaatgt tgctctccag   4940

ctccatcccc acccaatgaa atatgatcca gagagtcttg caaagagaca agcctcattt   5000

tccacaatta gctctaaagt gcctccagga aatgattttc tcagctcatc tctctgtatt   5060

ccctgttttg gatcacaggg caatctgttt aaatgactaa ttacagaaat cattaaaggc   5120

accaagcaaa tgtcatctct gaatacacac atcccaagct ttacaaatcc tgcctggctt   5180

gacagtgatg aggccactta acagtccagc gcaggcggat gttaaaaaaa ataaaaaggt   5240

gaccatctgc ggtttagttt tttaactttc tgatttcaca cttaacgtct gtcattctgt   5300

tactgggcac ctgtttaaat tctattttaa aatgttaatg tgtgttgttt aaaataaaat   5360

caagaaagag aga                                                      5373
```

<210> SEQ ID NO 2
<211> LENGTH: 369
<212> TYPE: PRT
<213> ORGANISM: Homo sapiens

<400> SEQUENCE: 2

```
Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Ala Ser Ala Ile
65                  70                  75                  80

Cys Phe Ile Phe Met Ile Ala Glu Val Val Gly Gly His Ile Ala Gly
                85                  90                  95

Ser Leu Ala Val Val Thr Asp Ala Ala His Leu Leu Ile Asp Leu Thr
            100                 105                 110

Ser Phe Leu Leu Ser Leu Phe Ser Leu Trp Leu Ser Ser Lys Pro Pro
        115                 120                 125

Ser Lys Arg Leu Thr Phe Gly Trp His Arg Ala Glu Ile Leu Gly Ala
    130                 135                 140

Leu Leu Ser Ile Leu Cys Ile Trp Val Val Thr Gly Val Leu Val Tyr
145                 150                 155                 160

Leu Ala Cys Glu Arg Leu Leu Tyr Pro Asp Tyr Gln Ile Gln Ala Thr
                165                 170                 175

Val Met Ile Ile Val Ser Ser Cys Ala Val Ala Ala Asn Ile Val Leu
            180                 185                 190

Thr Val Val Leu His Gln Arg Cys Leu Gly His Asn His Lys Glu Val
        195                 200                 205

Gln Ala Asn Ala Ser Val Arg Ala Ala Phe Val His Ala Leu Gly Asp
    210                 215                 220
```

```
Leu Phe Gln Ser Ile Ser Val Leu Ile Ser Ala Leu Ile Ile Tyr Phe
225                 230                 235                 240

Lys Pro Glu Tyr Lys Ile Ala Asp Pro Ile Cys Thr Phe Ile Phe Ser
                245                 250                 255

Ile Leu Val Leu Ala Ser Thr Ile Thr Ile Leu Lys Asp Phe Ser Ile
            260                 265                 270

Leu Leu Met Glu Gly Val Pro Lys Ser Leu Asn Tyr Ser Gly Val Lys
        275                 280                 285

Glu Leu Ile Leu Ala Val Asp Gly Val Leu Ser Val His Ser Leu His
    290                 295                 300

Ile Trp Ser Leu Thr Met Asn Gln Val Ile Leu Ser Ala His Val Ala
305                 310                 315                 320

Thr Ala Ala Ser Arg Asp Ser Gln Val Val Arg Arg Glu Ile Ala Lys
                325                 330                 335

Ala Leu Ser Lys Ser Phe Thr Met His Ser Leu Thr Ile Gln Met Glu
            340                 345                 350

Ser Pro Val Asp Gln Asp Pro Asp Cys Leu Phe Cys Glu Asp Pro Cys
        355                 360                 365

Asp


<210> SEQ ID NO 3
<211> LENGTH: 1906
<212> TYPE: DNA
<213> ORGANISM: Mus musculus
<220> FEATURE:
<221> NAME/KEY: CDS
<222> LOCATION: (334)..(1437)

<400> SEQUENCE: 3

atgtgcgcgc acgcgcgcgc gcacacacac acacacacac acacacacac acacacacac      60

acacttatta caattgtacc tttgagtctc ccagaaaagc agtttctgtg agtgatagaa     120

tgagtctagg tgattttcca aggagactgt taattttcac agatttaccc acaacactga     180

tataggaggc ctcattaact caagtactgg aagaattttt ctaatttctt aggaagttgt     240

gtgaatataa taatatcagt gcttctttac ttccaaaact ggacagcgca tcaaacatca     300

gaaacaacag tatcagctcc tgtcccaact acc atg gag ttt ctt gag aga act      354
                                     Met Glu Phe Leu Glu Arg Thr
                                     1               5

tat ctt gtg aat gat caa gcc acc aag atg tac gcc ttc cct cta gac      402
Tyr Leu Val Asn Asp Gln Ala Thr Lys Met Tyr Ala Phe Pro Leu Asp
        10                  15                  20

aga gaa ctt cga cag aag cct gtg aat aaa gat cag tgt cct gga gac      450
Arg Glu Leu Arg Gln Lys Pro Val Asn Lys Asp Gln Cys Pro Gly Asp
    25                  30                  35

agg cca gag cat cca gag gca gga ggc atc tat cac tgc cac aac agc      498
Arg Pro Glu His Pro Glu Ala Gly Gly Ile Tyr His Cys His Asn Ser
40                  45                  50                  55

gcc aag gcc aca ggg aac agg tcg agc aag caa gcg cat gcc aag tgg      546
Ala Lys Ala Thr Gly Asn Arg Ser Ser Lys Gln Ala His Ala Lys Trp
                60                  65                  70

aga ctc tgt gct gct tca gca ata tgc ttc atc ttt atg gtg gca gag      594
Arg Leu Cys Ala Ala Ser Ala Ile Cys Phe Ile Phe Met Val Ala Glu
            75                  80                  85

gtg gtg ggt gga cac gtt gct ggg agt ctg gct atc ctc act gat gcg      642
Val Val Gly Gly His Val Ala Gly Ser Leu Ala Ile Leu Thr Asp Ala
        90                  95                  100

gct cat ctc tta att gac ctg act agt ttc ctg ctc agt ctc ttt tct      690
```

-continued

```
Ala His Leu Leu Ile Asp Leu Thr Ser Phe Leu Leu Ser Leu Phe Ser
    105                 110                 115

ttg tgg ttg tca tcg agg ccc cct tcc aag cgg ctg aca ttt ggg tgg      738
Leu Trp Leu Ser Ser Arg Pro Pro Ser Lys Arg Leu Thr Phe Gly Trp
120                 125                 130                 135

tat cga gca gag atc ctc ggt gcc ctg ctg tct gtc ctt tgc atc tgg      786
Tyr Arg Ala Glu Ile Leu Gly Ala Leu Leu Ser Val Leu Cys Ile Trp
                140                 145                 150

gtg gtg act ggt gtg ctg ctg tac ctt gcc tgt gag cgc ctt ttg tat      834
Val Val Thr Gly Val Leu Leu Tyr Leu Ala Cys Glu Arg Leu Leu Tyr
            155                 160                 165

cct gat tac cag atc caa gca ggt atc atg atc act gtt tca ggc tgt      882
Pro Asp Tyr Gln Ile Gln Ala Gly Ile Met Ile Thr Val Ser Gly Cys
        170                 175                 180

gca gtg gca gcc aac att gta cta act atg att ttg cac caa cgg aac      930
Ala Val Ala Ala Asn Ile Val Leu Thr Met Ile Leu His Gln Arg Asn
    185                 190                 195

ttt ggc tac aac cac aag gat gta caa gct aat gcc agt gtc cga gca      978
Phe Gly Tyr Asn His Lys Asp Val Gln Ala Asn Ala Ser Val Arg Ala
200                 205                 210                 215

gcc ttt gtg cat gcc ctg ggg gat gta ttt cag agc atc agt gtg cta     1026
Ala Phe Val His Ala Leu Gly Asp Val Phe Gln Ser Ile Ser Val Leu
                220                 225                 230

att agt gct ctc att atc tac ttt aag cct gac tac aaa att gct gat     1074
Ile Ser Ala Leu Ile Ile Tyr Phe Lys Pro Asp Tyr Lys Ile Ala Asp
            235                 240                 245

cca gtg tgc aca ttt atc ttt tcc atc ctg gtt ttg gcc agc acc gtc     1122
Pro Val Cys Thr Phe Ile Phe Ser Ile Leu Val Leu Ala Ser Thr Val
        250                 255                 260

atg atc tta aaa gac ttc tcc atc tta ctc atg gaa ggt gtt cca aag     1170
Met Ile Leu Lys Asp Phe Ser Ile Leu Leu Met Glu Gly Val Pro Lys
    265                 270                 275

ggc ctg agt tac aac agt gtg aaa gag atc atc ctc gca gtt gat ggc     1218
Gly Leu Ser Tyr Asn Ser Val Lys Glu Ile Ile Leu Ala Val Asp Gly
280                 285                 290                 295

gtg atc tcc gtg cac agt cta cac atc tgg tca ctg act gtg aac caa     1266
Val Ile Ser Val His Ser Leu His Ile Trp Ser Leu Thr Val Asn Gln
                300                 305                 310

gtg att ctc tct gtt cat gtt gct aca gct gcc agc cag gac agc cag     1314
Val Ile Leu Ser Val His Val Ala Thr Ala Ala Ser Gln Asp Ser Gln
            315                 320                 325

tct gtg cgg aca gga att gct caa gcc ctc agc agc ttt gat ctt cac     1362
Ser Val Arg Thr Gly Ile Ala Gln Ala Leu Ser Ser Phe Asp Leu His
        330                 335                 340

tct ctt acc att cag ata gaa tct gca gca gac cag gac ccc agc tgc     1410
Ser Leu Thr Ile Gln Ile Glu Ser Ala Ala Asp Gln Asp Pro Ser Cys
    345                 350                 355

ctt ctc tgc gaa gac cct cag gac tag ctcggtcaca ctgtcagctt           1457
Leu Leu Cys Glu Asp Pro Gln Asp
360                 365

cctgtgtttc ctaggccatg ataagatgca gcaaagtttc tgcaatgcac aatgaggcag   1517

ccgtcggaat agatttgaga aagtcatgat gatgcaatgt gcacactctt cctttgtatt   1577

tatctctatc caccatgaac gaggatgcat gggatttgtc ggcttcttgg attatacact   1637

aatcagtagt tgtgctcaat tgtagtatat atagattatt cctaactgga gctgaaataa   1697

cagatgtttg caatcatagg taatgaatga ttcacttgcc tacaatagtg ggtatagttt   1757

tactcggaaa tgcctttcta ggaatccaca gcatgagaaa caaacatttg aagagaattt   1817
```

-continued

```
gaggccttag aatttgattc tgccaccata ctcaatgaga tctttatttt ttgtgaaaca   1877

gtaaaacttc cctcttttga ccttgcatg                                      1906


<210> SEQ ID NO 4
<211> LENGTH: 367
<212> TYPE: PRT
<213> ORGANISM: Mus musculus

<400> SEQUENCE: 4

Met Glu Phe Leu Glu Arg Thr Tyr Leu Val Asn Asp Gln Ala Thr Lys
1               5                   10                  15

Met Tyr Ala Phe Pro Leu Asp Arg Glu Leu Arg Gln Lys Pro Val Asn
            20                  25                  30

Lys Asp Gln Cys Pro Gly Asp Arg Pro Glu His Pro Glu Ala Gly Gly
        35                  40                  45

Ile Tyr His Cys His Asn Ser Ala Lys Ala Thr Gly Asn Arg Ser Ser
    50                  55                  60

Lys Gln Ala His Ala Lys Trp Arg Leu Cys Ala Ala Ser Ala Ile Cys
65                  70                  75                  80

Phe Ile Phe Met Val Ala Glu Val Val Gly Gly His Val Ala Gly Ser
                85                  90                  95

Leu Ala Ile Leu Thr Asp Ala Ala His Leu Leu Ile Asp Leu Thr Ser
            100                 105                 110

Phe Leu Leu Ser Leu Phe Ser Leu Trp Leu Ser Ser Arg Pro Pro Ser
        115                 120                 125

Lys Arg Leu Thr Phe Gly Trp Tyr Arg Ala Glu Ile Leu Gly Ala Leu
    130                 135                 140

Leu Ser Val Leu Cys Ile Trp Val Val Thr Gly Val Leu Leu Tyr Leu
145                 150                 155                 160

Ala Cys Glu Arg Leu Leu Tyr Pro Asp Tyr Gln Ile Gln Ala Gly Ile
                165                 170                 175

Met Ile Thr Val Ser Gly Cys Ala Val Ala Ala Asn Ile Val Leu Thr
            180                 185                 190

Met Ile Leu His Gln Arg Asn Phe Gly Tyr Asn His Lys Asp Val Gln
        195                 200                 205

Ala Asn Ala Ser Val Arg Ala Ala Phe Val His Ala Leu Gly Asp Val
    210                 215                 220

Phe Gln Ser Ile Ser Val Leu Ile Ser Ala Leu Ile Ile Tyr Phe Lys
225                 230                 235                 240

Pro Asp Tyr Lys Ile Ala Asp Pro Val Cys Thr Phe Ile Phe Ser Ile
                245                 250                 255

Leu Val Leu Ala Ser Thr Val Met Ile Leu Lys Asp Phe Ser Ile Leu
            260                 265                 270

Leu Met Glu Gly Val Pro Lys Gly Leu Ser Tyr Asn Ser Val Lys Glu
        275                 280                 285

Ile Ile Leu Ala Val Asp Gly Val Ile Ser Val His Ser Leu His Ile
    290                 295                 300

Trp Ser Leu Thr Val Asn Gln Val Ile Leu Ser Val His Val Ala Thr
305                 310                 315                 320

Ala Ala Ser Gln Asp Ser Gln Ser Val Arg Thr Gly Ile Ala Gln Ala
                325                 330                 335

Leu Ser Ser Phe Asp Leu His Ser Leu Thr Ile Gln Ile Glu Ser Ala
            340                 345                 350

Ala Asp Gln Asp Pro Ser Cys Leu Leu Cys Glu Asp Pro Gln Asp
```

355 360 365

<210> SEQ ID NO 5
<211> LENGTH: 320
<212> TYPE: PRT
<213> ORGANISM: Homo sapiens

<400> SEQUENCE: 5

Met Tyr His Cys His Ser Gly Ser Lys Pro Thr Glu Lys Gly Ala Asn
1 5 10 15

Glu Tyr Ala Tyr Ala Lys Trp Lys Leu Cys Ser Ala Ser Ala Ile Cys
20 25 30

Phe Ile Phe Met Ile Ala Glu Val Val Gly Gly His Ile Ala Gly Ser
35 40 45

Leu Ala Val Val Thr Asp Ala Ala His Leu Leu Ile Asp Leu Thr Ser
50 55 60

Phe Leu Leu Ser Leu Phe Ser Leu Trp Leu Ser Ser Lys Pro Pro Ser
65 70 75 80

Lys Arg Leu Thr Phe Gly Trp His Arg Ala Glu Ile Leu Gly Ala Leu
85 90 95

Leu Ser Ile Leu Cys Ile Trp Val Val Thr Gly Val Leu Val Tyr Leu
100 105 110

Ala Cys Glu Arg Leu Leu Tyr Pro Asp Tyr Gln Ile Gln Ala Thr Val
115 120 125

Met Ile Ile Val Ser Ser Cys Ala Val Ala Ala Asn Ile Val Leu Thr
130 135 140

Val Val Leu His Gln Arg Cys Leu Gly His Asn His Lys Glu Val Gln
145 150 155 160

Ala Asn Ala Ser Val Arg Ala Ala Phe Val His Ala Leu Gly Asp Leu
165 170 175

Phe Gln Ser Ile Ser Val Leu Ile Ser Ala Leu Ile Ile Tyr Phe Lys
180 185 190

Pro Glu Tyr Lys Ile Ala Asp Pro Ile Cys Thr Phe Ile Phe Ser Ile
195 200 205

Leu Val Leu Ala Ser Thr Ile Thr Ile Leu Lys Asp Phe Ser Ile Leu
210 215 220

Leu Met Glu Gly Val Pro Lys Ser Leu Asn Tyr Ser Gly Val Lys Glu
225 230 235 240

Leu Ile Leu Ala Val Asp Gly Val Leu Ser Val His Ser Leu His Ile
245 250 255

Trp Ser Leu Thr Met Asn Gln Val Ile Leu Ser Ala His Val Ala Thr
260 265 270

Ala Ala Ser Arg Asp Ser Gln Val Val Arg Arg Glu Ile Ala Lys Ala
275 280 285

Leu Ser Lys Ser Phe Thr Met His Ser Leu Thr Ile Gln Met Glu Ser
290 295 300

Pro Val Asp Gln Asp Pro Asp Cys Leu Phe Cys Glu Asp Pro Cys Asp
305 310 315 320

<210> SEQ ID NO 6
<211> LENGTH: 28
<212> TYPE: PRT
<213> ORGANISM: Homo sapiens

<400> SEQUENCE: 6

Met Glu Phe Leu Glu Arg Ala Tyr Leu Val Asn Asp Lys Ala Ala Lys

-continued

```
1               5                   10                  15

Met Tyr Ala Phe Thr Leu Glu Arg Arg Ser Cys Lys
            20                  25


<210> SEQ ID NO 7
<211> LENGTH: 28
<212> TYPE: PRT
<213> ORGANISM: Homo sapiens

<400> SEQUENCE: 7

Met Glu Phe Leu Glu Arg Thr Tyr Leu Val Asn Asp Lys Ala Ala Lys
1               5                   10                  15

Met Tyr Ala Phe Thr Leu Glu Arg Arg Ser Arg Lys
            20                  25


<210> SEQ ID NO 8
<211> LENGTH: 74
<212> TYPE: PRT
<213> ORGANISM: Homo sapiens

<400> SEQUENCE: 8

Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu
65                  70


<210> SEQ ID NO 9
<211> LENGTH: 103
<212> TYPE: PRT
<213> ORGANISM: Homo sapiens

<400> SEQUENCE: 9

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp
            100


<210> SEQ ID NO 10
<211> LENGTH: 87
<212> TYPE: PRT
<213> ORGANISM: Homo sapiens

<400> SEQUENCE: 10
```

-continued

```
Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser
                85


<210> SEQ ID NO 11
<211> LENGTH: 78
<212> TYPE: PRT
<213> ORGANISM: Homo sapiens

<400> SEQUENCE: 11

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Lys Ser Phe Thr Met
65                  70                  75


<210> SEQ ID NO 12
<211> LENGTH: 103
<212> TYPE: PRT
<213> ORGANISM: Homo sapiens

<400> SEQUENCE: 12

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Ala Ser Phe Thr Met Ala Ser
65                  70                  75                  80

Leu Thr Ile Gln Met Ala Ala Pro Val Asp Gln Asp Pro Asp Cys Leu
                85                  90                  95

Phe Cys Glu Asp Pro Cys Asp
            100


<210> SEQ ID NO 13
<211> LENGTH: 26
<212> TYPE: PRT
<213> ORGANISM: Homo sapiens

<400> SEQUENCE: 13

Val Leu Thr Val Val Leu His Gln Arg Cys Leu Gly His Asn His Lys
```

```
1               5                   10                  15

Glu Val Gln Ala Asn Ala Ser Val Arg Ala
            20                  25


<210> SEQ ID NO 14
<211> LENGTH: 95
<212> TYPE: PRT
<213> ORGANISM: Homo sapiens

<400> SEQUENCE: 14

Met Glu Gly Val Pro Lys Ser Leu Asn Tyr Ser Gly Val Lys Glu Leu
1               5                   10                  15

Ile Leu Ala Val Asp Gly Val Leu Ser Val His Ser Leu His Ile Trp
            20                  25                  30

Ser Leu Thr Met Asn Gln Val Ile Leu Ser Ala His Val Ala Thr Ala
        35                  40                  45

Ala Ser Arg Asp Ser Gln Val Val Arg Arg Glu Ile Ala Lys Ala Leu
    50                  55                  60

Ser Lys Ser Phe Thr Met His Ser Leu Thr Ile Gln Met Glu Ser Pro
65                  70                  75                  80

Val Asp Gln Asp Pro Asp Cys Leu Phe Cys Glu Asp Pro Cys Asp
                85                  90                  95


<210> SEQ ID NO 15
<211> LENGTH: 88
<212> TYPE: PRT
<213> ORGANISM: Homo sapiens

<400> SEQUENCE: 15

Met Asn Tyr Ser Gly Val Lys Glu Leu Ile Leu Ala Val Asp Gly Val
1               5                   10                  15

Leu Ser Val His Ser Leu His Ile Trp Ser Leu Thr Met Asn Gln Val
            20                  25                  30

Ile Leu Ser Ala His Val Ala Thr Ala Ala Ser Arg Asp Ser Gln Val
        35                  40                  45

Val Arg Arg Glu Ile Ala Lys Ala Leu Ser Lys Ser Phe Thr Met His
    50                  55                  60

Ser Leu Thr Ile Gln Met Glu Ser Pro Val Asp Gln Asp Pro Asp Cys
65                  70                  75                  80

Leu Phe Cys Glu Asp Pro Cys Asp
                85


<210> SEQ ID NO 16
<211> LENGTH: 80
<212> TYPE: PRT
<213> ORGANISM: Homo sapiens

<400> SEQUENCE: 16

Met Ile Leu Ala Val Asp Gly Val Leu Ser Val His Ser Leu His Ile
1               5                   10                  15

Trp Ser Leu Thr Met Asn Gln Val Ile Leu Ser Ala His Val Ala Thr
            20                  25                  30

Ala Ala Ser Arg Asp Ser Gln Val Val Arg Arg Glu Ile Ala Lys Ala
        35                  40                  45

Leu Ser Lys Ser Phe Thr Met His Ser Leu Thr Ile Gln Met Glu Ser
    50                  55                  60

Pro Val Asp Gln Asp Pro Asp Cys Leu Phe Cys Glu Asp Pro Cys Asp
65                  70                  75                  80
```

<210> SEQ ID NO 17
<211> LENGTH: 70
<212> TYPE: PRT
<213> ORGANISM: Homo sapiens

<400> SEQUENCE: 17

```
Met His Ser Leu His Ile Trp Ser Leu Thr Met Asn Gln Val Ile Leu
1               5                   10                  15

Ser Ala His Val Ala Thr Ala Ala Ser Arg Asp Ser Gln Val Val Arg
            20                  25                  30

Arg Glu Ile Ala Lys Ala Leu Ser Lys Ser Phe Thr Met His Ser Leu
        35                  40                  45

Thr Ile Gln Met Glu Ser Pro Val Asp Gln Asp Pro Asp Cys Leu Phe
    50                  55                  60

Cys Glu Asp Pro Cys Asp
65                  70
```

<210> SEQ ID NO 18
<211> LENGTH: 65
<212> TYPE: PRT
<213> ORGANISM: Homo sapiens

<400> SEQUENCE: 18

```
Met Trp Ser Leu Thr Met Asn Gln Val Ile Leu Ser Ala His Val Ala
1               5                   10                  15

Thr Ala Ala Ser Arg Asp Ser Gln Val Val Arg Arg Glu Ile Ala Lys
            20                  25                  30

Ala Leu Ser Lys Ser Phe Thr Met His Ser Leu Thr Ile Gln Met Glu
        35                  40                  45

Ser Pro Val Asp Gln Asp Pro Asp Cys Leu Phe Cys Glu Asp Pro Cys
    50                  55                  60

Asp
65
```

<210> SEQ ID NO 19
<211> LENGTH: 26
<212> TYPE: PRT
<213> ORGANISM: Homo sapiens

<400> SEQUENCE: 19

```
Met Asp Phe Ser Ile Leu Leu Met Glu Gly Val Pro Lys Ser Leu Asn
1               5                   10                  15

Tyr Ser Gly Val Lys Glu Leu Ile Leu Ala
            20                  25
```

<210> SEQ ID NO 20
<211> LENGTH: 57
<212> TYPE: PRT
<213> ORGANISM: Homo sapiens

<400> SEQUENCE: 20

```
Met Asp Phe Ser Ile Leu Leu Met Glu Gly Val Pro Lys Ser Leu Asn
1               5                   10                  15

Tyr Ser Gly Val Lys Glu Leu Ile Leu Ala Val Asp Gly Val Leu Ser
            20                  25                  30

Val His Ser Leu His Ile Trp Ser Leu Thr Met Asn Gln Val Ile Leu
        35                  40                  45

Ser Ala His Val Ala Thr Ala Ala Ser
```

50 55

<210> SEQ ID NO 21
<211> LENGTH: 76
<212> TYPE: PRT
<213> ORGANISM: Homo sapiens

<400> SEQUENCE: 21

Met Asp Phe Ser Ile Leu Leu Met Glu Gly Val Pro Lys Ser Leu Asn
1 5 10 15

Tyr Ser Gly Val Lys Glu Leu Ile Leu Ala Val Asp Gly Val Leu Ser
20 25 30

Val His Ser Leu His Ile Trp Ser Leu Thr Met Asn Gln Val Ile Leu
35 40 45

Ser Ala His Val Ala Thr Ala Ala Ser Arg Asp Ser Gln Val Val Arg
50 55 60

Arg Glu Ile Ala Lys Ala Leu Ser Lys Ser Phe Thr
65 70 75

<210> SEQ ID NO 22
<211> LENGTH: 102
<212> TYPE: PRT
<213> ORGANISM: Homo sapiens

<400> SEQUENCE: 22

Met Asp Phe Ser Ile Leu Leu Met Glu Gly Val Pro Lys Ser Leu Asn
1 5 10 15

Tyr Ser Gly Val Lys Glu Leu Ile Leu Ala Val Asp Gly Val Leu Ser
20 25 30

Val His Ser Leu His Ile Trp Ser Leu Thr Met Asn Gln Val Ile Leu
35 40 45

Ser Ala His Val Ala Thr Ala Ala Ser Arg Asp Ser Gln Val Val Arg
50 55 60

Arg Glu Ile Ala Lys Ala Leu Ser Lys Ser Phe Thr Met His Ser Leu
65 70 75 80

Thr Ile Gln Met Glu Ser Pro Val Asp Gln Asp Pro Asp Cys Leu Phe
85 90 95

Cys Glu Asp Pro Cys Asp
100

<210> SEQ ID NO 23
<211> LENGTH: 89
<212> TYPE: PRT
<213> ORGANISM: Homo sapiens

<400> SEQUENCE: 23

Met Asp Phe Ser Ile Leu Leu Met Glu Gly Val Pro Lys Ser Leu Asn
1 5 10 15

Tyr Ser Gly Val Lys Glu Leu Ile Leu Ala Val Asp Gly Val Leu Ser
20 25 30

Val His Ser Leu His Ile Trp Ser Leu Thr Met Asn Gln Val Ile Leu
35 40 45

Ser Ala His Val Ala Thr Ala Ala Ser Arg Asp Ser Gln Val Val Arg
50 55 60

Arg Glu Ile Ala Lys Ala Leu Ser Lys Ser Phe Thr Met His Ser Leu
65 70 75 80

Thr Ile Gln Met Glu Ser Pro Val Asp
85

<210> SEQ ID NO 24
<211> LENGTH: 102
<212> TYPE: PRT
<213> ORGANISM: Homo sapiens

<400> SEQUENCE: 24

```
Met Asp Phe Ser Ile Leu Leu Met Glu Gly Val Pro Lys Ser Leu Asn
1               5                   10                  15

Tyr Ser Gly Val Lys Glu Leu Ile Leu Ala Val Asp Gly Val Leu Ser
            20                  25                  30

Val His Ser Leu His Ile Trp Ser Leu Thr Met Asn Gln Val Ile Leu
        35                  40                  45

Ser Ala His Val Ala Thr Ala Ala Ser Arg Asp Ser Gln Val Val Arg
    50                  55                  60

Arg Glu Ile Ala Lys Ala Leu Ser Lys Ser Phe Thr Met His Ser Leu
65                  70                  75                  80

Thr Ile Gln Met Glu Ser Pro Val Asp Gln Asp Pro Asp Cys Leu Phe
                85                  90                  95

Cys Glu Asp Pro Cys Asp
            100
```

<210> SEQ ID NO 25
<211> LENGTH: 103
<212> TYPE: PRT
<213> ORGANISM: Mus musculus

<400> SEQUENCE: 25

```
Arg Asp Val Leu Leu Val Leu Met Glu Gly Ala Pro Arg Ser Val Glu
1               5                   10                  15

Phe Glu Pro Val Arg Asp Thr Leu Leu Ser Val Pro Gly Val Arg Ala
            20                  25                  30

Thr His Asp Leu His Leu Trp Ala Leu Thr Leu Thr Tyr His Val Ala
        35                  40                  45

Ser Ala His Leu Ala Ile Asp Ser Thr Ala Asp Pro Glu Ala Val Leu
    50                  55                  60

Ala Glu Ala Ser Ser Arg Leu Tyr Ser Arg Phe Gly Phe Ser Ser Cys
65                  70                  75                  80

Thr Leu Gln Val Glu Gln Tyr Gln Pro Glu Met Ala Gln Cys Leu Arg
                85                  90                  95

Cys Gln Glu Pro Ser Gln Ala
            100
```

<210> SEQ ID NO 26
<211> LENGTH: 17
<212> TYPE: PRT
<213> ORGANISM: Macaca mulatta

<400> SEQUENCE: 26

```
Phe Thr Val Tyr Ser Leu Thr Ile Gln Met Glu Ser Pro Val Asp Gln
1               5                   10                  15

Asp
```

<210> SEQ ID NO 27
<211> LENGTH: 17
<212> TYPE: PRT
<213> ORGANISM: Canis familiaris

<400> SEQUENCE: 27

Tyr Thr Val His Ser Leu Thr Ile Gln Met Glu Ser Pro Ala Asp Gln
1 5 10 15

Asp

<210> SEQ ID NO 28
<211> LENGTH: 17
<212> TYPE: PRT
<213> ORGANISM: Rattus rattus

<400> SEQUENCE: 28

Phe Asp Leu His Ser Leu Thr Ile Gln Ile Glu Ser Ala Ala Asp Gln
1 5 10 15

Asp

<210> SEQ ID NO 29
<211> LENGTH: 17
<212> TYPE: PRT
<213> ORGANISM: Bos taurus

<400> SEQUENCE: 29

Phe Pro Val His Ser Leu Thr Ile Gln Met Ser Cys Ser Pro Thr Arg
1 5 10 15

Ile

<210> SEQ ID NO 30
<211> LENGTH: 17
<212> TYPE: PRT
<213> ORGANISM: Xenopus sp.

<400> SEQUENCE: 30

Phe Pro Phe His Ser Val Thr Ile Gln Val Glu Pro Ile Glu Asp Gln
1 5 10 15

Ser

<210> SEQ ID NO 31
<211> LENGTH: 17
<212> TYPE: PRT
<213> ORGANISM: Gallus gallus

<400> SEQUENCE: 31

Tyr Ser Phe His Ser Ile Thr Ile Gln Ile Glu Ser Gly Gly Asp Gln
1 5 10 15

Glu

<210> SEQ ID NO 32
<211> LENGTH: 17
<212> TYPE: PRT
<213> ORGANISM: Danio rerio

<400> SEQUENCE: 32

Tyr Ser Phe His Ser Val Thr Ile Gln Leu Glu Pro Gln Ala Asp Gln
1 5 10 15

Arg

<210> SEQ ID NO 33
<211> LENGTH: 17
<212> TYPE: PRT
<213> ORGANISM: Homo sapiens

<400> SEQUENCE: 33

-continued

```
Phe His Phe His Thr Val Thr Ile Gln Ile Glu Asp Tyr Ser Glu Asp
1               5                   10                  15

Met


<210> SEQ ID NO 34
<211> LENGTH: 17
<212> TYPE: PRT
<213> ORGANISM: Homo sapiens

<400> SEQUENCE: 34

Phe Gly Phe Ser Ser Cys Thr Leu Gln Val Glu Gln Tyr Gln Pro Glu
1               5                   10                  15

Met


<210> SEQ ID NO 35
<211> LENGTH: 17
<212> TYPE: PRT
<213> ORGANISM: Pyrococcus sp.

<400> SEQUENCE: 35

Phe Gly Ile Thr His Val Thr Ile Gln Leu Glu Thr Gly Arg Cys Lys
1               5                   10                  15

Glu


<210> SEQ ID NO 36
<211> LENGTH: 17
<212> TYPE: PRT
<213> ORGANISM: Escherichia coli

<400> SEQUENCE: 36

Val Asp Gly Asn Gln Ile Thr Ile Gln Met Glu Ser Lys Ile Asp Val
1               5                   10                  15

Gln


<210> SEQ ID NO 37
<211> LENGTH: 17
<212> TYPE: PRT
<213> ORGANISM: Homo sapiens

<400> SEQUENCE: 37

Ser Met His Asp Leu Thr Thr Ile Gln Gly Asp Glu Pro Val Gly Gln
1               5                   10                  15

Arg


<210> SEQ ID NO 38
<211> LENGTH: 69
<212> TYPE: PRT
<213> ORGANISM: Xenopus sp.

<400> SEQUENCE: 38

Met Lys Gly Ser Glu Glu Ala Tyr Leu Val Ser Asp Lys Ala Thr Lys
1               5                   10                  15

Met Tyr Ser Leu Thr Lys Asp Ser Glu Lys Asn His Pro Ser Lys Pro
            20                  25                  30

Pro Leu Gln Asp Glu Glu Asn Pro Gln Ser Lys Tyr His Cys His Asn
        35                  40                  45

Asn Asn Lys Lys Ala Tyr Asp Ala Arg Gln Arg Glu Gln Thr Phe Ala
    50                  55                  60

Lys Lys Lys Leu Cys
65
```

<210> SEQ ID NO 39
<211> LENGTH: 102
<212> TYPE: PRT
<213> ORGANISM: Xenopus sp.

<400> SEQUENCE: 39

```
Arg Asp Leu Leu Thr Val Leu Met Glu Gly Thr Arg Pro Gly Ile His
1               5                   10                  15

Tyr Ser Asp Val Lys Gln Ser Ile Leu Ala Val Asp Gly Val Lys Ser
            20                  25                  30

Val His Ser Leu His Leu Trp Ala Leu Thr Met Asn Gln Val Ile Leu
        35                  40                  45

Ser Ala His Ile Ala Thr Asp Ile Val Gly Glu Ser Lys Arg Ile Leu
    50                  55                  60

Lys Asp Val Thr Gln Asn Val Phe Ala Arg Phe Pro Phe His Ser Val
65                  70                  75                  80

Thr Ile Gln Val Glu Pro Ile Glu Asp Gln Ser Pro Glu Cys Met Phe
                85                  90                  95

Cys Tyr Glu Pro Thr Gln
            100
```

<210> SEQ ID NO 40
<211> LENGTH: 102
<212> TYPE: PRT
<213> ORGANISM: Mus musculus

<400> SEQUENCE: 40

```
Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Gln Asp Ser Gln Ser Val
    50                  55                  60

Arg Thr Gly Ile Ala Gln Ala Leu Ser Ser Phe Asp Leu His Ser Leu
65                  70                  75                  80

Thr Ile Gln Ile Glu Ser Ala Ala Asp Gln Asp Pro Ser Cys Leu Leu
                85                  90                  95

Cys Glu Asp Pro Gln Asp
            100
```

<210> SEQ ID NO 41
<211> LENGTH: 102
<212> TYPE: PRT
<213> ORGANISM: Mus musculus

<400> SEQUENCE: 41

```
Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Arg Asp Ser Gln Ser Val
    50                  55                  60
```

```
Arg Thr Gly Ile Ala Gln Ala Leu Ser Ser Phe Asp Leu His Ser Leu
65                  70                  75                  80

Thr Ile Gln Ile Glu Ser Ala Ala Asp Gln Asp Pro Ser Cys Leu Leu
                85                  90                  95

Cys Glu Asp Pro Gln Asp
            100


<210> SEQ ID NO 42
<211> LENGTH: 102
<212> TYPE: PRT
<213> ORGANISM: Mus musculus

<400> SEQUENCE: 42

Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Trp Asp Ser Gln Ser Val
    50                  55                  60

Arg Thr Gly Ile Ala Gln Ala Leu Ser Ser Phe Asp Leu His Ser Leu
65                  70                  75                  80

Thr Ile Gln Ile Glu Ser Ala Ala Asp Gln Asp Pro Ser Cys Leu Leu
                85                  90                  95

Cys Glu Asp Pro Gln Asp
            100


<210> SEQ ID NO 43
<211> LENGTH: 103
<212> TYPE: PRT
<213> ORGANISM: Mus musculus

<400> SEQUENCE: 43

Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Gln Asp Ser Gln Ser Val
    50                  55                  60

Arg Thr Gly Ile Ala Gln Ala Leu Ser Lys Ser Phe Asp Leu His Ser
65                  70                  75                  80

Leu Thr Ile Gln Ile Glu Ser Ala Ala Asp Gln Asp Pro Ser Cys Leu
                85                  90                  95

Leu Cys Glu Asp Pro Gln Asp
            100


<210> SEQ ID NO 44
<211> LENGTH: 103
<212> TYPE: PRT
<213> ORGANISM: Mus musculus

<400> SEQUENCE: 44

Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
```

-continued

```
            20                  25                  30

Ser Val His Ser Leu His Ile Trp Ser Leu Thr Val Asn Gln Val Ile
        35                  40                  45

Leu Ser Val His Val Ala Thr Ala Ala Ser Arg Asp Ser Gln Ser Val
    50                  55                  60

Arg Thr Gly Ile Ala Gln Ala Leu Ser Lys Ser Phe Asp Leu His Ser
65                  70                  75                  80

Leu Thr Ile Gln Ile Glu Ser Ala Ala Asp Gln Asp Pro Ser Cys Leu
                85                  90                  95

Leu Cys Glu Asp Pro Gln Asp
            100


<210> SEQ ID NO 45
<211> LENGTH: 103
<212> TYPE: PRT
<213> ORGANISM: Mus musculus

<400> SEQUENCE: 45

Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Trp Asp Ser Gln Ser Val
    50                  55                  60

Arg Thr Gly Ile Ala Gln Ala Leu Ser Lys Ser Phe Asp Leu His Ser
65                  70                  75                  80

Leu Thr Ile Gln Ile Glu Ser Ala Ala Asp Gln Asp Pro Ser Cys Leu
                85                  90                  95

Leu Cys Glu Asp Pro Gln Asp
            100


<210> SEQ ID NO 46
<211> LENGTH: 103
<212> TYPE: PRT
<213> ORGANISM: Mus musculus

<400> SEQUENCE: 46

Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Gln Asp Ser Gln Ser Val
    50                  55                  60

Arg Arg Glu Ile Ala Lys Ala Leu Ser Lys Ser Phe Asp Leu His Ser
65                  70                  75                  80

Leu Thr Ile Gln Ile Glu Ser Ala Ala Asp Gln Asp Pro Ser Cys Leu
                85                  90                  95

Leu Cys Glu Asp Pro Gln Asp
            100


<210> SEQ ID NO 47
<211> LENGTH: 103
<212> TYPE: PRT
```

<213> ORGANISM: Mus musculus

<400> SEQUENCE: 47

```
Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Arg Asp Ser Gln Ser Val
    50                  55                  60

Arg Arg Glu Ile Ala Lys Ala Leu Ser Lys Ser Phe Asp Leu His Ser
65                  70                  75                  80

Leu Thr Ile Gln Ile Glu Ser Ala Ala Asp Gln Asp Pro Ser Cys Leu
                85                  90                  95

Leu Cys Glu Asp Pro Gln Asp
            100
```

<210> SEQ ID NO 48
<211> LENGTH: 103
<212> TYPE: PRT
<213> ORGANISM: Mus musculus

<400> SEQUENCE: 48

```
Met Lys Asp Phe Ser Ile Leu Leu Met Glu Gly Val Pro Lys Gly Leu
1               5                   10                  15

Ser Tyr Asn Ser Val Lys Glu Ile Ile Leu Ala Val Asp Gly Val Ile
            20                  25                  30

Ser Val His Ser Leu His Ile Trp Ser Leu Thr Val Asn Gln Val Ile
        35                  40                  45

Leu Ser Val His Val Ala Thr Ala Ala Ser Trp Asp Ser Gln Ser Val
    50                  55                  60

Arg Arg Glu Ile Ala Lys Ala Leu Ser Lys Ser Phe Asp Leu His Ser
65                  70                  75                  80

Leu Thr Ile Gln Ile Glu Ser Ala Ala Asp Gln Asp Pro Ser Cys Leu
                85                  90                  95

Leu Cys Glu Asp Pro Gln Asp
            100
```

<210> SEQ ID NO 49
<211> LENGTH: 103
<212> TYPE: PRT
<213> ORGANISM: Homo sapiens

<400> SEQUENCE: 49

```
Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95
```

```
Phe Cys Glu Asp Pro Cys Asp
            100


<210> SEQ ID NO 50
<211> LENGTH: 103
<212> TYPE: PRT
<213> ORGANISM: Homo sapiens

<400> SEQUENCE: 50

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Gln Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp
            100


<210> SEQ ID NO 51
<211> LENGTH: 103
<212> TYPE: PRT
<213> ORGANISM: Homo sapiens

<400> SEQUENCE: 51

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Trp Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp
            100


<210> SEQ ID NO 52
<211> LENGTH: 11
<212> TYPE: PRT
<213> ORGANISM: Artificial
<220> FEATURE:
<223> OTHER INFORMATION: synthetic peptide

<400> SEQUENCE: 52

Pro Ser Thr Pro Pro Gly Ser Ser Gly Gly Gly
1               5                   10


<210> SEQ ID NO 53
<211> LENGTH: 216
<212> TYPE: PRT
```

<213> ORGANISM: Homo sapiens

<400> SEQUENCE: 53

```
Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Arg Asp Ser Gln Val
                165                 170                 175

Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215
```

<210> SEQ ID NO 54
<211> LENGTH: 216
<212> TYPE: PRT
<213> ORGANISM: Homo sapiens

<400> SEQUENCE: 54

```
Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
```

```
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Gln Asp Ser Gln Val
                165                 170                 175

Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215


<210> SEQ ID NO 55
<211> LENGTH: 216
<212> TYPE: PRT
<213> ORGANISM: Homo sapiens

<400> SEQUENCE: 55

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Arg Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Trp Asp Ser Gln Val
                165                 170                 175

Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215


<210> SEQ ID NO 56
<211> LENGTH: 216
<212> TYPE: PRT
<213> ORGANISM: Homo sapiens

<400> SEQUENCE: 56

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
```

-continued

```
            20                  25                  30

Ser Val His Ser Leu His Ile Trp Ser Leu Thr Met Asn Gln Val Ile
        35                  40                  45

Leu Ser Ala His Val Ala Thr Ala Ala Ser Gln Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Gln Asp Ser Gln Val
                165                 170                 175

Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215


<210> SEQ ID NO 57
<211> LENGTH: 216
<212> TYPE: PRT
<213> ORGANISM: Homo sapiens

<400> SEQUENCE: 57

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Gln Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Arg Asp Ser Gln Val
                165                 170                 175
```

```
Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215


<210> SEQ ID NO 58
<211> LENGTH: 216
<212> TYPE: PRT
<213> ORGANISM: Homo sapiens

<400> SEQUENCE: 58

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Gln Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Gln Asp Ser Trp Val
                165                 170                 175

Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215


<210> SEQ ID NO 59
<211> LENGTH: 216
<212> TYPE: PRT
<213> ORGANISM: Homo sapiens

<400> SEQUENCE: 59

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Trp Asp Ser Gln Val Val
    50                  55                  60
```

```
Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Trp Asp Ser Gln Val
                165                 170                 175

Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215


<210> SEQ ID NO 60
<211> LENGTH: 216
<212> TYPE: PRT
<213> ORGANISM: Homo sapiens

<400> SEQUENCE: 60

Met Lys Asp Phe Ser Ile Leu Leu Met Glu Gly Val Pro Lys Ser Leu
1               5                   10                  15

Asn Tyr Ser Gly Val Lys Glu Leu Ile Leu Ala Val Asp Gly Val Leu
            20                  25                  30

Ser Val His Ser Leu His Ile Trp Ser Leu Thr Met Asn Gln Val Ile
        35                  40                  45

Leu Ser Ala His Val Ala Thr Ala Ala Ser Trp Asp Ser Gln Val Val
    50                  55                  60

Arg Arg Glu Ile Ala Lys Ala Leu Ser Lys Ser Phe Thr Met His Ser
65                  70                  75                  80

Leu Thr Ile Gln Met Glu Ser Pro Val Asp Gln Asp Pro Asp Cys Leu
                85                  90                  95

Phe Cys Glu Asp Pro Cys Asp Pro Ser Thr Pro Pro Gly Ser Ser Gly
            100                 105                 110

Gly Gly Lys Asp Phe Ser Ile Leu Leu Met Glu Gly Val Pro Lys Ser
        115                 120                 125

Leu Asn Tyr Ser Gly Val Lys Glu Leu Ile Leu Ala Val Asp Gly Val
    130                 135                 140

Leu Ser Val His Ser Leu His Ile Trp Ser Leu Thr Met Asn Gln Val
145                 150                 155                 160

Ile Leu Ser Ala His Val Ala Thr Ala Ala Ser Arg Asp Ser Gln Val
                165                 170                 175

Val Arg Arg Glu Ile Ala Lys Ala Leu Ser Lys Ser Phe Thr Met His
            180                 185                 190

Ser Leu Thr Ile Gln Met Glu Ser Pro Val Asp Gln Asp Pro Asp Cys
        195                 200                 205

Leu Phe Cys Glu Asp Pro Cys Asp
    210                 215
```

<210> SEQ ID NO 61
<211> LENGTH: 216
<212> TYPE: PRT
<213> ORGANISM: Homo sapiens

<400> SEQUENCE: 61

Met Lys Asp Phe Ser Ile Leu Leu Met Glu Gly Val Pro Lys Ser Leu
1 5 10 15

Asn Tyr Ser Gly Val Lys Glu Leu Ile Leu Ala Val Asp Gly Val Leu
20 25 30

Ser Val His Ser Leu His Ile Trp Ser Leu Thr Met Asn Gln Val Ile
35 40 45

Leu Ser Ala His Val Ala Thr Ala Ala Ser Trp Asp Ser Gln Val Val
50 55 60

Arg Arg Glu Ile Ala Lys Ala Leu Ser Lys Ser Phe Thr Met His Ser
65 70 75 80

Leu Thr Ile Gln Met Glu Ser Pro Val Asp Gln Asp Pro Asp Cys Leu
85 90 95

Phe Cys Glu Asp Pro Cys Asp Pro Ser Thr Pro Pro Gly Ser Ser Gly
100 105 110

Gly Gly Lys Asp Phe Ser Ile Leu Leu Met Glu Gly Val Pro Lys Ser
115 120 125

Leu Asn Tyr Ser Gly Val Lys Glu Leu Ile Leu Ala Val Asp Gly Val
130 135 140

Leu Ser Val His Ser Leu His Ile Trp Ser Leu Thr Met Asn Gln Val
145 150 155 160

Ile Leu Ser Ala His Val Ala Thr Ala Ala Ser Gln Asp Ser Gln Val
165 170 175

Val Arg Arg Glu Ile Ala Lys Ala Leu Ser Lys Ser Phe Thr Met His
180 185 190

Ser Leu Thr Ile Gln Met Glu Ser Pro Val Asp Gln Asp Pro Asp Cys
195 200 205

Leu Phe Cys Glu Asp Pro Cys Asp
210 215

<210> SEQ ID NO 62
<211> LENGTH: 181
<212> TYPE: PRT
<213> ORGANISM: Homo sapiens

<400> SEQUENCE: 62

Met Glu Phe Leu Glu Arg Thr Tyr Leu Val Asn Asp Lys Ala Ala Lys
1 5 10 15

Met Tyr Ala Phe Thr Leu Glu Ser Val Glu Leu Gln Gln Lys Pro Val
20 25 30

Asn Lys Asp Gln Cys Pro Arg Glu Arg Pro Glu Glu Leu Glu Ser Gly
35 40 45

Gly Met Tyr His Cys His Ser Gly Ser Lys Pro Thr Glu Lys Gly Ala
50 55 60

Asn Glu Tyr Ala Tyr Ala Lys Trp Lys Leu Cys Ser Gly Gly Gly Lys
65 70 75 80

Asp Phe Ser Ile Leu Leu Met Glu Gly Val Pro Lys Ser Leu Asn Tyr
85 90 95

Ser Gly Val Lys Glu Leu Ile Leu Ala Val Asp Gly Val Leu Ser Val
100 105 110

```
His Ser Leu His Ile Trp Ser Leu Thr Met Asn Gln Val Ile Leu Ser
        115                 120                 125

Ala His Val Ala Thr Ala Ala Ser Trp Asp Ser Gln Val Val Arg Arg
    130                 135                 140

Glu Ile Ala Lys Ala Leu Ser Lys Ser Phe Thr Met His Ser Leu Thr
145                 150                 155                 160

Ile Gln Met Glu Ser Pro Val Asp Gln Asp Pro Asp Cys Leu Phe Cys
                165                 170                 175

Glu Asp Pro Cys Asp
            180


<210> SEQ ID NO 63
<211> LENGTH: 181
<212> TYPE: PRT
<213> ORGANISM: Homo sapiens

<400> SEQUENCE: 63

Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Gly Gly Gly Lys
65                  70                  75                  80

Asp Phe Ser Ile Leu Leu Met Glu Gly Val Pro Lys Ser Leu Asn Tyr
                85                  90                  95

Ser Gly Val Lys Glu Leu Ile Leu Ala Val Asp Gly Val Leu Ser Val
            100                 105                 110

His Ser Leu His Ile Trp Ser Leu Thr Met Asn Gln Val Ile Leu Ser
        115                 120                 125

Ala His Val Ala Thr Ala Ala Ser Arg Asp Ser Gln Val Val Arg Arg
    130                 135                 140

Glu Ile Ala Lys Ala Leu Ser Lys Ser Phe Thr Met His Ser Leu Thr
145                 150                 155                 160

Ile Gln Met Glu Ser Pro Val Asp Gln Asp Pro Asp Cys Leu Phe Cys
                165                 170                 175

Glu Asp Pro Cys Asp
            180


<210> SEQ ID NO 64
<211> LENGTH: 132
<212> TYPE: PRT
<213> ORGANISM: Homo sapiens

<400> SEQUENCE: 64

Met Tyr His Cys His Ser Gly Ser Lys Pro Thr Glu Lys Gly Ala Asn
1               5                   10                  15

Glu Tyr Ala Tyr Ala Lys Trp Lys Leu Cys Ser Gly Gly Gly Lys Asp
            20                  25                  30

Phe Ser Ile Leu Leu Met Glu Gly Val Pro Lys Ser Leu Asn Tyr Ser
        35                  40                  45

Gly Val Lys Glu Leu Ile Leu Ala Val Asp Gly Val Leu Ser Val His
    50                  55                  60
```

Ser Leu His Ile Trp Ser Leu Thr Met Asn Gln Val Ile Leu Ser Ala
65 70 75 80

His Val Ala Thr Ala Ala Ser Trp Asp Ser Gln Val Val Arg Arg Glu
85 90 95

Ile Ala Lys Ala Leu Ser Lys Ser Phe Thr Met His Ser Leu Thr Ile
100 105 110

Gln Met Glu Ser Pro Val Asp Gln Asp Pro Asp Cys Leu Phe Cys Glu
115 120 125

Asp Pro Cys Asp
130

<210> SEQ ID NO 65
<211> LENGTH: 132
<212> TYPE: PRT
<213> ORGANISM: Homo sapiens

<400> SEQUENCE: 65

Met Tyr His Cys His Ser Gly Ser Lys Pro Thr Glu Lys Gly Ala Asn
1 5 10 15

Glu Tyr Ala Tyr Ala Lys Trp Lys Leu Cys Ser Gly Gly Gly Lys Asp
20 25 30

Phe Ser Ile Leu Leu Met Glu Gly Val Pro Lys Ser Leu Asn Tyr Ser
35 40 45

Gly Val Lys Glu Leu Ile Leu Ala Val Asp Gly Val Leu Ser Val His
50 55 60

Ser Leu His Ile Trp Ser Leu Thr Met Asn Gln Val Ile Leu Ser Ala
65 70 75 80

His Val Ala Thr Ala Ala Ser Arg Asp Ser Gln Val Val Arg Arg Glu
85 90 95

Ile Ala Lys Ala Leu Ser Lys Ser Phe Thr Met His Ser Leu Thr Ile
100 105 110

Gln Met Glu Ser Pro Val Asp Gln Asp Pro Asp Cys Leu Phe Cys Glu
115 120 125

Asp Pro Cys Asp
130

<210> SEQ ID NO 66
<211> LENGTH: 182
<212> TYPE: PRT
<213> ORGANISM: Homo sapiens

<400> SEQUENCE: 66

Met Lys Asp Phe Ser Ile Leu Leu Met Glu Gly Val Pro Lys Ser Leu
1 5 10 15

Asn Tyr Ser Gly Val Lys Glu Leu Ile Leu Ala Val Asp Gly Val Leu
20 25 30

Ser Val His Ser Leu His Ile Trp Ser Leu Thr Met Asn Gln Val Ile
35 40 45

Leu Ser Ala His Val Ala Thr Ala Ala Ser Arg Asp Ser Gln Val Val
50 55 60

Arg Arg Glu Ile Ala Lys Ala Leu Ser Lys Ser Phe Thr Met His Ser
65 70 75 80

Leu Thr Ile Gln Met Glu Ser Pro Val Asp Gln Asp Pro Asp Cys Leu
85 90 95

Phe Cys Glu Asp Pro Cys Asp Gly Gly Gly Met Glu Phe Leu Glu Arg
100 105 110

-continued

```
Thr Tyr Leu Val Asn Asp Lys Ala Ala Lys Met Tyr Ala Phe Thr Leu
        115                 120                 125

Glu Ser Val Glu Leu Gln Gln Lys Pro Val Asn Lys Asp Gln Cys Pro
    130                 135                 140

Arg Glu Arg Pro Glu Glu Leu Glu Ser Gly Gly Met Tyr His Cys His
145                 150                 155                 160

Ser Gly Ser Lys Pro Thr Glu Lys Gly Ala Asn Glu Tyr Ala Tyr Ala
                165                 170                 175

Lys Trp Lys Leu Cys Ser
            180


<210> SEQ ID NO 67
<211> LENGTH: 244
<212> TYPE: PRT
<213> ORGANISM: Homo sapiens

<400> SEQUENCE: 67

Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Ala Ser Asp Ala
65                  70                  75                  80

Ala His Leu Leu Ile Asp Ser Ser Lys Pro Pro Ser Lys Arg Leu Thr
                85                  90                  95

Phe Gly Trp His Arg Ala Glu Cys Glu Arg Leu Leu Tyr Pro Asp Tyr
            100                 105                 110

Gln Ile Gln Ala Thr Leu His Gln Arg Cys Leu Gly His Asn His Lys
        115                 120                 125

Glu Val Gln Ala Asn Ala Ser Val Arg Lys Pro Glu Tyr Lys Lys Asp
    130                 135                 140

Phe Ser Ile Leu Leu Met Glu Gly Val Pro Lys Ser Leu Asn Tyr Ser
145                 150                 155                 160

Gly Val Lys Glu Leu Ile Leu Ala Val Asp Gly Val Leu Ser Val His
                165                 170                 175

Ser Leu His Ile Trp Ser Leu Thr Met Asn Gln Val Ile Leu Ser Ala
            180                 185                 190

His Val Ala Thr Ala Ala Ser Trp Asp Ser Gln Val Val Arg Arg Glu
        195                 200                 205

Ile Ala Lys Ala Leu Ser Lys Ser Phe Thr Met His Ser Leu Thr Ile
    210                 215                 220

Gln Met Glu Ser Pro Val Asp Gln Asp Pro Asp Cys Leu Phe Cys Glu
225                 230                 235                 240

Asp Pro Cys Asp
```

DIAGNOSTIC AND THERAPEUTIC TARGET FOR AUTOIMMUNE DISEASES AND USES THEREOF

CROSS REFERENCE TO RELATED APPLICATION

This application is a national stage application under 35 U.S.C. 371 of PCT Application No. PCT/US2007/089125 having an international filing date of Dec. 28, 2007, which designated the United States, which PCT application claimed the benefit of U.S. Application Ser. No. 60/882,815, filed Dec. 29, 2006, the entire disclosure of each of which is hereby incorporated herein by reference.

REFERENCE TO SEQUENCE LISTING

This application contains a Sequence Listing submitted as an electronic text file named "5970-94-PUS_ST25.txt" having a size in bytes of 83 KB, and created on Jan. 28, 2010. The information contained in this electronic file is hereby incorporated by reference in its entirety pursuant to 37 CFR §1.52 (e)(5).

FIELD OF THE INVENTION

This invention generally relates to the identification of autoantigen targets, and particularly, autoantigen targets in type I autoimmune diabetes (T1D), and more particularly, the protein ZnT8 as a novel autoantigen, upon which therapeutic, diagnostic, and prognostic tools and methods are based and described herein.

BACKGROUND OF THE INVENTION

Autoimmune disorders are conditions caused by an immune response against the body's own tissues. Autoimmune disorders result in destruction of one or more types of body tissues, abnormal growth of an organ, or changes in organ function. The disorder may affect only one organ or tissue type or may affect multiple organs and tissues.

Type 1 autoimmune diabetes (T1D) in humans and the NOD mouse model is a polygenic T-cell dependent autoimmune disease, characterized by the selective destruction of the β cells of the islets of Langerhans (1-3) arising from a breakdown in tolerance to β cell antigens (4) in susceptible individuals who have inherent defects in critical immunomodulatory mechanisms (5) (e.g., individuals who exhibit a pathogenic rather than a protective immune response to self). Pancreatic exocrine and endocrine cells that share the same developmental lineage as the β-cell and are often in direct contact with β-cells are largely unaffected, and insulitis resolves once the β-cells are lost, which suggests that the autoimmune targets are largely β-cell specific. Many of the known diabetes autoantigens, such as insulin and IGRP reflect this cell specificity, however, the list of known immune targets is by no means comprehensive. This applies especially to the antigens recognized by the cellular arm of the immune system, and the targets of the majority of $CD4^+$ diabetogenic T-cells remain elusive in spite of more than a decade of investigation. Few new targets have emerged in recent years using the immunological screening procedures that originally identified such molecules as GAD65, IA-2 and ICA 69.

Many individuals with a strong genetic predisposition to T1D never develop overt disease (50% of monozygotic twins with one diabetic member remain discordant) and non-germ line encoded factors significantly influence the rate of progression of T1D (7). This low penetrance and variable natural history points to the importance of environmental factors, and also the stochastic nature of the immune response itself. Therapeutic strategies that shift this balance towards a more toleragenic environment have the potential to prevent or slow the progression of autoimmunity to destructive insulitis.

There appears to be a restricted number of islet-cell reactive T-cell clones in early pancreatic infiltrates in NOD mice (16; 17) and disease progression appears to involve epitope spreading and (18) avidity maturation of early T-cell responses (19) along with the recruitment of new autoantigens (20). Numerous islet-specific $CD4^+$ and $CD8^+$ T-cell clones have been isolated from spleen, lymph nodes or islet infiltrates of pre- or newly diabetic NOD mice (21-25) whose cognate antigens are poorly defined and do not appear to correspond to any of the known serological markers of diabetes autoimmunity in humans such as GAD65, the insulin granule membrane proteins ICA512 (IA-2) and phogrin (IA-2β) (20), carboxypeptidase E (26), ICA69 (27) and sulphated glycolipids (28). The molecular targets of autoreactive T-cells may include either an unidentified component of β-cells, or known β-cell proteins that are intrinsically unable to elicit a humoral response. Accordingly, defining the cognate antigens for them remains an important goal, and with the recent advances in genomic and proteomic techniques, now appears a realistic aim. Thus the target of the well studied NY8.3 $CD8^+$ clone (23) was recently shown to be a peptide derived from the β-cell protein IGRP (islet glucose 6-phosphatase related protein) by using a combination of a sensitive bioassay and analysis of proteomic peptides eluted from H-$2K^d$ molecules from NIT1 insulinoma cells (29).

Although the humoral response per se probably contributes little to the pathogenesis of the disease (30), identification of the molecular targets of B-lymphocytes is also an important objective, since B-cells play a role in antigen presentation in T1D (31). In addition, circulating autoantibodies provide useful pre-clinical markers for diabetic autoimmunity. The production of high affinity antibodies is a T-dependent process, and thus it is reasonable to expect that molecules recognized by autoantibodies should also be the targets of autoreactive diabetogenic T-cells. This hypothesis appears correct, at least for insulin, phogrin and GAD65 (32-34). The list of known targets, while long, is far from comprehensive. This is highlighted by the fact that serological diagnosis of pre-T1D determined by immunohistochemistry of human pancreas is still the most sensitive index, simply because it defines additional targets that are not among the autoantigens defined in molecular terms.

There is a continuing debate about whether there are primary or initiating autoantigens in T1D, and in other autoimmune diseases. For TID, the best candidate in the NOD mouse at present is insulin (33; 35-38) although it has also been proposed that IGRP can play this crucial role (29; 39; 40) based upon the precursor frequency of T-cells recognizing this antigen in islet infiltrates. An alternative view is that disease results from polyclonal activation due to a breakdown in normal toleragenic mechanisms that would otherwise generate regulatory cells directed to the same molecules (41). Given the latter scenario, the inventors hypothesize that any molecule that is a significant target of autoimmunity in T1D is a candidate for use in antigen-based therapy. Effective tolerization strategies in NOD mice based on immunization with the native epitopes of insulin (42; 43), GAD65 (44-48), HSP 65 (49) and IGRP (50) appear to bear this out. Moreover, the inventors' preliminary studies with IA-2 and phogrin show that a known mouse and human peptide epitope (peptide 7 (51)) likewise slows the emergence of disease when administered neonatally to NOD mice. Other known T-cell targets, including IAPP (52), IMOGEN 38 (53-57) appear not to have been characterized in this regard.

Examples of putative molecular mimicry between autoantigens and viral proteins based upon sequence homology abound in the scientific literature (58). For example, in the case of T1D, cross-reactivity between GAD65 and Coxsackie B3 P2-C protein (59) or human cytomegalovirus major DNA-binding protein (60), and IA-2 with rotavirus VP7 (61) or Coxsackie B4 VP1 (62) have been proposed. Similarly, mimicry between proinsulin and GAD65 has also been postulated (63). Exposure to a molecular mimic could conceivably either trigger autoimmunity, or protect against it, by establishing and consolidating immune networks. Epidemiological studies of autoimmune triggering by infectious agents in man have not been particularly informative possibly because of the long prodrome of the disease and failure to identify a specific organism (or rare serotype of a common pathogen) that is involved (14). Protective responses that are central to the “hygiene hypothesis” by their very nature are more difficult to establish.

The non-obese diabetic (NOD) mouse is currently the best model of human T1D (8) where three stages of disease progression are evident, namely, expansion of autoreactive T-cells (“checkpoint 0”), their homing to the pancreatic islets (“checkpoint 1”), and the transition from a benign peri-insulitis to an invasive insulitis resulting in β-cell destruction (“checkpoint 2”) (9). It has been postulated that passage through “checkpoint 1” coincides with a wave of islet cell apoptosis that leads to enhanced presentation of β-cell antigens in the pancreatic lymph nodes. A related hypothesis suggests that exposure to novel antigens in the gut at this time (when weaning is occurring) results in activation of Th1 polarized T-cells that subsequently migrate to the pancreas and perturb the response in the draining nodes such that an immunogenic response to islet cell antigens results. A similar involvement of post-natal islet cell apoptosis (10), congenital β-cell abnormalities (11), and dietary (12; 13) or enteroviral (14) triggers have also been proposed in human T1D, although at present, their relative roles (if any), and generality as casual factors, remain controversial. Nevertheless it is clear that islet cell antigens are critical to the disease process (15), and that a detailed knowledge of their molecular characteristics is essential both to the rational design of immunotherapies, and in the monitoring and identification of at-risk individuals.

There are upwards of 2 million type 1 diabetes patients in the United States alone, all of whom require lifelong multiple daily doses of insulin to stay alive. The majority of these individuals will suffer from the complications of diabetes within their lifetime and it is estimated that at any age, their lifespan may be reduced by up to a third. Prevention or even slowing of the development of the disease would thus have immense social and economic benefits. There are a number of experimental approaches to diabetes prevention and reversal that have proven to be very effective in rodent models of T1D and which are currently being tested in clinical trials. For example, preliminary findings with anti-CD3 monoclonal antibody treatment are particularly promising. To be efficacious, any immune-based therapy requires diagnostic tests to establish whether intervention is appropriate and when to implement therapy relative to staging of the disease. Once therapy is initiated, it is essential to assess its short term and long term efficacy. Diagnostic assays based on humoral or cellular autoreactivity to autoantigens that are useful in monitoring disease progression are essential in making any decision to treat a patient and in the subsequent monitoring of treatment outcome.

Therefore, there is a continued need in the art for improved diagnostic assays for T1D, as well as new immunotherapeutics based on disease targets. In addition, many targets identified in one autoimmune disease, such as TID, will also be targets in other autoimmune diseases, thereby expanding the available diagnostic and therapeutic approaches in a variety of autoimmune conditions.

SUMMARY OF THE INVENTION

One embodiment of the invention relates to various fragments of ZnT8. In one aspect, the fragment comprises, consists essentially of, or consists of, at least the 10 C-terminal amino acids of ZnT8. In one aspect, the fragment comprises, consists essentially of, or consists of, at least the 25 C-terminal amino acids of ZnT8. In another aspect, the fragment comprises, consists essentially of, or consists of, at least the 50 C-terminal amino acids of ZnT8. In another aspect, the fragment comprises, consists essentially of, or consists of, at least the 75 C-terminal amino acids of ZnT8. In yet another aspect, the fragment comprises, consists essentially of, or consists of, at least the 100 C-terminal amino acids of ZnT8. In one aspect, the fragment comprises, consists essentially of, or consists of, at least the 101 C-terminal amino acids of ZnT8. In one aspect, the fragment comprises, consists essentially of, or consists of, at least the 102 C-terminal amino acids of ZnT8. In another aspect, the fragment comprises, consists essentially of, or consists of, at least the 104 C-terminal amino acids of ZnT8. In one aspect, the fragment comprises, consists essentially of, or consists of, at least the 350 C-terminal amino acids of ZnT8. In another aspect, the fragment comprises, consists essentially of, or consists of, at least the amino acid sequence SLTIQMES (positions 346-353 of SEQ ID NO:2). In one aspect, aspect, the fragment comprises, consists essentially of, or consists of, at least the 10 N-terminal amino acids of ZnT8. In one aspect, the fragment comprises, consists essentially of, or consists of, at least the 25 N-terminal amino acids of ZnT8. In another aspect, the fragment comprises, consists essentially of, or consists of, at least the 50 N-terminal amino acids of ZnT8. In one aspect, the fragment comprises, consists essentially of, or consists of, at least the 74 N-terminal amino acids of ZnT8.

In any of the above-aspects of the invention, the fragment can include an amino acid position selected from the group consisting of E352 and S353, with respect to SEQ ID NO:2.

In any of the above-aspects of the invention, ZnT8 can be human ZnT8 (SEQ ID NO:2). In one aspect, the fragment comprises position 325 of SEQ ID NO:2. In another aspect, the ZnT8 is a polymorphic variant of SEQ ID NO:2. In another aspect, the fragment comprises position 325 of SEQ ID NO:2, and in one embodiment of this aspect of the invention, the amino acid at position 325 is a tryptophan, glutamine, or arginine.

Another embodiment of the invention relates to a fragment of ZnT8, comprising, consisting essentially of, or consisting of, a fragment represented by any one of SEQ ID NOs: 8-24 or 40-65.

One embodiment of the invention relates to a chimeric protein, comprising, consisting essentially of, or consisting of, any two or more fragments as described herein. In one aspect, the chimeric protein comprises an N-terminal fragment of ZnT8 and a C-terminal fragment of ZnT8. In another aspect, the chimeric protein comprises two C-terminal fragments of ZnT8, wherein each of the fragments comprises amino acid position 325, and wherein each of the fragments comprises a different amino acid at position 325. In one aspect, one fragment comprises an arginine at position 325 and wherein a second fragment comprises a tryptophan at position 325.

Yet another embodiment of the invention relates to a fragment or homologue of ZnT8 comprising at least one epitope of ZnT8 that is selectively bound by an anti-ZnT8 antibody. In one aspect, the anti-ZnT8 antibody is an antibody obtained from an individual. In one aspect, the individual has, or is suspected of having, type I diabetes.

Another embodiment of the invention relates to a fragment or homologue of ZnT8 comprising at least one epitope of ZnT8 that is specifically recognized by a ZnT8-specific T cell receptor.

In any of the above-described embodiments, in one aspect, the fragment or chimeric protein is complexed with at least one targeting moiety, to target the fragment or chimeric protein to a cell or site in a tissue or body. In one aspect, the targeting moiety targets T cells. In another aspect, the targeting moiety targets ZnT8-specific autoreactive T cells.

In any of the above-described embodiments, in one aspect, the fragment or chimeric protein is complexed with a toxin that induces apoptosis in or is otherwise toxic to T cells or B cells.

In any of the above-described embodiments, in one aspect, the fragment or chimeric protein is linked to a detectable label.

Another embodiment of the invention relates to a homologue of ZnT8, comprising a protein that is less than 99% identical to a naturally occurring ZnT8 protein, and that is at least 90% identical to SEQ ID NO:2. In one aspect, the protein is at least 95% identical to SEQ ID NO:2. In another aspect, the protein comprises position 325 of SEQ ID NO:2, and wherein the amino acid at position 325 is an arginine, a tryptophan or a glutamine.

Yet another embodiment of the invention relates to a vaccine comprising ZnT8 or a variant or fragment thereof, wherein the vaccine elicits an immune response that suppresses or eliminates ZnT8-specific autoreactive T cells in an individual.

Another embodiment of the invention relates to an antibody or antigen binding fragment thereof that selectively binds to ZnT8 or a fragment or a variant thereof, and suppresses or reduces ZnT8-specific autoimmune responses in an individual. In one aspect, the antibody is a monoclonal antibody.

Yet another embodiment of the invention relates to a method to diagnose an individual who is susceptible to or who is developing an autoimmune disease, comprising detecting antibodies that selectively bind to ZnT8 in a test sample from the individual, wherein detection of increased antibodies in the individual as compared to a negative control, indicates that the individual is susceptible to or is developing the autoimmune disease. In one aspect, the method comprises detecting antibodies that selectively bind to human ZnT8, wherein the amino acid at position 325 is an arginine, a tryptophan, and/or a glutamine.

Another embodiment of the invention relates to a method to diagnose an individual who is susceptible to or who is developing an autoimmune disease, comprising detecting ZnT8-specific T cell responses in a test sample from the individual, wherein detection of increased ZnT8-specific T cell responses in the individual as compared to a negative control, indicates that the individual is susceptible to or is developing an autoimmune disease. In one aspect, the method comprises detecting T cell responses specific for a human ZnT8 comprising an arginine at position 325. In one aspect, the method comprises detecting T cell responses specific for a human ZnT8, wherein the amino acid at position 325 is an arginine, a tryptophan, and/or a glutamine.

In any of the above-described methods, when the individual is susceptible or developing the autoimmune disease, the method can further include administering to the individual a therapeutic agent that targets an epitope of ZnT8 comprising the amino acid at position 325 in the individual. In one aspect, the agent is a protein, peptide or agonist of the ZnT8 in the individual that tolerizes the immune response of the individual to the ZnT8 protein. In one aspect, the agent stimulates an immune response against the ZnT8 protein.

In any of the above-described methods, in one aspect, the autoimmune disease is type I diabetes.

Another embodiment of the invention relates to a method to monitor the progression of type I diabetes autoimmunity in an individual from an initial benign autoreactivity to destructive insulitis, comprising detecting antibodies that selectively bind to ZnT8 in a test sample from the individual, wherein detection of increased antibodies in the individual as compared to a prior measurement of antibodies in the same individual, indicates that the individual is progressing toward destructive insulitis. In one aspect, the method comprises detecting antibodies that selectively bind to human ZnT8, wherein the amino acid at position 325 is an arginine, a tryptophan, and/or a glutamine.

Another embodiment of the invention relates to a method to monitor the progression of type I diabetes autoimmunity in an individual from an initial benign autoreactivity to destructive insulitis, comprising detecting ZnT8-specific T cell responses in a test sample from the individual, wherein detection of increased ZnT8-specific T cell responses in the individual as compared to a prior measurement of ZnT8-specific T cell responses in the same individual, indicates that the individual is progressing toward destructive insulitis. In one aspect, the method comprises detecting T cell responses specific for a human ZnT8 comprising an arginine at position 325, a tryptophan, and/or a glutamine.

Yet another embodiment of the invention relates to a method to monitor the efficacy of a treatment for preventing type I diabetes, delaying the onset of type I diabetes, or ameliorating autoimmunity in prediabetic individuals, comprising detecting antibodies that selectively bind to ZnT8 in a test sample from the individual, wherein detection of decreased or substantially the same level of antibodies in the individual as compared to a prior measurement of antibodies in the same individual, indicates that the treatment is effective, and wherein detection of increased antibodies in the individual as compared to a prior measurement of antibodies in the same individual indicates that the treatment is not effective. In one aspect, the method comprises detecting antibodies that selectively bind to human ZnT8, wherein the amino acid at position 325 is an arginine, a tryptophan, and/or a glutamine.

Yet another embodiment of the invention relates to a method to monitor the efficacy of a treatment for preventing type I diabetes, delaying the onset of type I diabetes, or ameliorating autoimmunity in prediabetic individuals, comprising detecting ZnT8-specific T cell responses in a test sample from the individual, wherein detection of decreased or substantially the same level of ZnT8-specific T cell responses in the individual as compared to a prior measurement of ZnT8-specific T cell responses in the same individual, indicates that the treatment is effective, and wherein detection of increased ZnT8-specific T cell responses in the individual as compared to a prior measurement of ZnT8-specific T cell responses in the same individual indicates that the treatment is not effective. In one aspect, the method comprises detecting T cell responses specific for a human ZnT8 comprising an arginine at position 325, a tryptophan, and/or a glutamine.

In one aspect of any of the above-described methods detecting antibodies, the method can include the use of an assay selected from, but not limited to: radioimmunoprecipitation assay, ELISA, time-resolved fluorescence assay, and luminescence assay. In one aspect, the method includes the use of a competitive Europium assay.

In one aspect of any of the above-described methods detecting T cell responses, the method can include the use of an assay selected from, but not limited to, a T cell proliferation assay, a binding assay using soluble MHC tetramers, a binding assay using soluble T cell receptors, and an ELISPOT assay.

In any of the above-identified methods, in one embodiment, the method comprises the use of ZnT8 or a fragment or variant thereof, including, but not limited to, any of the ZnT8 fragments described herein.

Yet another embodiment of the invention relates to an assay kit for performing any method described herein. The kit includes: (a) a ZnT8 protein or variant or fragment thereof; (b) a reagent or reagents for detecting an antibody that selectively binds to ZnT8; and/or a reagent or reagents for detecting a ZnT8-specific T cell response.

Another embodiment of the invention relates to a method to prevent an autoimmune disease, delay the onset of the autoimmune disease, or ameliorate autoimmunity in an individual with the autoimmune disease (including ameliorating any one or more symptoms of the disease), comprising administering to an individual in need thereof, an agent that elicits a ZnT8-specific immune response that protects cells or tissues in the patient that are targeted by the autoimmune disease. In one aspect, the autoimmune disease is type I diabetes, and wherein the agent protects β cells of the pancreatic islet.

Yet another embodiment of the invention relates to a method to prevent an autoimmune disease, delay the onset of the autoimmune disease, or ameliorate autoimmunity in an individual with the autoimmune disease (including ameliorating any one or more symptoms of the disease), comprising administering to an individual in need thereof, an agent that targets ZnT8-specific T cells in the individual, and induces necrosis or apoptosis of the ZnT8-specific T cells. In one aspect, the autoimmune disease is type I diabetes, and wherein the agent induces necrosis or apoptosis of the ZnT8-specific T cells.

Another embodiment of the invention relates to a method to prevent an autoimmune disease, delay the onset of the autoimmune disease, or ameliorate autoimmunity in an individual with the autoimmune disease (including ameliorating any one or more symptoms of the disease), comprising administering to an individual in need thereof, an agent that induces tolerance in ZnT8-specific T cells in the individual. In one aspect, the autoimmune disease is type I diabetes, and wherein the agent induces tolerance ZnT8-specific T cells in the individual.

In any of the above-described therapeutic methods, in one aspect, the agent is ZnT8, a homologue thereof, a fragment thereof, or a synthetic mimetic thereof. In one aspect, the agent is a fragment or chimeric protein, homologue, or a fragment thereof, as described anywhere herein. In one aspect, the agent is an antibody that competes with natural autoantibodies in the individual for binding of ZnT8 in the individual. In one aspect, the agent is specific for a polymorphic variant of human ZnT8 comprising an arginine at position 325. In one aspect, the agent is specific for a polymorphic variant of human ZnT8 comprising a tryptophan at position 325. In one aspect, the agent is specific for a polymorphic variant of human ZnT8 comprising a glutamine at position 325.

Another embodiment of the invention relates to the use of ZnT8, a variant thereof, a fragment thereof, a synthetic mimetic thereof, or an antibody that binds to said ZnT8, homologue thereof or fragment thereof, in a diagnostic, prognostic or therapeutic method as described substantially herein.

Yet another embodiment of the invention relates to any method, reagent, ZnT8 fragment, homologue, variant, chimeric protein, fusion protein, or nucleic acid encoding the same, or antibody selectively binding to the same, as substantially described herein.

BRIEF DESCRIPTION OF THE FIGURES OF THE INVENTION

FIG. 1 is a graph showing diabetes-specific autoantibodies to Slc30A8.

FIGS. 2A and 2B show the expression and purification of a membrane associated diabetes autoantigen in *Drosophila* S2 cells. FIG. 2A is a digitized image showing expression of the mIGRP V5 His construct was induced in S2 cells and the cell membrane fraction (CMF) blotted with anti V5 antibody. FIG. 2B is a graph showing a response assay for IGRP-CMF T cell hybridomas (clone 1-76-54).

Figure 9A:
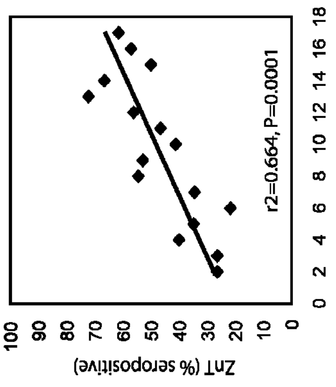
Figure 9B:
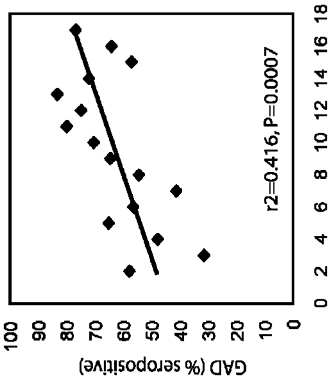
Figure 9C:
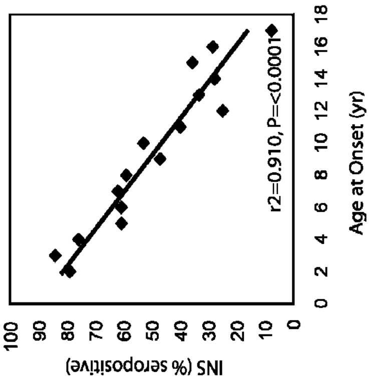
Figure 9D:
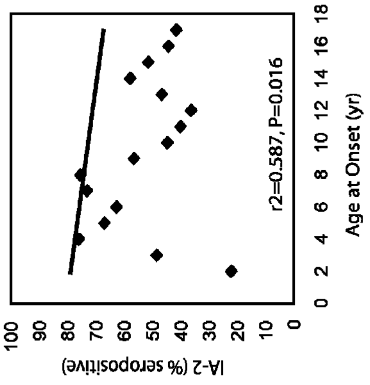

FIGS. 9A-9D is a series of graphs showing the expression of autoantibodies at disease onset relative to age (FIG. 9A=ZnT8; FIG. 9B=GAD; FIG. 9C=Insulin; FIG. 9D=IA2).

Figures 10A, 10B:
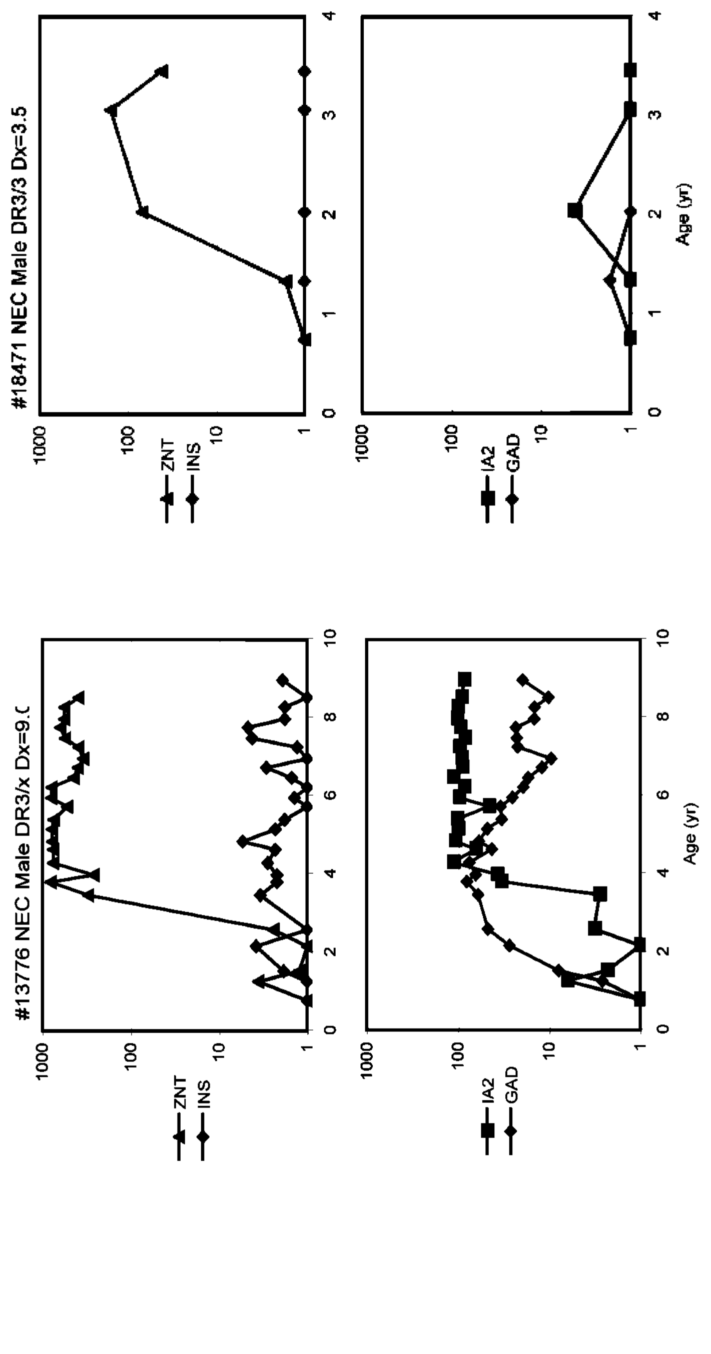

FIGS. 10A and 10B are graphs illustrating the use of ZnT8 autoantibodies as a T1D predictive marker in two different patients, represented in FIGS. 10A and 10B, respectively.

FIG. 11 is a table showing the diabetic autoantibody status of T1D patients at disease onset.

Figure 12A:
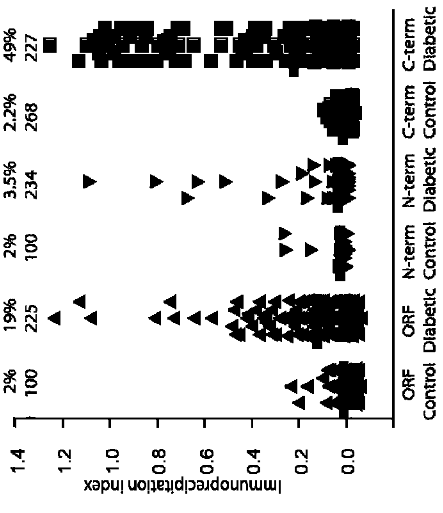
Figure 12B:
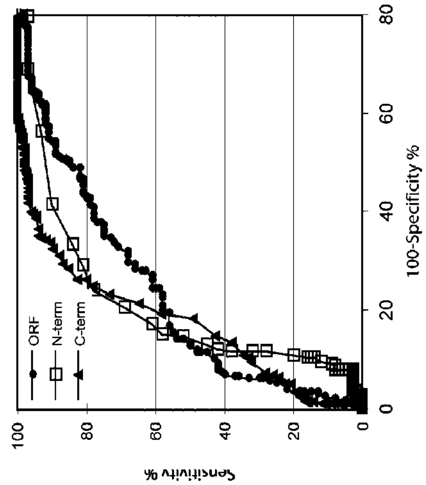

FIGS. 12A and 12B are graphs showing receiver operator characteristics of the ZnT8 antibody assays (FIG. 12A shows the immunoprecipitation index, and FIG. 12B shows sensitivity).

Figure 13:
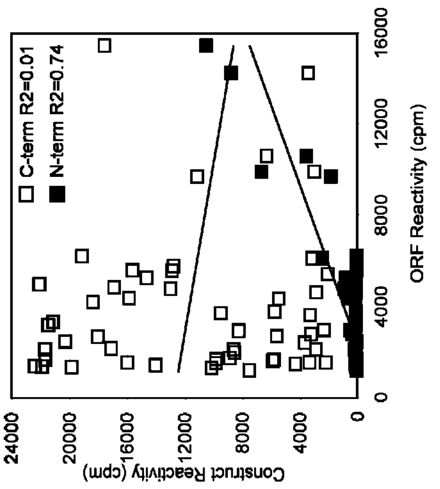

FIG. 13 is a graph showing relationship between reactivity to ZnT8ORF, C-term and N-term.

Figure 14B:
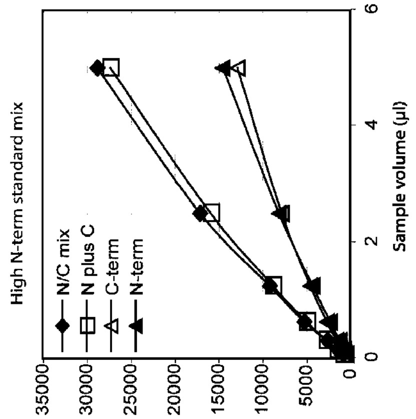
Figure 14A:
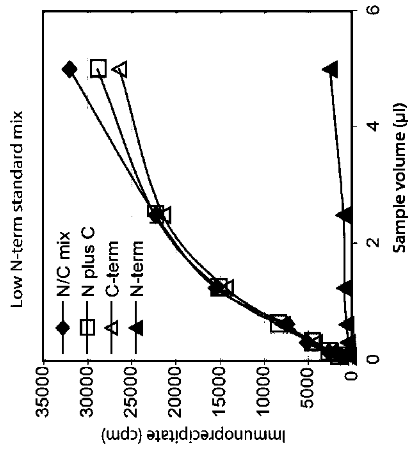

FIGS. 14A and 14B show results of an experiment investigating whether the N-term and C-term of ZnT8 can interact to generate a new epitope; the experiment was performed with 2 pools of diabetic serum that were used as standards in the immunoprecipitation assays, the first selected on the basis of a strong response to a C-term probe (FIG. 14A), the second based on N-terminal reactivity (FIG. 14B).

FIG. 15A shows the aligned sequences of murine Slc30A8 (top; shown are positions 267-367 of SEQ ID NO:4), human Slc30A8 (middle; shown are positions 268 to 369 of SEQ ID NO:2) and murine Slc30A3 (bottom; sequence is SEQ ID NO:25).

FIG. 15B is a graph showing the effect of modifications in the C-terminal probes with respect to autoantibody reactivity (sequence referenced to show restriction sites is positions 336-369 of SEQ ID NO:2)

FIG. 15C is a graph showing the effects of C-term probes with point mutations in charged residues (K340, H345 and E352) with respect to autoantibody reactivity.

FIG. 16 shows residues in the C-term of ZnT8 that are critical for autoreactivity.

Figure 17:
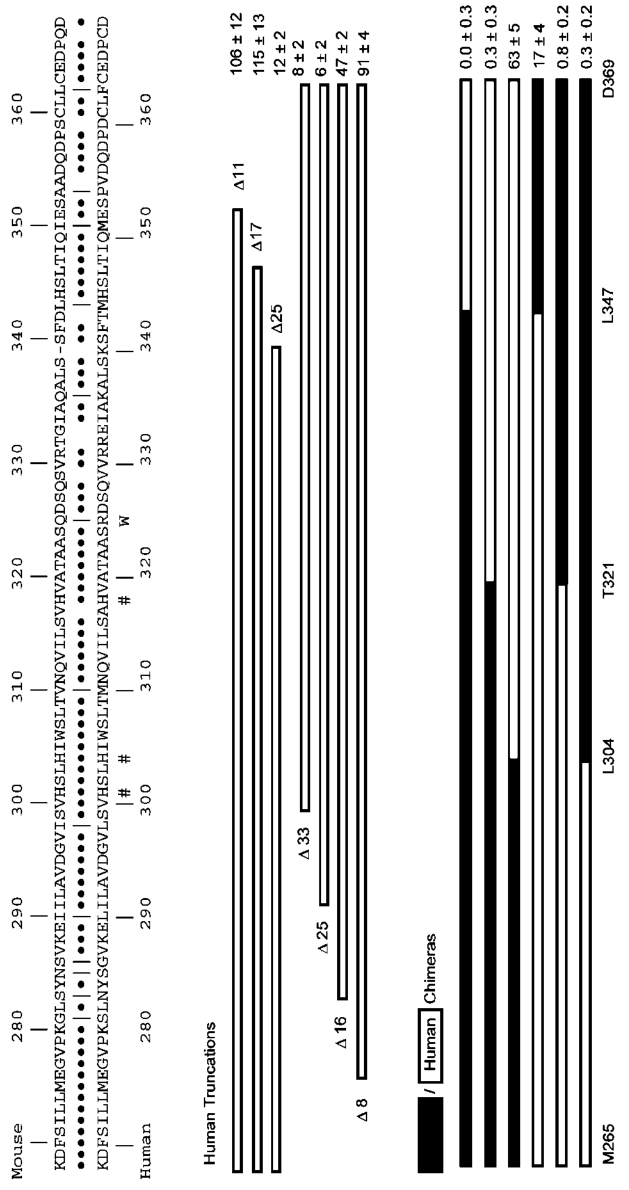

FIG. 17 shows epitope mapping using deletion mutants and mouse/human chimeras. The mouse ZnT8 sequence shown is positions 267-367 of SEQ ID NO:4; the human ZnT8 sequence shown is positions 268-369 of SEQ ID NO:2.

Figure 18:
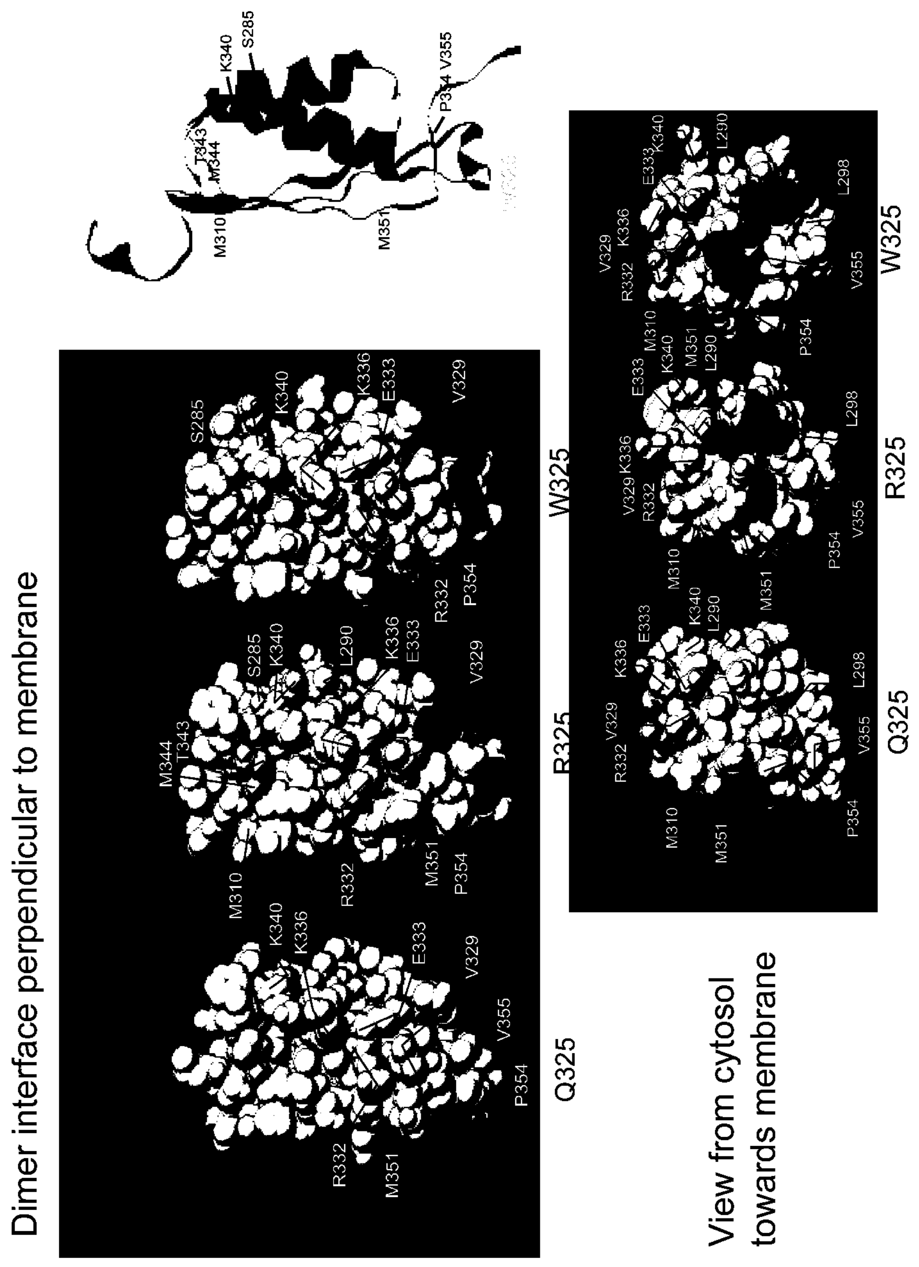

FIG. 18 shows a molecular model used to direct mutagenesis studies.

FIG. 19 shows the conservation of ZnT8 residues in the regions targeted by T1D autoantibodies (Mse N-term sequence is positions 1-74 of SEQ ID NO:4; Hum N-term sequence is positions 1-75 of SEQ ID NO:2; Xen N-term sequence is SEQ ID NO:38; Mse C-term sequence is positions 267-367 of SEQ ID NO:4; Hum C-term sequence is positions 268-369 of SEQ ID NO:2; Xen C-term sequence is SEQ ID NO:39).

FIG. 20 shows sequence homology between human Slc30A family members.

Figures 21A, 21B, 21C:
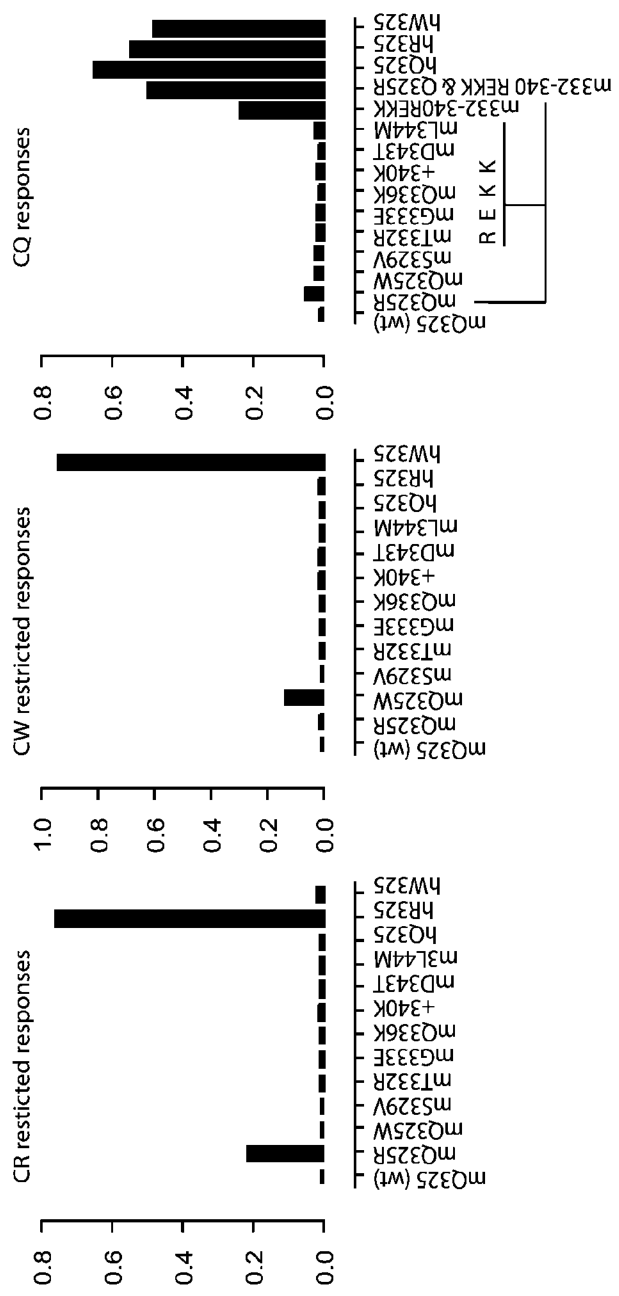

FIGS. 21A-21C show site-directed mutagenesis of mouse ZnT8 identifies major epitopes in the structure with respect to CR-restricted autoantibody responses (FIG. 21A), CW-restricted autoantibody responses (FIG. 21B) and CQ autoantibody responses (FIG. 21C).

FIGS. 22A-22D show that multisite mutation of mouse ZnT8 recapitulates human ZnT8 reactivity (FIG. 22A=mCArg probe with hCArg reactive sera; FIG. 22B=mCArg (Arg Glu Lys Lys) with hCArg reactive sera; FIG. 22C=mCTrp probe with hCTrp reactive sera; FIG. 22D=mCArg (Arg Glu Lys Lys) probe with hCTrp reactive sera).

Figures 23A, 23B, 23C, 23D:
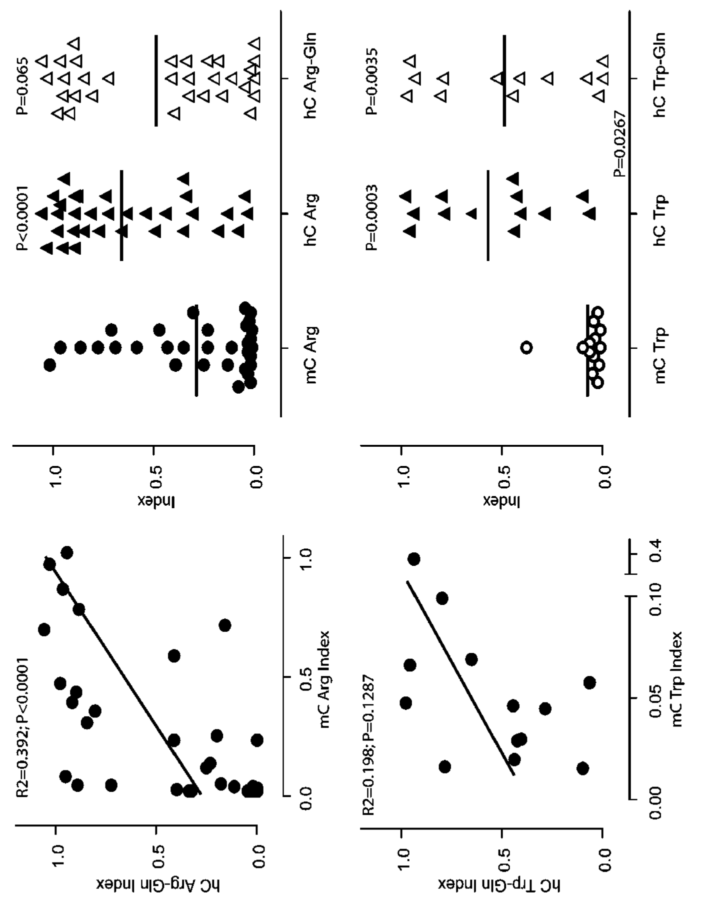

FIGS. 23A-23D show the relationship between levels of antibodies detected by human polymorphic probes and mouse site-directed mutants (FIG. 23A shows the hC Arg-Gln index versus mC Arg index; FIG. 23B shows the mCArg, hCArg, and hC Arg-Gln indices; FIG. 23C shows the mC Trp index versus the hC Trp-Gln index; FIG. 23D shows mCTrp, hCTrp and hC Trp-Gln indices).

Figures 24A, 24B, 24C, 24D:
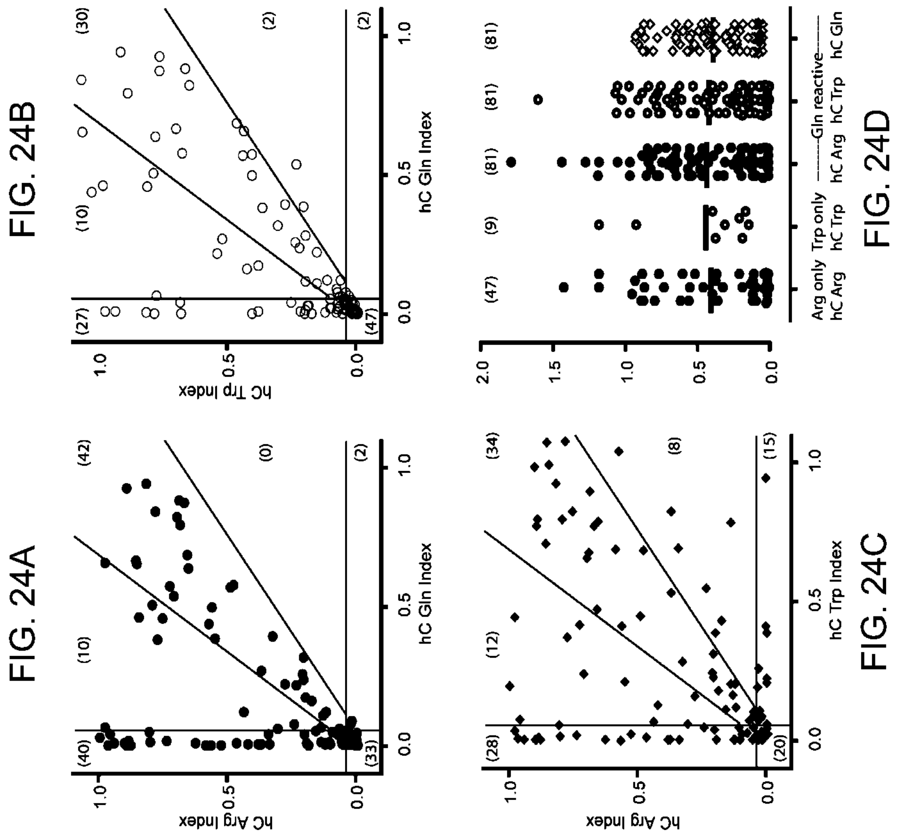

FIGS. 24A-24D show the relationship between Slc30A8 aa325 polymorphism and ZnT8A FIG. 24D shows the level and frequency of the response segregated on the basis of the response to individual probes or probe combinations. FIG. 24C shows the relationship between the responses to the common Arg and Trp variants and is divided in 5 sectors based on a 95th percentile cutoff for Trp (vertical) and Arg (horizontal) only responses and diagonals representing the boundaries equivalent responses ±3SD to both probes assuming a 15% CV in the assay. FIGS. 24A and 24B uses the same stratification in examining the relationship between the responses to the Gln probe and the Arg and Trp probes.

FIG. 25 shows the prevalence of ZnT8A relative to the genotype encoding aa325.

Figure 26:
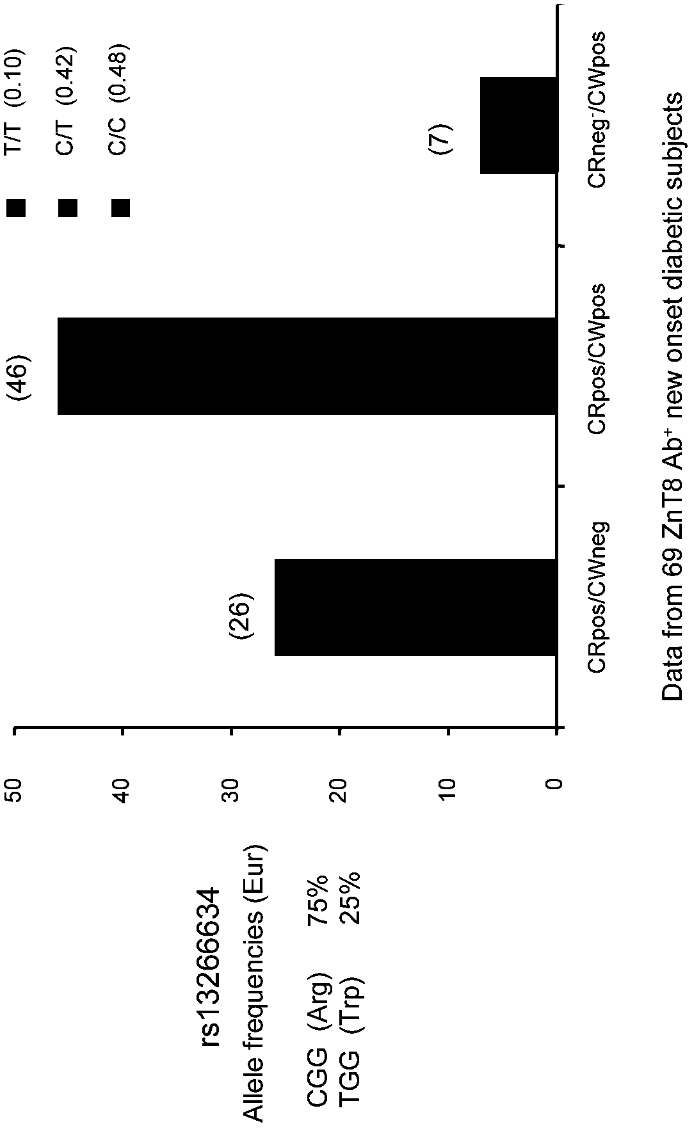

FIG. 26 shows the correlation between genotype and reactivity to the hCR and hCW probes.

Figure 27:
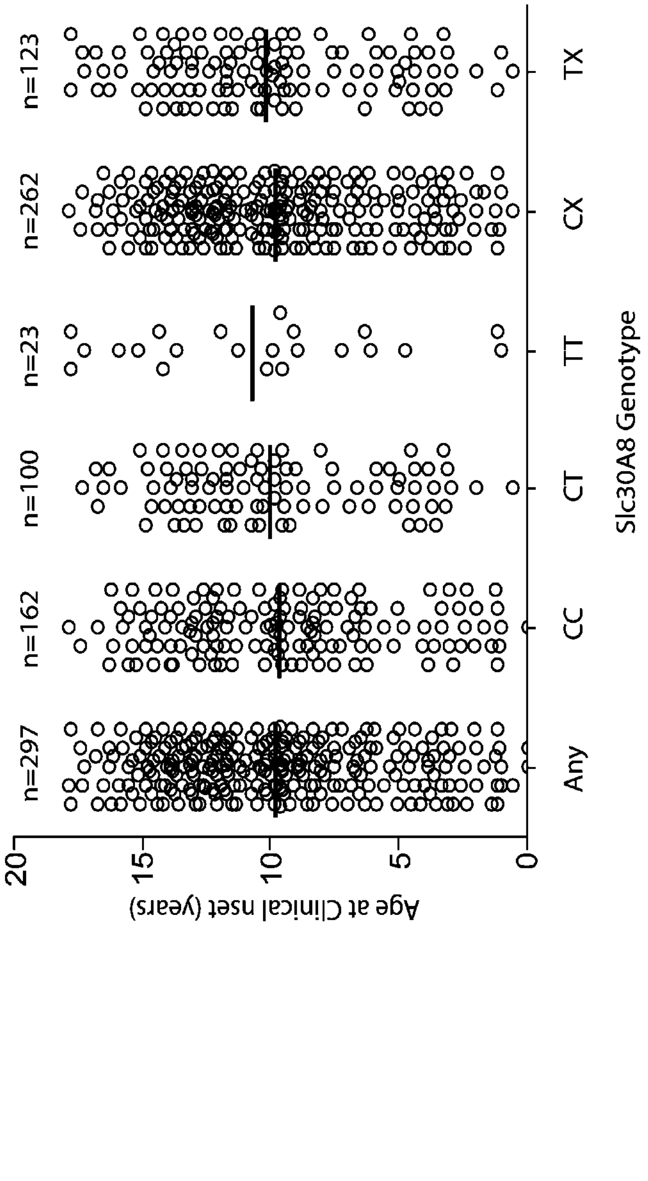

FIG. 27 shows Slc30A8 genotype in relation to age of diabetes onset.

Figure 28A:
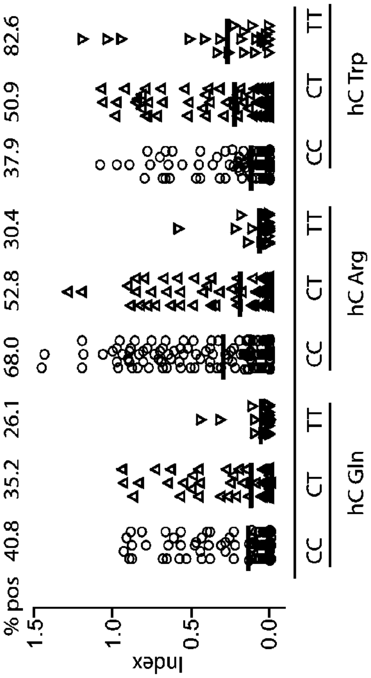
Figure 28B:
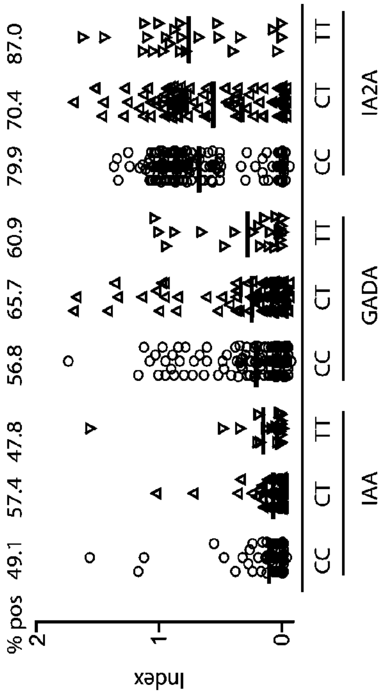

FIGS. 28A-B show Slc30A8 genotype versus antibody levels (FIG. 28A shows the level of Slc30A8 autoantibody reactivity relative to genotype; FIG. 28B shows the level of other autoantibody reactivity relative to genotype).

Figure 29:
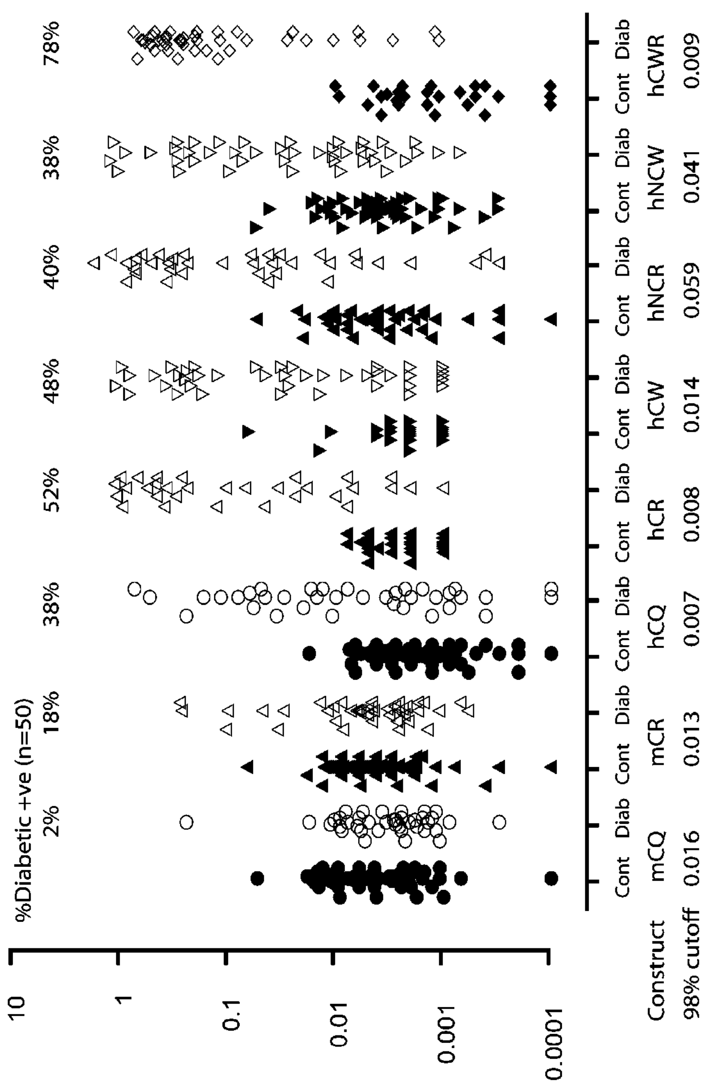

FIG. 29 shows a summary of current ZnT8 assays.

Figure 30:
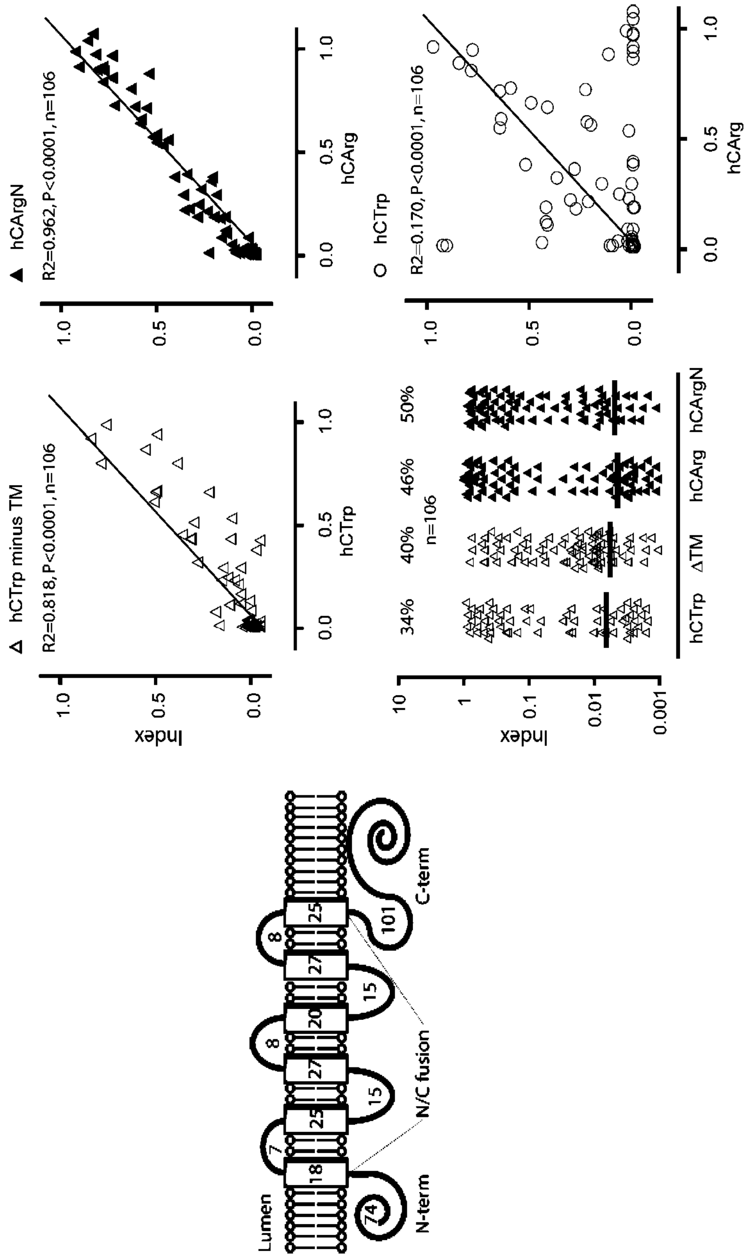

FIG. 30 shows autoreactivity to different ZnT8 constructs combining N-term, C-term, luminal loops, cytosolic loops and polymorphic residues.

Figures 31A, 31B, 31C, 31D, 31E, 31F:
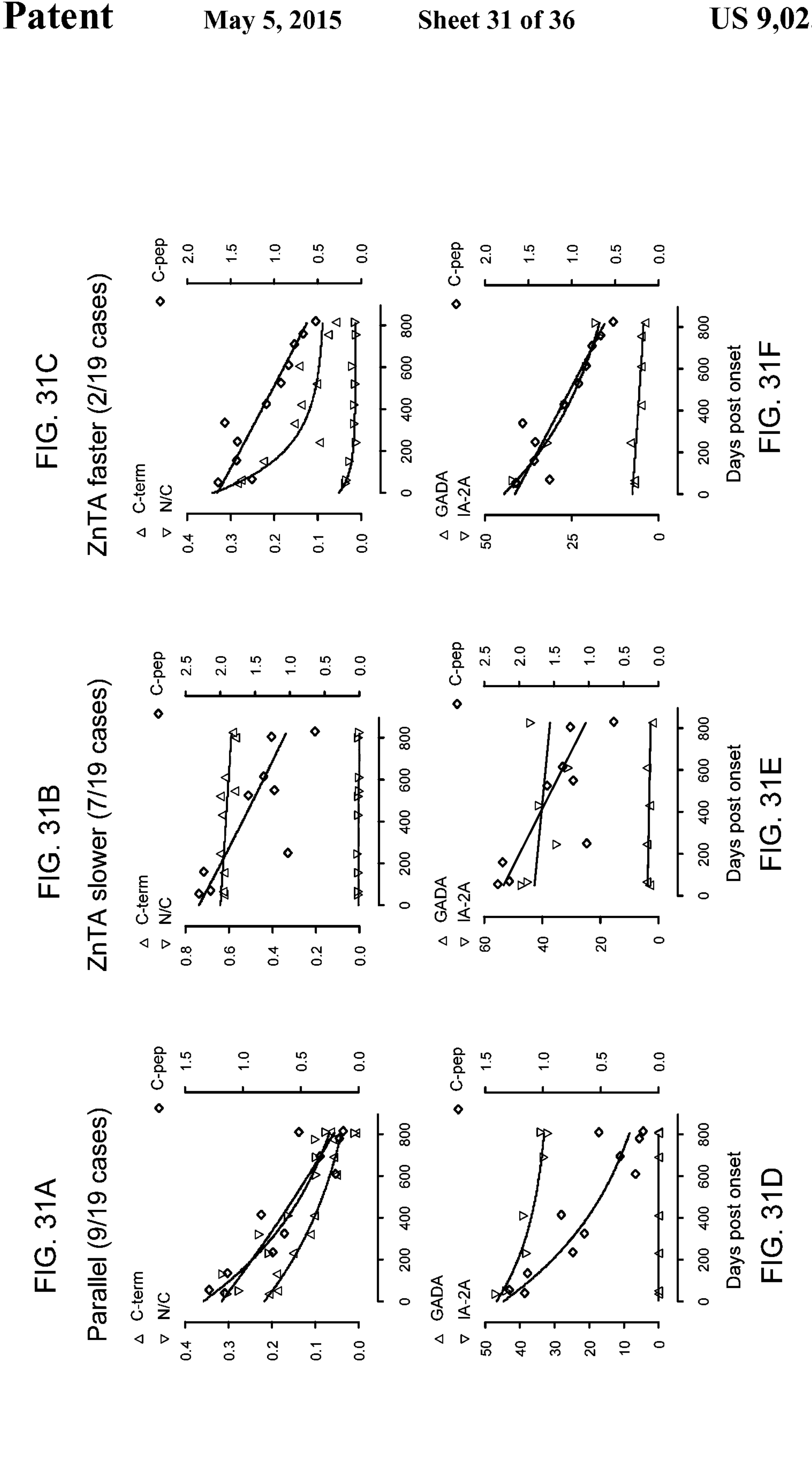

FIGS. 31A-31F show antibody versus C-peptide 0-2 yr post onset (FIGS. 31A-C versus C-peptide; FIGS. 31D-F versus GADA and IA-2A).

Figure 32:
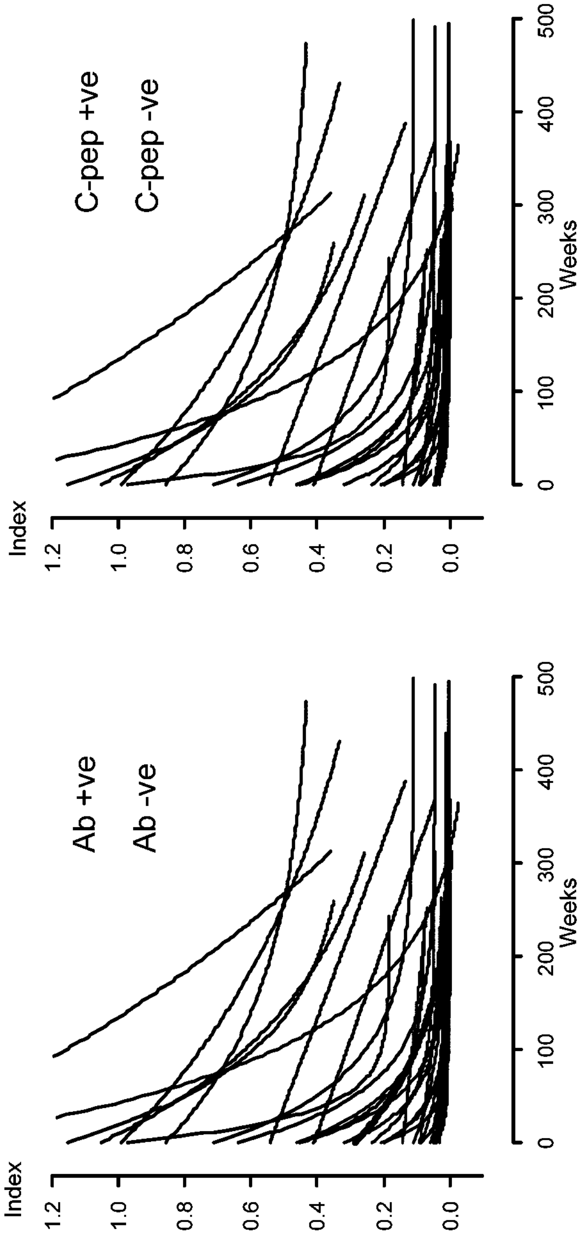

FIG. 32 shows ZnT8A and C-peptide levels 5-10 yr post onset.

Figure 33B:
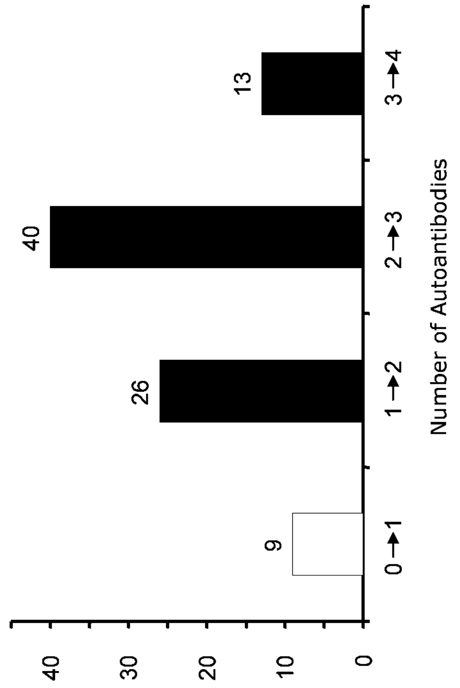
Figure 33A:
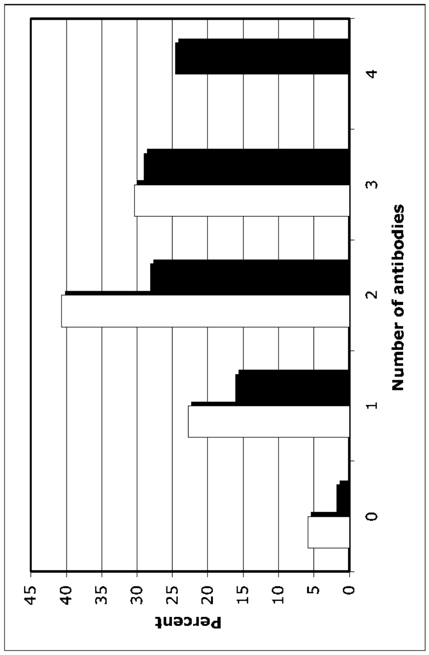

FIG. 33A illustrates the concept as the change in detection rate (black with ZnT8; white without).

FIG. 33B shows the differential effect of adding the ZnT8 antibody measurement.

Figure 34:
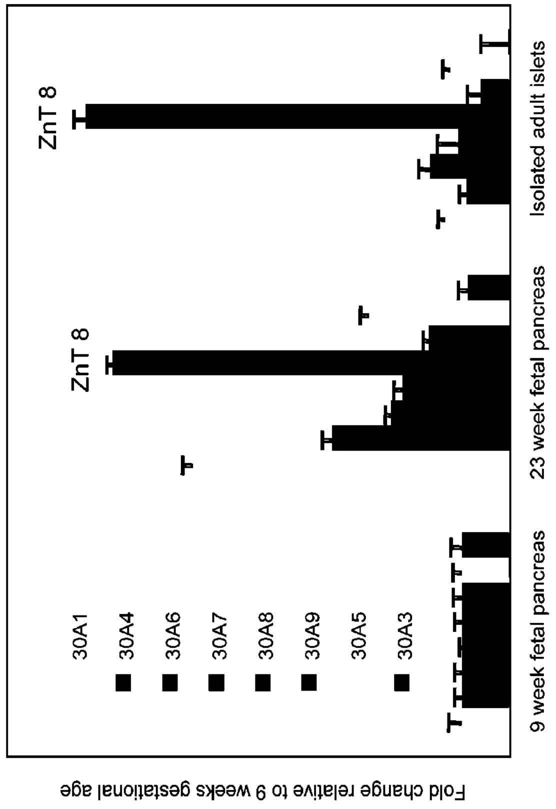

FIG. 34 is a graph illustrating that real time PCR of human fetal pancreas shows high islet specificity.

Figure 35:
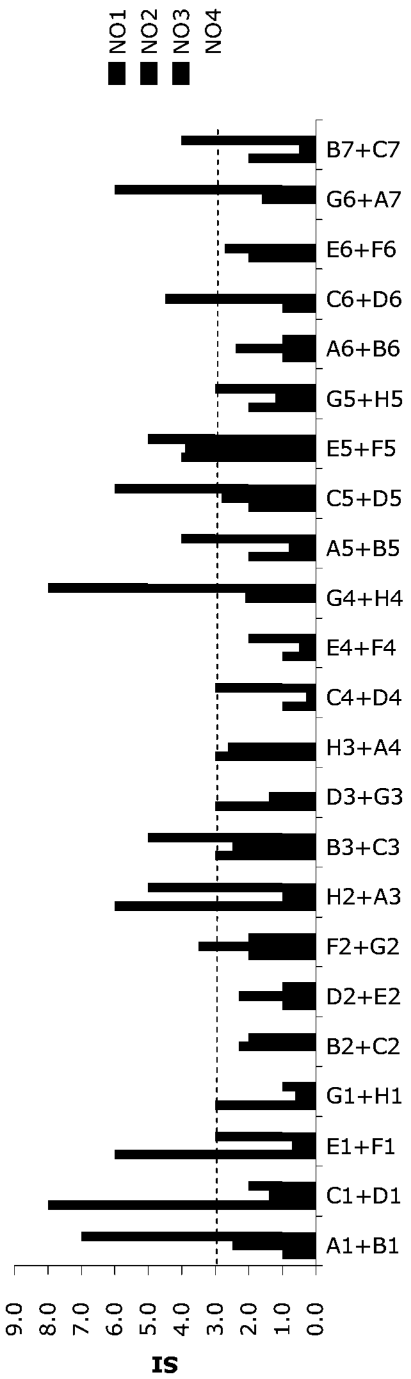

FIG. 35 shows that newly diagnosed T1D patients show peripheral T-cell responses to ZnT8 synthetic peptides.

Figure 36:
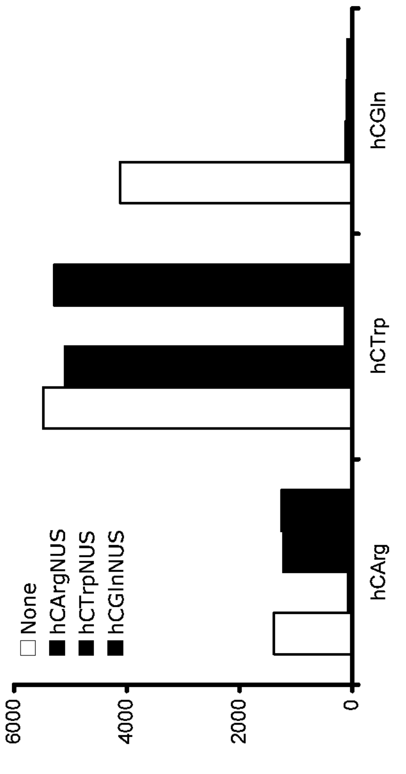

FIG. 36 is a graph showing autoantibody presadsorption experiments demonstrating the utility of recombinant proteins to discriminate between different ZnT8 epitopes.

DETAILED DESCRIPTION OF THE INVENTION

The present invention generally relates to the identification of autoantigen targets, and particularly, autoantigen targets in type I autoimmune diabetes (T1D), and more particularly, the protein ZnT8 as a novel autoantigen, upon which therapeutic, diagnostic, and prognostic tools and methods are based and described herein. The invention also relates to the identification of genetic variation in ZnT8 that is described herein as an important player in the initiation of the disease process and the progression of autoimmunity to clinical diabetes. These findings have allowed the inventors to provide new diagnostic tools that can be used to refine the prognostic evaluation of the course of the disease and to monitor the effectiveness of therapeutic interventions in the preclinical phase of the disease. The molecule itself, derived peptides, peptide analogs and secondary immune reagents also serve as the basis of therapeutic interventions to prevent the onset or progression of autoimmunity to clinical disease. The ability to determine the genotype of an individual as soon as one is born provides a distinct advantage to implementing therapeutic measures, since prevention of the emergence is likely to be easier than reversal of the autoimmune process once it is established.

Previously, as discussed above, insulin was defined as a candidate gene based on its tissue association, GAD65 and IA-2 from the ability of patient sera to immunoprecipitate proteins from radiolabelled islets (64-66), and IGRP as a peptide bound to MHC H-2 $K^d$ that stimulated a T-cell clone derived from a spontaneously diabetic mouse. The inventors have asked the question of whether one can develop a more systematic approach to the identification of target autoantigens based upon what is now understood of the cellular and molecular biology of autoantigens, and the availability of tools to study and analyze genome-wide expression in different tissue by microarray analysis. The objective was to create a list of candidate genes that would include diabetes autoantigens of major importance which may potentially number upwards of 50 proteins from among the 15,000 or so gene transcripts expressed in the β-cell. Robust assays can then be used to detect cellular and humoral immune responses to such molecules. The results of this research are described below, with particular emphasis on the discovery of a novel target autoantigen, namely ZnT8.

More specifically, the structural biology of antigen presentation and T-cell recognition provided relatively few clues to identification of novel T1D autoantigens, since both MHC and T-cell receptor molecules have broad ranges of peptide binding specificities and relatively low affinities. It has proven difficult to identify native epitopes even when detailed knowledge of the binding properties of mimotope peptides is known, simply because the number of contact residues is small and conservative amino acid substitutions are readily accepted. The present inventors describe herein the development of a knowledge-based algorithm to identify candidate autoantigens on a genome wide basis. A number of primary and secondary attributes of an "ideal" autoantigen are initially assumed based on empirical information and weighted accordingly. The conformity of the antigen to each of the ideal attributes is weighted to derive an "autoantigenic score" and hence an ordered list of best candidates. A meta-analysis based on gene ontology functions and information such as gene location is then considered before embarking on an evaluation of a shortlist of candidates based upon spontaneous and primed cell-mediated autoimmune responses in NOD mice and humoral autoreactivity determined in both NOD mice and human sera. The microarray data that underpins this approach has largely been obtained. Accordingly, candidate antigens are first screened by serological analyses in human subjects and then HLA-DR3, -DR4, DQ2- and -DQ8 HLA A2 and other class I HLA diabetes susceptibility alleles in transgenic mice are screened for cell-mediated immune responses to the candidate antigens.

Using this approach, the present inventors have identified Zinc transporter protein 8 (ZnT8, also known as Slc30A8) as a new autoantigen target for prognostic, diagnostic and therapeutic methods associated with T1D. ZnT8 is a protein that appears to be confined to insulin-producing β cells of the islet in man and mice. The present inventors have demonstrated that ZnT8 is a target for autoantibodies in human subjects that develop T1D, and have identified polymorphic variants of ZnT8 as genetic markers of type 1 diabetes susceptibility, autoimmune status, autoantibody specificity and disease progression and severity. Autoantibodies to ZnT8 appear before the development of clinical disease and are believed to be a novel marker for incipient diabetes.

In addition, the inventors have discovered that the ZnT8 autoantibodies target two different regions of the molecule, and that one of these regions incorporates one of 3 different amino acids that play a crucial role in determining both the specificity and the magnitude of the immune response. Determination of the genotype of an individual using a single nucleotide polymorphism analysis at any time prior to the development of autoimmunity and diabetes provides information regarding which variant amino acid is encoded, and can therefore be used in making clinical decision regarding treatment and care. In addition, the present invention permits the precise analysis of the specificity of the autoantibodies that are directed at ZnT8, and further classification of the antibodies with respect to which of the variant forms of ZnT8 are targeted by the immune system. Currently, three major forms that depend on the identity of the variant amino acid at position 325 in the molecule (Arg, Trp or Gln), which are referred to herein as "isoepitopes", and a fourth epitope that incorporates conserved amino acids (aa325 independent), are recognized. The response of the individual can be categorized as being one of 8 different responses: (1) none; (2) Arg325-restricted; (3) Trp325-restricted; (4) Gln325-restricted; (5) Arg325- and Trp325-restricted; (6) Arg325- and Gln325-restricted; (7) Trp325- and Gln325-restricted; and (8) amino acid 325-independent. Such stratification of the autoantibody response is proposed herein to provide information about the disease progression and will be essential in determining how to treat T1Dautoimmunity with antigen-specific therapeutic agents.

More specifically, the inventors have shown that:

60% of new onset TID patients are positive for autoantibodies to ZnT8;

20-30% of T1D patients are positive for autoantibodies to ZnT8 who are negative for other autoantibodies measured by biochemical (GAD, Ins and IA2 autoantibodies) or histological means (islet cytoplasmic autoantibodies);

Identification of autoantibodies to ZnT8 changes 10% of T1D patients from low risk (1 Above) to high risk category (2 Above);

In a single assay format with GAD, the anti-ZnT8 assay detects 90% of new onset TID patients;

The present invention enables large scale screening of patients;

ZnT8 autoantibodies target two different regions of the molecule (N-terminus and C-terminus), the latter of which incorporates one of 3 different amino acids that play a crucial role in determining both the quality and the magnitude of the immune response;

Autoantibodies directed at the sites identified above match the sequence that the gene encodes, are thus truly self-reactive, and the alleles are present in high (75%), medium (25%) and low (1%) frequency and show significant variation between racial groups;

Young children who develop diabetes before the age of 3 have a higher than expected frequency of the CC (homozygous for Arg325 genotype) of ZnT8 (75% vs 55%) and a lower frequency of the CT genotype (heterozygous for Arg325 and Trp 325 genotype) of ZnT8 (35% vs 40%). Older children show a genotype frequency similar to that reported in the normal population. Accordingly, the CC genotype may be considered to be a risk factor for diabetes.

Prior to the present invention, a partial nucleotide sequence encoding a portion of ZnT8 was identified and reported in a publication aimed at identifying molecules associated specifically with the pancreatic beta cell, as an mRNA that was more highly expressed in pancreatic beta cells than in alpha cells, liver or kidney (Neophytou et al., 1996, *Diabetes* 45: 127-133). Two cloned partial nucleotide sequences were deposited in GENBANK® under the Accession numbers Z47772 (clone 23) and Z47779 (clone 41). However, this publication did not identify a full length nucleotide or amino acid sequence for ZnT8, nor does this publication identify or demonstrate the partial sequences as encoding a potential autoantigen.

The entire ZnT8 molecule was originally cloned in 2004 by a group in Switzerland that works principally on heavy metal ion transport proteins (see Chimienti et al., *Biometals* 2005 August; 18(4):313-7; Chimienti et al., *Diabetes* 2004 September; 53(9):2330-7; and Seve et al., *BMC Genomics* 2004 May 23; 5(1):32, each of which is incorporated herein by reference in its entirety). From a bioinformatics approach and immunohistochemistry, Chimienti et al. observed that the molecule is expressed in the pancreatic islet, and they report its association with the insulin secretory granule. Furthermore, Chimienti et al. teach that ZnT8 leads to zinc accumulation in intracellular vesicles when overexpressed in HeLa cells, and suggest that ZnT8 is a ZnT involved in the translocation of the cytoplasmic zinc into intracellular vesicles. However, there is no mention in these reports of ZnT8 being a potential autoantigen and accordingly, no mention of its use in diagnostic or therapeutic approaches such as those described herein.

The recognition by the present inventors of the key role of ZnT8 as an autoantigen in type 1 diabetes stems from a series of recent experiments performed in the inventors' laboratory that specifically addressed the question whether ZnT8 was a target of humoral autoreactivity in new-onset type 1 diabetic patients. The initial studies performed by the inventors indicated that around 10% of patients showed modest autoreactivity to ZnT8 (see Examples). Further development of the assay using a COOH terminal (C-term) fragment of the molecule in place of the full length ZnT8 (described below) markedly increased the sensitivity of the assay, such that up to 70% of T1D subjects tested positive at the onset of disease versus less than 1% of matched controls. Such sensitivity is as good, or better than the currently used assays for humoral autoreactivity in T1D subjects based on the well-known molecules: insulin, glutamic acid decarboxylase (GAD65) and IA-2 (PTrN). The inventors have also demonstrated that ZnT8 is an independent disease marker and as such, complements and extends the sensitivity of antibody-based assays. Through the examination of a series of samples collected over 10 years, it was shown that antibodies to ZnT8 appear later in the development of prediabetes than other antibodies, and it may thus indicate the final destructive phase of insulitis and accordingly, a marker of incipient clinical disease.

In addition, the inventors have discovered that ZnT8 autoantibodies target two different regions of the molecule, and that one of these regions incorporates one of 3 different amino acids that play a crucial role in determining both the quality and the magnitude of the immune response. Since the variant amino acid sequence is determined by the nucleotide sequence of the genome, it is therefore possible to determine which variant amino acid is encoded. The inventors have demonstrated for the first time that autoantibodies directed at this site match the sequence that the gene encodes and thus are truly self-reactive. The gene shows 3 known alleles which are present in high (75%), medium (25%) and low (1%) frequency and show significant variation between racial groups. This has implications in terms of how to diagnose autoimmunity and how to direct therapeutic measures, since it may be beneficial or deleterious to direct to the correct (self) or wrong (non-self) encoded sequence depending on the desired outcome. For example, the object of immune therapy may be the induction of immune tolerance, or conversely, marshalling the immune system through respectively engaging or deleting elements of immune elements, such as destructive effector T-cells or protective regulatory T-cells.

Prior to the present invention, there was no reason to suspect a priori that ZnT8 could be an autoantigen recognized either by antibodies or the cellular arm of the immune system. Indeed, to the best of the present inventors' knowledge, ZnT8 has not been investigated in the context of autoimmune diabetes and there are no other published data on the molecule in an immunological context. As discussed above, there are literature reports on the use of autoantigens as diagnostic and therapeutic agents in other autoimmune diseases and in the context of diabetes. However, these are directed to molecules such as insulin, glutamate decarboxylase (GAD65), IA2, phogrin and heat shock protein 60, which are unrelated to ZnT8 from a structural, cell biological and immunological standpoint.

Moreover, while identification of single amino acid differences in a protein or posttranslational modification of a single amino acid by, e.g., phosphorylation or citrullination, is not unprecedented, there is no reason to suspect that such a change would be a specific determinant of autoantibody specificity as the present inventors have shown. Indeed, single nucleotide polymorphism (SNP) numbers rs13266634 and rs16889462, that encode non-synonymous changes in the coding sequence of human ZnT8 are published in the National Center for Biotechnology Information (NCBI) single nucleotide polymorphism database. This SNP encodes an alternative Arg or Trp at amino acid 325 in ZnT8 (SEQ ID NO:2), which coincides with a polymorphic variant identified in the present inventors' studies. However, no association of this SNP with type 1 diabetes (TID) has previously been identified, to the best of the present inventors' knowledge. A genome wide association study identified ZnT8 as containing a number of SNPs that were associated with type 2 diabetes, including the above referenced rs13266634 (Sladek et al., 2007, *Nature.* 2007 Feb. 22; 445(7130):881-5. Epub 2007 Feb. 11), and an online report of association of ZnT8 polymorphism with beta cell function has recently been reported (Staiger et al., 2007, *PLoS ONE.* 2007 Sep. 5; 2 (9):e832). However, type 2 diabetes is not an autoimmune disease, and no association of this SNP with type 1 diabetes has been previously identified, to the best of the present inventors' knowledge. Moreover, Type 2 diabetic patients have not been shown to display ZnT8 autoantibodies.

Polymorphic variants in the sequences of other TID autoantigens, namely GAD65 and IA2, have been identified; however, none of these has been implicated in changes in the autoreactivity of these autoantigens in type 1 diabetes. In IA2 there appears to be alternative splicing of the mRNA that can occur in a tissue specific manner and conceivably results in escape from immune surveillance. However, this does not equate with the type of genetic variation reported herein by the present inventors, namely, a single amino acid change that is associated with specific recognition of the molecule by an autoantibody. Therefore, this discovery by the inventors is unprecedented. The discovery, described herein, that the two forms of ZnT8 encoded by the common polymorphism induce qualitatively different immune responses and consequently take autoantibody determination to a new level. It also indicates that different forms of the molecule can be used to target different components of the immune system to bring about different immunological outcomes.

Accordingly, the present inventors describe herein the use of genes encoding ZnT8, nucleic acid molecules derived therefrom, ZnT8 proteins or fragments thereof encoded by such genes and nucleic acid molecules, as well as homologues of such genes and proteins and related agents (e.g., antibodies, agonists, antagonists), and polymorphic variants of ZnT8, and the use or targeting of such genes, nucleic acids, proteins, homologues, variants and/or related agents, and/or compositions or formulations comprising the same, in the development of a variety of diagnostic and therapeutic tools and assays. Such tools and assays include, but are not limited to:

1. Assays in humans and experimental animals for the detection of diabetes related autoimmunity based on antibody responses to ZnT8, specific domains of the molecule, and peptides derived from the protein. Such assays are provided in the format of radioimmunoprecipitation assays, ELISAs, time resolved fluorescence and luminescence assays, although other formats are also encompassed by the invention. Such assays can be used to:

a. predict susceptibility to the development of type 1 diabetes in individuals and groups of subjects;

b. monitor the progression of autoimmunity from an initial benign autoreactivity to destructive insulitis; and/or c. monitor the efficacy of treatments aimed at preventing or ameliorating autoimmunity in the prediabetic state. Such treatments could be based on a range of potential immunosuppressive agents including those designed on the ZnT8 molecule itself.

2. Epitope-specific autoantibody assays in humans and experimental animals for the detection of diabetes related autoimmunity based on probes directed at the 3 variant forms of ZnT8, and the use of recombinant proteins that encode the 3 forms as competing or blocking agents. Such assays could be in the format of radioimmunoprecipitation assays, ELISAs, time resolved fluorescence and luminescence assays, although other formats are also encompassed by the invention. Such assays can be used to:

a. generally predict susceptibility to the development of type 1 diabetes in individuals and groups of subjects from the prevalence of antibodies, the level of response, the titer of the antibodies or the avidity, affinity or clonality of the response, as in (1) above;

b. determine which of the 3 epitopes are targeted in a particular individual and changes in the specificity of the response in the course of disease and treatment as a measure of the progress and response to therapy;

c. determine the likely target epitope specificity of the immune response by a combination of genotyping, and thus determine in advance the best modality of treatment; and/or d. monitor the efficacy of treatments aimed at preventing or ameliorating autoimmunity in the prediabetic state. Such treatments could be based on a range of potential immunosuppressive agents including those designed on the ZnT8 molecule itself.

3. Assays in humans and experimental animals for the detection of diabetes-related autoimmunity based on the reactivity of T-lymphocytes to the protein and derived peptides using lymphocyte proliferative responses, MHC class I and II tetramer reagents and ELISPOT assays.

4. Labeled antibodies to the antigen, and assays based upon competition of the autoantibodies with the labeled antibodies as means of assay.

5. Antiidiopathic antibodies as a mimic for the ligand.

6. Therapeutics based on antigen, antibodies bound to the antigen, and/or antigen or antibodies bound to cells.

7. Reagents based on ZnT8 for further diagnostic purposes. These include polyclonal and monoclonal antibodies to the molecule, peptides, peptide mimics and altered peptides that when administered in vivo, could affect the course of disease, or which could be used ex vivo to stimulate T-cells from an autoimmune subject to adopt a different phenotype and thus become more toleragenic.

8. Antigen-specific immunotherapeutic reagents based on the cognate peptide epitope or altered peptide bound to its MHC molecule together with an agent that is toxic to T-cells that would engage with the peptide/MHC complex, or a monoclonal antibody that would recognize a antigenic peptide, or a mimic such as a discrete molecule or a molecule complexed to another molecular component such as a peptide/MHC complex or peptide/T-cell receptor complex that would act as an agonist or antagonist of the normal peptide interaction and signaling. Depending on the individual's genotype and the epitope specificity of the prevalent antibodies at the time, the therapeutic agent can be matched to the specificity of the antibody, or mismatched to stimulate an alternate immune response.

9. Use of the ZnT8 molecule as a recombinant protein to alter the response of the immune system in a way that is protective rather than destructive. This involves the use of recombinant protein, chemically or physically modified forms of the protein, peptide sequences derived from the protein, chemically or physically modified peptides and peptide homologues which could be used as a vaccine.

10. Generation of conjugates or combination of effector molecules with the ZnT8 epitope specific peptide or a reagent to (such as a small molecule or antibody) to very specifically target the immune process that sustains the autoimmune reaction. This is based on the concept that, antibodies are the product of specific B cells, that also act as antigen presenting cells to auto reactive T cells, which in turn provide signals to activate and cause the differentiation of the B cell.

11. cDNA constructs based on the human and mouse ZnT8 mRNA including deletions, chimeric constructs, point mutations at single and multiple sites to alter the coding sequence, and the use of such constructs as diagnostic reagents or to study the specificity of the immune response;

12. Epitope-tagged and fusion proteins, including GFP, GST, NUS, and poly His sequences, in vectors for expression of ZnT8 in mammalian cells, yeast and *E. coli*, and the use of such constructs as diagnostic reagents or to study the specificity of the immune response.

13. Adenoviral constructs for transduction and expression of ZnT8 in mammalian cells, including the polymorphic variant and epitope-tagged and reporter protein constructs, and the use of such constructs as diagnostic reagents or to study the specificity of the immune response.

FIG. 20 shows a comparison of the ten variants of the Slc30A gene that are recognized in humans, although one of these (Slc30A9) is probably not a true homologue given its low amino acid sequence identity and similarity (shown in parentheses above). The closest relatives of ZnT8 are Slc30A2, a lysosomal protein, Slc30A3 a protein associated with synaptic vesicles and Slc30A4. Antibodies raised in rabbits to Slc30A8 show some cross-reactivity with Slc30A3, which raises the possibility that reactivity or cross-reactivity might also occur in other human autoimmune diseases, like multiple sclerosis. Conversely, diabetic Slc30A8 autoantibodies to Slc30A8 reactive T-cells might also target other tissues and contribute to complications of diabetes. Accordingly, the tools and methods of the invention are believed to be useful and applicable to autoimmune diseases other than TID, such as, but not limited to, systemic lupus erythematosus, myasthenia gravis, rheumatoid arthritis, multiple sclerosis, celiac disease, autoimmune thyroiditis, Addison's disease, Graves' disease and rheumatic carditis. The method of the invention is applicable to any autoimmune disease in which Slc30A8 (ZnT8) or a homologue is a target or autoantigen (autoantibody or T cell autoantigen).

Moreover, the inventors have shown that individuals with autoantibodies to ZnT8 in some cases show reactivity to the other members of the Slc30A gene family encoding other ZnT transporters. For example, the inventors show some reactivity to ZnT3, which is normally considered a neuron-specific isoform. An important implication of this finding is that such reactivity could have pathological consequences in tissues outside of the pancreas. It is known that diabetes especially type 1 diabetes is associated with peripheral neuropathy, and cross-reactivity of antigens may represent a link between these conditions. Accordingly, the tools and methods of the invention are believed to be useful and applicable to other conditions that are linked by antigen cross-reactivity, including, but not limited to, peripheral neuropathy.

Aspects of the invention demonstrated herein include the following clinical observations:

Prediabetes:

ZnT8 autoantibodies appear early usually, after GADA and IAA along with IA2A

There is no strict hierarchy of appearance and ZnT8 can precede diabetes by 1-12 yr New onset ZnT8 increase in prevalence after 2-3 yr at onset reaching a maximum at 16-18 yr of age of 60-80%

Post onset

ZnT8 fall post onset with half life of 1 year possibly in parallel with loss of β-cell mass as measured by C-peptide.

ZnT8 are less persistent that GAD or IA2.

ZnT8 can persist in the absence of measurable C-peptide and vice versa.

ZnT8 Nucleic Acids, Proteins, Polymorphic Variants, Homologues, Fragments, Antibodies, and Compositions ZnT8 Gene, Structural Information, Nucleic Acid and Amino Acid Sequences In one embodiment, the present invention encompasses the use of a gene encoding ZnT8, as well as nucleic acid molecules derived from or comprising at least a portion of the coding region and/or regulatory region of such gene, and including any polymorphic variant of such gene. The present invention also encompasses the use of any ZnT8 proteins, homologues or fragments thereof, including any polymorphic variant thereof, or agonists or antagonists thereof, including those encoded by the above-referenced genes or nucleic acid molecules. Novel ZnT8 nucleic acid molecules and proteins (including various novel homologues, variants, fragments, fusion proteins, and chimeric proteins of ZnT8), as well as agonists and antagonists thereof, are encompassed by the invention as compositions of matter. The present invention further includes ZnT8 antibodies, antigen-binding fragments thereof, and antigen-binding peptides that are useful in a variety of methods in the present invention.

Zinc transporter protein 8 (ZnT8, also known as Slc30A8) is a 369 amino acid protein encoded by the ZnT8 gene. ZnT8 contains six transmembrane domains and a histidine-rich loop between transmembrane domains IV and V, like the other ZnT proteins (see Chimienti et al., 2004, *Diabetes*, supra, and FIG. 4 presented herein). This protein is solely transcribed in the pancreas and more particularly, is expressed only in the β cells of the islets of Langerhans. As described by Chimienti et al., *ibid*., the ZnT8 gene is located on chromosome 8q24.11, contains eight exons, and spans 37 kb. The cDNA and deduced amino acid sequence of human ZnT-8 protein are provided in Chimienti et al., *ibid*., and this publication shows the gene structure, chromosomal localization, and putative splicing of human ZnT8 (see FIG. 1A of Chimienti et al., ibid.). The cDNA sequence encoding human ZnT8 and the deduced amino acid sequence are reflected in FIG. 1B of Chimienti et al., *ibid*., where the predicted transmembrane domains of ZnT8 are also indicated. FIG. 1C of Chimienti et al., *ibid*., shows a comparison of hsZnT-8, mmZnT-8, and rnZnT-8 amino acid sequences, with identical residues being indicated by black boxes. A nucleic acid sequence encoding human ZnT8 is represented herein by SEQ ID NO:1. SEQ ID NO:1 encodes the human ZnT8 protein, the amino acid sequence of which is represented herein by SEQ ID NO:2. Murine ZnT8 is also known in the art. The nucleic acid sequence encoding murine ZnT8 is represented herein by SEQ ID NO:3. SEQ ID NO:3 encodes the murine ZnT8 protein, the amino acid sequence of which is represented herein by SEQ ID NO:4. The nucleotide sequence encoding human ZnT8 is also described in the National Center for Biotechnology Information (NCBI) database Accession No. NM_173851 (gi: 64762488). The amino acid sequence for human ZnT8 is also found in the NCBI database Accession No. NP_776250 (gi: 64762489). The nucleotide sequences encoding rat ZnT8 is also known. All of the information contained in the database accession numbers and in the publications referenced herein is incorporated herein by reference. Various polymorphic variants, fragments, chimeric proteins, and fusion proteins of these sequences are described elsewhere herein, and are also encompassed by the invention.

Chimienti et al., *ibid*., FIGS. 3A-D, provides further description of the structural analysis of ZnT8, including the predicted membrane-spanning domains of ZnT8, and the location of the histidine-rich domain, which is shared among other members of the ZnT family (see Chimienti et al.). These structural motifs are conserved in rat and mouse ZnT-8. In the human ZnT8 protein, the conserved histidines appear at positions 197, 203 and 205 with respect to SEQ ID NO:2. In mouse, a histidine at position 196 of SEQ ID NO:4 aligns with the human His197, and a histidine at position 204 of SEQ ID NO:4 aligns with the human His205. Therefore, there was an abundance of structural and functional information available at the time of the invention regarding ZnT8 nucleic acid and amino acid sequences.

Homologues, Variants, Fragments and Epitopes of ZnT8 Encompassed by the Invention The present invention also encompasses numerous naturally occurring and synthetically derived variants (homologues) of ZnT8, including nucleotide and amino acid polymorphisms in the gene, proteins encoded by alternate start sites, and various fragments, fusion proteins, and chimeric proteins, and the nucleic acid molecules encoding such fragments, fusion proteins, and chimeric proteins. These polynucleotides and proteins or peptides are useful in a variety of diagnostic, therapeutic and research applications of the invention, as discussed below.

In one embodiment of the present invention, a homologue or variant of a ZnT8 protein useful in any of the methods described herein comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of a wild-type ZnT8 protein, and particularly, the human ZnT8 protein described herein (see discussion above). In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the ZnT8 protein.

Figure 3:
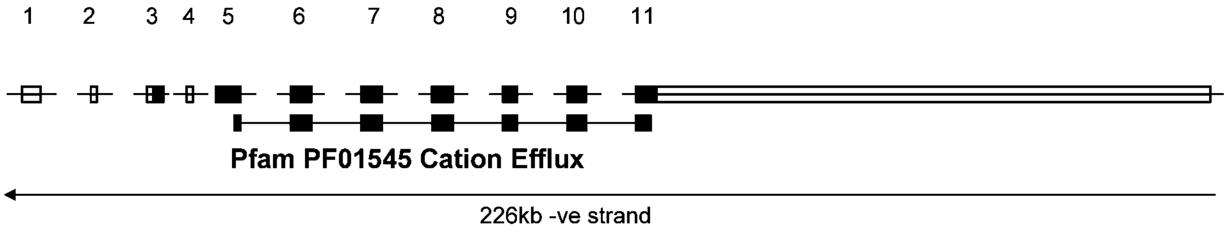
FIG. 3 shows the revised gene structure for ZnT8 based on EST sequence variation and predicted alternate translation products. Referring to the depicted alternative translation products, the “start” sequence of MYHCH corresponds to positions 50-54 of SEQ ID NO:2 and the “start” sequence of MEFLER corresponds to positions 1-6 of SEQ ID NO:2.

The invention also includes various naturally occurring and synthetically derived variants of ZnT8 that are proteins encoded by alternate start sites, as well as fragments (peptides) thereof, fusion proteins, or chimeric proteins thereof that are useful in any of the diagnostic, therapeutic, or research methods described herein. For example, a natural variant of human ZnT8 with an alternate start site is represented herein by SEQ ID NO:5. This protein spans from amino acid position 50 to 367 of SEQ ID NO:2. Referring to FIG. 3, the gene structure shown was deduced by the inventors from alignments of published EST sequences and the gene. It differs however from the 8 exon gene structured that is accepted as "normal". Specifically, around 210 EST sequences were evaluated, and notable splice site variation was identified, which can lead to potential changes in tissue expression, since the 5'UTR is altered. In instances where exon 4 is spliced, the sequence goes out of reading frame and a truncated transcript, typically MEFLERAYLVNDKAAKMYAFTLERRSCK* (SEQ ID NO:6), although another truncated form, wherein position 7 is a threonine instead of an alanine, and where position 27 is an arginine instead of a cysteine, is represented by SEQ ID NO:7 (MEFLERTYLVNDKAAKMYAFTLERRSRK*). It appears that the downstream Met can be used as an alternate start site resulting in the truncation of the NH2 terminus of the sequence. If this occurs in a tissue specific manner, e.g. in thymus and not in pancreas, then a cryptic epitope occurs that might be targeted by the immune system. The present inventors' laboratory has evidence of this occurring and contributing to autoreactivity to other diabetes-related autoantigens, IA-2 and IGRP. The alternative translation product might also be presented to the immune system as a "foreign" peptide epitope. In addition, natural polymorphic variants of the full-length ZnT8 protein have been identified, which include, but are not limited to, a substitution of a histidine for the tyrosine at position 18 of SEQ ID NO:2, a substitution of a valine for the alanine at position 261 of SEQ ID NO:2, and a substitution of a tryptophan or a glutamine for the arginine at position 325 of SEQ ID NO:2. Polymorphic variants of ZnT8, particularly at position 325, are of particular interest in the present invention and are discussed in detail below. Proteins, variants, fragments, chimeric proteins, and fusion proteins comprising such polymorphisms, and the nucleotides that encode them, are encompassed by the invention.

Figure 4A:
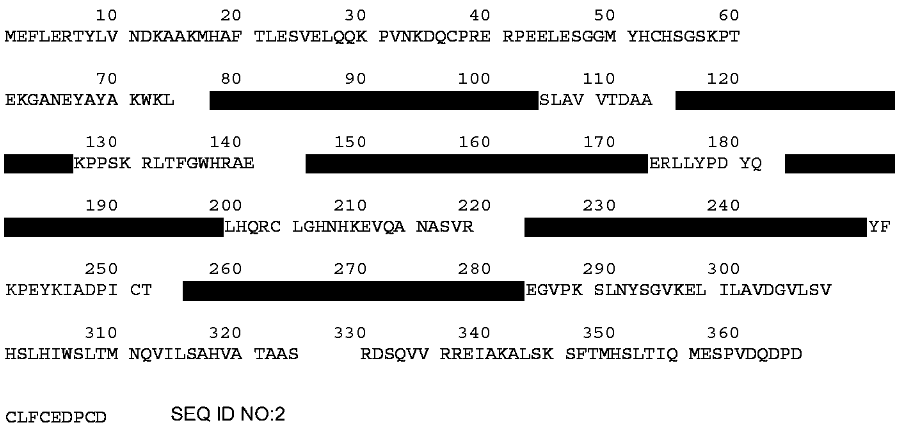
FIG. 4A shows the amino acid sequence of human ZnT8 (SEQ ID NO:2), with predicted transmembrane domains highlighted in darker gray.
Figure 4B:
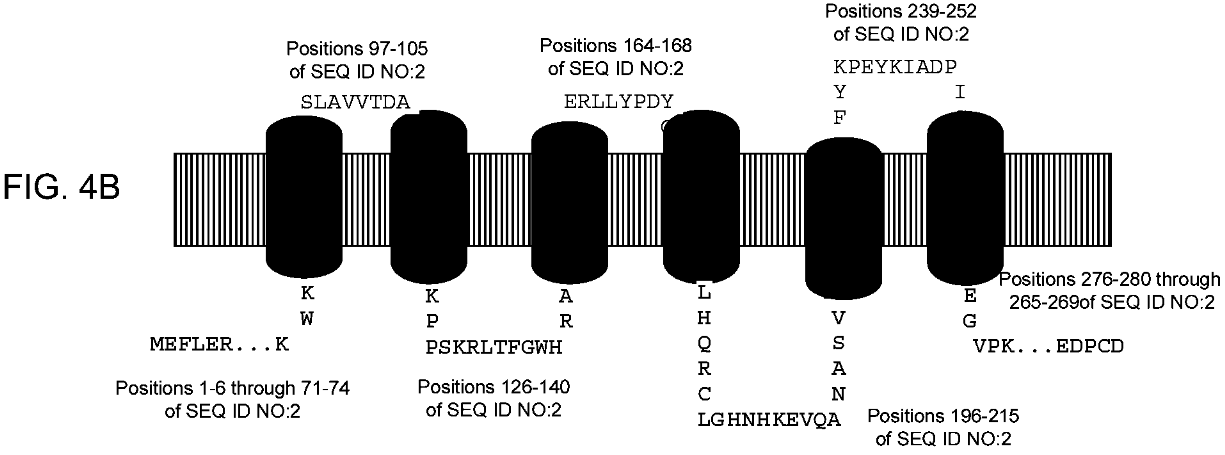
FIG. 4B shows the predicted membrane topology of ZnT8 and the amino acid positions of the loops are shown.

Referring to FIGS. 4A and 4B, The NH2 and COOH termini are predicted to lie on the same side of the membrane. The N-terminus is 74aa long in the case of the reference sequence and 25aa in the case of the isoforms with the alternate start site. The COOH terminus of 94aa incorporates the major humoral immunological determinant in type 1 diabetes. This epitope is cryptic in the full length molecule and lies between aa268 and 358 as shown by the minimal effect on antigenicity caused by removal of the last 15aa. Curiously, this is a region which is strongly conserved among ZnT transporters from different species. Accordingly, it is possible that autoreactivity can be generated against the ZnT8 protein (unique to the pancreatic β-cell) and also by homologous proteins of infectious organisms. A similar relationship has been observed with another diabetes autoantigen IA2 (unpublished work). It is a general principle then one can postulate that autoimmunity in T1D could be triggered by a minor infection with a microorganism with a similar Zn transporter. Equally it might be possible to immunize with the defined epitope of the infectious agent. A second weaker epitope is located in the N-terminus which is not conserved.

The identified epitopes appear to reside inside the cell as is the case of the autoantigens IA2 and GAD65. Referring to FIG. 4B, the short loops at the top side of the figure (encompassing positions represented by positions 97-105; 164-168, and 239-252) would likely be oriented towards the lumen of the cellular elements of the secretory pathway. This potentially would include the endoplasmic reticulum, the Golgi, the insulin secretory granule and ultimately the extracellular space. It is likely that they are exposed on the cell surface during the normal exocytosis of insulin granules during normal secretion or if the cell were damaged in some way. Thus antibodies to peptides representing these loops are encompassed herein for the detection of ZnT8, and it would thus serve as a biomarker which might be used to image the β-cell mass in vivo, to determine the activity of the cell (more secretion equals more exposure) and to monitor the generation of β-cells from other sources such as stem cells, and during normal development. One antibody of the invention is proposed that is raised against the luminal domain 2 sequence of the mouse ZnT8 (positions 163-183 of SEQ ID NO:4, or ERLLYPDYQIQAGIMITVSGC) for cell biological applications. In addition antibodies have been made to the human C-terminus as a fusion protein with glutathione S-transferase (see below). Other antipeptide antibodies to sequences in the N-term and C-term region can be produced using the guidance provided herein. Generation of anti-phosphopeptide antibodies can also be prepared.

There are potential sites of phosphorylation of the molecule in the second intracellular domain and in the C-terminal loop. Phosphorylation of these sites could determine the localization of the molecule in the cell and its activity as a Zn transporter. A new generation of therapeutic agents are targeted at protein kinases and it thus may be possible to modulate the activity of the protein in vivo through drug administration.

The third intracellular loop (depicted as residues 196-215 of SEQ ID NO:2 in FIG. 4B) is rich in histidine residues (positions 197, 203 and 205 of SEQ ID NO:2) which may be important in binding Zn and other heavy metals. This could be part of the mechanism by which the molecule transfer Zn from the cytoplasm to the lumen of membrane enveloped compartments that constitute the secretory pathway.

In one embodiment of the present invention, fragments of ZnT8 are encompassed for use in diagnostic and therapeutic methods, or for the generation of antibodies. According to the present invention, the minimum size of a ZnT8 protein, portion of a protein (e.g. a fragment, portion, domain, etc.), or region or epitope of a protein, is a size sufficient to serve as an epitope or conserved binding surface for the generation of an antibody or as a target in an in vitro assay. In one embodiment, a protein of the present invention is at least about 4, 5, 6, 7 or 8 amino acids in length (e.g., suitable for an antibody epitope or as a detectable peptide in an assay), or at least about 25 amino acids in length, or at least about 50 amino acids in length, or at least about 100 amino acids in length, or at least about 150 amino acids in length, and so on, in any length between 4 amino acids and up to the full length of a ZnT8 protein or portion thereof or longer, in whole integers (e.g., 8, 9, 10, . . . 25, 26, . . . 300, 301, . . . ). Any N-terminal fragment, C-terminal fragment, chimera thereof or deletion fragment of any length is encompassed by this invention, with respect to the ZnT8 protein from any species, with human ZnT8 being preferred, and including any polymorphic forms thereof. Table 1 and FIGS. 15-19, 21 and 25, for example, describe additional information regarding the localization of epitopes and isoepitopes of ZnT8, including the identification of residues in the C-terminus that are critical for autoreactivity. This information allows for the design, production and use of a variety of fragments and homologues of ZnT8 in any of the diagnostic, prognostic and therapeutic methods described herein.

As discussed above, FIGS. 4A and 4B show the predicted transmembrane domains of the ZnT8 protein. These domains pose a problem in the design of assays as they are usually surrounded by lipid and are otherwise very sticky, so the protein either precipitates or doesn't fold. Such regions may be targets for T-cells, and are accordingly encompassed for use in fragments according to the invention, but they are unlikely to be targets for antibodies. The full-length sequence does show reactivity to circulating antibodies and more so in diabetics than controls. However the assay detects only 10-20% of individuals with recent-onset disease. accordingly, the inventors have provided alternative probes, namely the N-terminus, C-terminus and the Zn binding loop probes as set forth below.

A particularly preferred fragment of a ZnT8 protein useful in the present invention is any N-terminal or C-terminal fragment of ZnT8, with C-terminal fragments being particularly preferred. Another preferred fragment of ZnT8 is a mixture or hybrid (chimera) of N- and C-terminal fragments of ZnT8. Particularly preferred fragments of ZnT8 comprise, consist essentially of, or consist of, any C-terminal fragment from about the C-terminal 110 residues to about the C-terminal 8 residues of human ZnT8. Particularly preferred C-terminal fragments include the 101 and 102 C-terminal residues of human ZnT8.

A variety of proteins, variants, chimeric proteins, and fragments that can be used in various embodiments of the present invention are illustrated in Table 1 below. Any of these proteins, variants, chimeric proteins, or fragments can be appended with one, two, or more amino acid residues (e.g., a methionine at the N-terminus of the fragment, as shown for the C-terminal fragments below). Moreover, given the provision of these constructs and the information provided in the Examples, one of skill in the art will readily be able to produce other constructs where additional amino acids are deleted, where domains of a chimera are reversed in order, or where two or more fragments or portions thereof described herein are combined to produce additional chimeric proteins.

TABLE 1

N3 Probe (N-term fraQment) aa1-74 of SEQ ID NO: 2
Mr = 8576 pI = 6.72
MEFLERTYLVNDKAAKMYAFTLESVELQQKPVNKDQCPRERPEELESGGM
YHCHSGSKPTEKGANEYAYAKWKL
(SEQ ID NO: 8)

C4 Probe (C-term fragment) aa268-369 of
SEQ ID NO: 2 Mr 11235 PI = 4.95
MKDFSILLMEGVPKSLNYSGVKELILAVDGVLSVHSLHIWSLTMNQVILS
AHVATAASRDSQVVRREIAKALSKSFTMHSLTIQMESPVDQDPDCLFCED
PCD
(SEQ ID NO: 9)

Truncated C-terminal probe 1 (active in assays
described herein)
MKDFSILLMEGVPKSLNYSGVKELILAVDGVLSVHSLHIWSLTMNQVILS
AHVATAASRDSQVVRREIAKALSKSFTMHSLTIQMES
(SEQ ID NO: 10)

Truncated C-terminal probe 2 (inactive in assays
described herein)
MKDFSILLMEGVPKSLNYSGVKELILAVDGVLSVHSLHIWSLTMNQVILS
AHVATAASRDSQVVRREIAKALSKSFTM
(SEQ ID NO: 11)

Mutant C-terminal probe (reduced activity in
assays described herein)
MKDFSILLMEGVPKSLNYSGVKELILAVDGVLSVHSLHIWSLTMNQVILS
AHVATAASRDSQVVRREIAKALSASFTMASLTIQMAAPVDQDPDCLFCED
PCD
(SEQ ID NO: 12)

Zinc Binding Loop
VLTVVLHQRCLGHNHKEVQANASVRA
(SEQ ID NO: 13)

TABLE 1-continued

M275 Probe aa275-369 of SEQ ID NO: 2 Mr 10414
PI = 5.21
MEGVPKSLNY SGVKELILAV DGVLSVHSLH IWSLTMNQVI
LSAHVATAAS RDSQVVRREI AKALSKSFTM HSLTIQMESP
VDQDPDCLFC EDPCD
(SEQ ID NO: 14)

M282 Probe aa283-369 of SEQ ID NO: 2 Mr 9703
PI = 5.15
MNYSGVKELI LAVDGVLSVH SLHIWSLTMN QVILSAHVAT
AASRDSQVVR REIAKALSKS FTMHSLTIQM ESPVDQDPDC
LFCEDPCD
(SEQ ID NO: 15)

M282 Probe aa290-369 of SEQ ID NO: 2 Mr 8699
PI = 5.08
MILAVDGVLS VHSLHIWSLT MNQVILSAHV ATAASRDSQV
VRREIAKALS KSFTMHSLTI QMESPVDQDP DCLFCEDPCD
(SEQ ID NO: 16)

M300 Probe aa300-369 of SEQ ID NO: 2 Mr 7845
PI = 5.50
MHSLHIWSLT MNQVILSAHV ATAASRDSQV VRREIAKALS
KSFTMHSLTI QMESPVDQDP DCLFCEDPCD
(SEQ ID NO: 17)

M305 Probe aa300-369 of SEQ ID NO: 2 Mr 7257
PI = 4.74
MWSLTMNQVI LSAHVATAAS RDSQVVRREI AKALSKSFTM
HSLTIQMESP VDQDPDCLFC EDPCD
(SEQ ID NO: 18)

C4 Probe Δaa293-369 of SEQ ID NO: 2 Mr 2827
PI = 4.68 (SalI cut)
MDFSILLMEG VPKSLNYSGV KELILA
(SEQ ID NO: 19)

C4 Probe Δaa325-369 of SEQ ID NO: 2 Mr 6109
PI = 6.13 (HpaII cut)
MDFSILLMEG VPKSLNYSGV KELILAVDGV LSVHSLHIWS
LTMNQVILSA HVATAAS
(SEQ ID NO: 20)

C4 Probe Δaa344-369 of SEQ ID NO: 2 Mr 8282
PI = 8.87 (HphI cut)
MDFSILLMEG VPKSLNYSGV KELILAVDGV LSVHSLHIWS
LTMNQVILSA HVATAASRDS QVVRREIAKA LSKSFT
(SEQ ID NO: 21)

C4 Probe Δaa351-369 of SEQ ID NO: 2 Mr 9093
PI = 28.87 (BstXI cut)
MDFSILLMEG VPKSLNYSGV KELILAVDGV LSVHSLHIWS
LTMNQVILSA HVATAASRDS QVVRREIAKA LSKSFTMHSL
TIQMESPVDQ DPDCLFCEDP CD
(SEQ ID NO: 22)

C4 Probe Δaa357-369 of SEQ ID NO: 2 Mr 9752
PI = 26.86 (BstNI cut)
MDFSILLMEG VPKSLNYSGV KELILAVDGV LSVHSLHIWS
LTMNQVILSA HVATAASRDS QVVRREIAKA LSKSFTMHSL
TIQMESPVD
(SEQ ID NO: 23)

C4 Wild tyDe aa268-369 of SEQ ID NO: 2 Mr 11235
PI = 4.95 (mutants underlined)
MDFSILLMEG VPKSLNYSGV KELILAVDGV LSVHSLHIWS
LTMNQVILSA HVATAASRDS QVVRREIAKA LSKSFTMHSL
TIQMESPVDQ DPDCLFCEDP CD
(SEQ ID NO: 24)

Additional C4 Mutant probes (SEQ ID NO: 9 with
mutations relevant to positions of SEQ ID NO: 2):
K340A; Mr = 11177 pI = 4.74
H345A; Mr = 11168 pI = 4.74
E352A; Mr = 11176 pI = 5.17
S353A; Mr = 11218 pI = 4.95
S353D; Mr = 11262 pI = 4.77
Triple K340A, H345A, E345A; Mr = 11053 pI = 4.67

TABLE 1-continued

Mouse ZnT8 amino acid sequence variants mSLC30a8 C-term Met266, Gln324
MKDFSILLME GVPKGLSYNS VKEIILAVDG VISVHSLHIW
SLTVNQVILS VHVATAASQD SQSVRTGIAQ ALSSFDLHSL
TIQIESAADQ DPSCLLCEDP QD
(SEQ ID NO: 40)

mSLC30a8 C-term Met266, Arg324
MKDFSILLME GVPKGLSYNS VKEIILAVDG VISVHSLHIW
SLTVNQVILS VHVATAASRD SQSVRTGIAQ ALSSFDLHSL
TIQIESAADQ DPSCLLCEDP QD
(SEQ ID NO: 41)

mSLC30a8 C-term Met266, Trp324
MKDFSILLME GVPKGLSYNS VKEIILAVDG VISVHSLHIW
SLTVNQVILS VHVATAASWD SQSVRTGIAQ ALSSFDLHSL
TIQIESAADQ DPSCLLCEDP QD
(SEQ ID NO: 42)

mSLC30a8 C-term Met266, Lys339(insert)
MKDFSILLME GVPKGLSYNS VKEIILAVDG VISVHSLHIW
SLTVNQVILS VHVATAASQD SQSVRTGIAQ ALSKSFDLHS
LTIQIESAAD QDPSCLLCED PQD
(SEQ ID NO: 43)

mSLC30a8 C-term Met266, Arg324, Lys339(insert)
MKDFSILLME GVPKGLSYNS VKEIILAVDG VISVHSLHIW
SLTVNQVILS VHVATAASRD SQSVRTGIAQ ALSKSFDLHS
LTIQIESAAD QDPSCLLCED PQD
(SEQ ID NO: 44)

mSLC30a8 C-term Met266, Trp324, Lys339(insert)
MKDFSILLME GVPKGLSYNS VKEIILAVDG VISVHSLHIW
SLTVNQVILS VHVATAASWD SQSVRTGIAQ ALSKSFDLHS
LTIQIESAAD QDPSCLLCED PQD
(SEQ ID NO: 45)

Met266 REKK mutant TGIAQALS331-338 > REIAKALSK 332-340
MKDFSILLME GVPKGLSYNS VKEIILAVDG VISVHSLHIW
SLTVNQVILS VHVATAASQD SQSVRREIAK ALSKSFDLHS
LTIQIESAAD QDPSCLLCED PQD
(SEQ ID NO: 46)

Met266 RREKK mutant (R325; TGIAQALS331-338 > REIAKALSK332-340
MKDFSILLME GVPKGLSYNS VKEIILAVDG VISVHSLHIW
SLTVNQVILS VHVATAASRD SQSVRREIAK ALSKSFDLHS
LTIQIESAAD QDPSCLLCED PQD
(SEQ ID NO: 47)

Met266 WREKK mutant (R325: TGIAQALS331-338 > REIAKALSK332-340
MKDFSILLME GVPKGLSYNS VKEIILAVDG VISVHSLHIW
SLTVNQVILS VHVATAASWD SQSVRREIAK ALSKSFDLHS
LTIQIESAAD QDPSCLLCED PQD
(SEQ ID NO: 48)

Human ZnT8 amino acid sequence variants hSLC30a8 C-term 267Met, 325Arg
MKDFSILLME GVPKSLNYSG VKELILAVDG VLSVHSLHIW
SLTMNQVILS AHVATAASRD SQVVRREIAK ALSKSFTMHS
LTIQMESPVD QDPDCLFCED PCD
(SEQ ID NO: 49)

hSLC30a8 C-term 267Met, 325Gln
MKDFSILLME GVPKSLNYSG VKELILAVDG VLSVHSLHIW
SLTMNQVILS AHVATAASQD SQVVRREIAK ALSKSFTMHS
LTIQMESPVD QDPDCLFCED PCD
(SEQ ID NO: 50)

hSLC30a8 C-term 267Met, 325Trp
MKDFSILLME GVPKSLNYSG VKELILAVDG VLSVHSLHIW
SLTMNQVILS AHVATAASWD SQVVRREIAK ALSKSFTMHS
LTIQMESPVD QDPDCLFCED PCD
(SEQ ID NO: 51)

TABLE 1-continued hSLC30A8 linker sequence
PSTPPGSSGG G
(SEQ ID NO: 52)

hSLC30a8 C-term dimer 1Met, 59Arg, linker, 172Arg (Positions 59 and 172 corresrond to aa325 in wildtype)
MKDFSILLME GVPKSLNYSG VKELILAVDG VLSVHSLHIW
SLTMNQVILS AHVATAASRD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SRDSQVVRRE IAKALSKSFT MHSLTIQMES
PVDQDPDCLF CEDPCD
(SEQ ID NO: 53)

hSLC30a8 C-term dimer 1Met, 59Arg, linker, 172Gm
MKDFSILLME GVPKSLNYSG VKELILAVDG VLSVHSLHIW
SLTMNQVILS AHVATAASRD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SQDSQVVRRE IAKALSKSFT MHSLTIQMES
PVDQDPDCLF CEDPCD
(SEQ ID NO: 54)

hSLC30a8 C-term dimer 1Met, 59Arg, linker, 172Trp
MKDFSILLME GVPKSLNYSG VKELILAVDG VLSVHSLHIW
SLTMNQVILS AHVATAASRD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SWDSQVVRRE IAKALSKSFT MHSLTIQMES
PVDQDPDCLF CEDPCD
(SEQ ID NO: 55)

hSLC30a8 C-term dimer 1Met, 59Gln, linker, 172Gln
MKDFSILLME GVPKSLNYSG VKELILAVDG VLSVHSLHIW
SLTMNQVILS AHVATAASQD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SQDSQVVRRE IAKALSKSFT MHSLTIQMES
PVDQDPDCLF CEDPCD
(SEQ ID NO: 56)

hSLC30a8 C-term dimer 1Met, 59Gln, linker, 172Arg
MKDFSILLME GVPKSLNYSG VKELILAVDG VLSVHSLHIW
SLTMNQVILS AHVATAASQD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SRDSQVVRRE IAKALSKSFT MHSLTIQMES
PVDQDPDCLF CEDPCD
(SEQ ID NO: 57)

hSLC30a8 C-term dimer 1Met, 59Gln, linker, 172Trp (Positions 59 and 172 correspond to aa325 in wildtype)
MKDFSILLME GVPKSLNYSG VKELILAVDG VLSVHSLHIW
SLTMNQVILS AHVATAASQD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SQDSWVVRRE IAKALSKSFT MHSLTIQMES
PVDQDPDCLF CEDPCD
(SEQ ID NO: 58)

hSLC30a8 C-term dimer 1Met, 59Trp, linker, 172Trp
MKDFSILLME GVPKSLNYSG VKELILAVDG VLSVHSLHIW
SLTMNQVILS AHVATAASWD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SWDSQVVRRE IAKALSKSFT MHSLTIQMES
PVDQDPDCLF CEDPCD
(SEQ ID NO: 59)

hSLC30a8 C-term dimer 1Met, 59Trp, linker, 172Arg
MKDFSILLME GVPKSLNYSG VKELILAVDG VLSVHSLHIW
SLTMNQVILS AHVATAASWD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SRDSQVVRRE IAKALSKSFT MHSLTIQMES
PVDQDPDCLF CEDPCD
(SEQ ID NO: 60)

TABLE 1-continued hSLC30a8 C-term dimer 1Met, 59Trp, linker, 172Gln
MKDFSILLME GVPKSLNYSG VKELILAVDG VLSVHSLHIW
SLTMNQVILS AHVATAASWD SQVVRREIAK ALSKSFTMHS
LTIQMESPVD QDPDCLFCED PCDPSTPPGS SGGGKDFSIL
LMEGVPKSLN YSGVKELILA VDGVLSVHSL HIWSLTMNQV
ILSAHVATAA SQDSQVVRRE IAKALSKSFT MHSLTIQMES
PVDQDPDCLF CEDPCD
(SEQ ID NO: 61)

hSLC30a8 N-term/C-term fusion wild type Trp325 variant
MEFLERTYLV NDKAAKMYAF TLESVELQQK PVNKDQCPRE
RPEELESGGM YHCHSGSKPT EKGANEYAYA KWKLCSGGGK
DFSILLMEGV PKSLNYSGVK ELILAVDGVL SVHSLHIWSL
TMNQVILSAH VATAASWDSQ VVRREIAKAL SKSFTMHSLT
IQMESPVDQD PDCLFCEDPC D
(SEQ ID NO: 62)

hSLC30a8 N-term/C-term fusion wild type Arg325 variant
MEFLERTYLV NDKAAKMYAF TLESVELQQK PVNKDQCPRE
RPEELESGGM YHCHSGSKPT EKGANEYAYA KWKLCSGGGK
DFSILLMEGV PKSLNYSGVK ELILAVDGVL SVHSLHIWSL
TMNQVILSAH VATAASRDSQ VVRREIAKAL SKSFTMHSLT
IQMESPVDQD PDCLFCEDPC D
(SEQ ID NO: 63)

hSLC30a8 N-term/C-term fusion wild type Trp325 variant - alternate start codon
MYHCHSGSKP TEKGANEYAY AKWKLCSGGG KDFSILLMEG
VPKSLNYSGV KELILAVDGV LSVHSLHIWS LTMNQVILSA
HVATAASWDS QVVRREIAKA LSKSFTMHSL TIQMESPVDQ
DPDCLFCEDP CD
(SEQ ID NO: 64)

hSLC30a8 N-term/C-term fusion wild type Arg325 variant - alternate start codon
MYHCHSGSKP TEKGANEYAY AKWKLCSGGG KDFSILLMEG
VPKSLNYSGV KELILAVDGV LSVHSLHIWS LTMNQVILSA
HVATAASRDS QVVRREIAKA LSKSFTMHSL TIQMESPVDQ
DPDCLFCEDP CD
(SEQ ID NO: 65)

hSLC30a8 C-term/N-term fusion wild tyre Arg325 variant
MKDFSILLME GVPKSLNYSG VKELILAVDG VLSVHSLHIW
SLTMNQVILS AHVATAASRD SQVVRREIAK ALSKSFTMHS
LTIQMESPVD QDPDCLFCED PCDGGGMEFL ERTYLVNDKA
AKMYAFTLES VELQQKPVNK DQCPRERPEE LESGGMYHCH
SGSKPTEKGA NEYAYAKWKL CS
(SEQ ID NO: 66)

Sequence hSLC30a8 without TM segments Trp325 variant
MEFLERTYLV NDKAAKMYAF TLESVELQQK PVNKDQCPRE
RPEELESGGM YHCHSGSKPT EKGANEYAYA KWKLCSASDA
AHLLIDSSKP PSKRLTFGWH RAECERLLYP DYQIQATLHQ
RCLGHNHKEV QANASVRKPE YKKDFSILLM EGVPKSLNYS
GVKELILAVD GVLSVHSLHI WSLTMNQVIL SAHVATAASW
DSQVVRREIA KALSKSFTMH SLTIQMESPV DQDPDCLFCE
DPCD
(SEQ ID NO: 67)

The sequences listed in Table 1 were designed by the inventors to test various features of patient autoreactivity, and to design assays that either discriminated better between patients, or conversely, were pan-reactive. The following listing shows how the sequences described above have been categorized by the inventors with respect to patient autoreactivity (patient serum samples). Reference to a sequence not in parentheses indicates identification of patient reactivity towards the construct comprising that sequence; sequences shown in parentheses indicate either reduced activity or variable activity that is likely the product of other specificities that have yet to be defined. The absence of identification of a sequence number with respect to a particular sample type indicates lack of reactivity. In the case of Gln325-restricted reactivity, the information is limited as only one patient serum has been identified to date from more than 500 that have been tested.

N-term reactive samples: SEQ ID NOs: 8, 63, 64, 65

Arg325-restricted reactivity: SEQ ID NOs: 9, 10, (11), (12), 14, 15, (16 to 21), (22), 23, (24 to 30), (40), 41, (42), (43), 44, 47, 49, (52), 53, 54, 55, 57, 60, 63, 65

Trp325-restricted reactivity: SEQ ID NOs: (40), (41), 42, (43), 45, 48, 51, (52), 55, 58, 59, 60, 61, 62, 64

Gln325-restricted reactivity: SEQ ID NOs: 40, (41), (42), 50

Amino acid 325 independent: SEQ ID NOs: 9 to 16, (17 to 21), 22, 23, 24, (25 to 30), (40, 41), 42, (43), 47 to 51, (52), 53 to 65

The present invention also includes ZnT8 proteins that comprise, consist essentially of, or consist of an antigenic peptide or T cell epitope (also referred to as a major histocompatibility complex (MHC)-binding peptide). Such a peptide includes any peptide that is capable of binding to an MHC protein in a manner such that the MHC-peptide complex can bind to a T cell receptor (TcR) and, in a preferred embodiment, thereby induce a T cell response (e.g., a stimulatory or toleragenic response, described below). An MHC-binding peptide that binds to an MHC molecule and is recognized, in conjunction with the MHC molecule, by a T cell receptor, is considered to be an antigenic peptide. In nature, peptides that are produced by hydrolysis of antigens undergo hydrolysis prior to binding of the antigen to an MHC protein. Class I MHC proteins typically present antigenic peptides derived from proteins actively synthesized in the cytoplasm of the cell. In contrast, class II MHC proteins typically present antigenic peptides derived either from exogenous proteins that enter a cell's endocytic pathway or from proteins synthesized in the endoplasmic reticulum (ER). Intracellular trafficking permits an antigenic peptide to become associated with an MHC protein. The resulting MHC-peptide complex then travels to the surface of the cell where it is available for interaction with a TcR.

The binding of a peptide to an MHC peptide binding groove can control the spatial arrangement of MHC and/or peptide amino acid residues recognized by a TcR. Such spatial control is due in part to hydrogen bonds formed between a peptide and an MHC protein. Preferably, the length of T cell epitope is from about 5 to about 40 amino acid residues, more preferably from about 6 to about 30 amino acid residues, and even more preferably from about 8 to about 20 amino acid residues, and even more preferably between about 9 and 11 amino acid residues, including any size peptide between 5 and 40 amino acids in length, in whole integer increments (i.e., 5, 6, 7, 8, 9 . . . 40). While naturally MHC Class II-bound peptides vary from about 9-40 amino acids, in nearly all cases the peptide can be truncated to an about 9-11 amino acid core without loss of MHC binding activity or T cell recognition.

General Definitions and Embodiments Related to Polynucleotides and Proteins or Peptides The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Molecular Cloning: A Laboratory Manual*, second edition (Sambrook et al., 1989)

and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000).

In accordance with the present invention, an isolated polynucleotide (also referred to as an isolated nucleic acid molecule) is a nucleic acid molecule that has been removed from its natural milieu (e.g., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. The polynucleotides useful in the present invention are typically a portion of a gene (sense or non-sense strand) of the present invention that is suitable for use as a hybridization probe or PCR primer for the identification of a full-length gene (or portion thereof) in a given sample, or that is suitable for encoding a ZnT8 protein or fragment thereof, or that is suitable as a therapeutic reagent (e.g., antisense or an aptamer). An isolated nucleic acid molecule can include a gene or a portion of a gene (e.g., the regulatory region or promoter), for example, to produce a reporter construct or a recombinant protein. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

The minimum size of a nucleic acid molecule or polynucleotide of the present invention is a size sufficient to encode a protein having a desired biological activity, sufficient to form a probe or oligonucleotide primer that is capable of forming a stable hybrid with the complementary sequence of a nucleic acid molecule encoding the natural protein (e.g., under moderate, high or very high stringency conditions), or to otherwise be used as a target or agent in an assay or in any therapeutic method discussed herein. If the polynucleotide is an oligonucleotide probe or primer, the size of the polynucleotide can be dependent on nucleic acid composition and percent homology or identity between the nucleic acid molecule and a complementary sequence as well as upon hybridization conditions per se (e.g., temperature, salt concentration, and formamide concentration). The minimum size of a polynucleotide that is used as an oligonucleotide probe or primer is at least about 5 nucleotides in length, and preferably ranges from about 5 to about 50 or about 500 nucleotides or greater (1000, 2000, etc.), including any length in between, in whole number increments (i.e., 5, 6, 7, 8, 9, 10, . . . 33, 34, . . . 256, 257, . . . 500 . . . 1000 . . . ), and more preferably from about 10 to about 40 nucleotides, and most preferably from about 15 to about 40 nucleotides in length. In one aspect, the oligonucleotide primer or probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein-encoding sequence or a nucleic acid sequence encoding a full-length protein.

According to the present invention, an oligonucleotide probe (or simply, probe) is a nucleic acid molecule which most typically ranges in size from about 8 nucleotides to several hundred nucleotides in length. Such a molecule is typically used to identify a target nucleic acid sequence in a sample by hybridizing to such target nucleic acid sequence under stringent hybridization conditions. As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M $Na^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M $Na^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×–0.5×SSC, followed by at least one wash at about 68° C. in about 0.1×–0.5×SSC).

PCR primers are also nucleic acid sequences, although PCR primers are typically oligonucleotides of fairly short length that are used in polymerase chain reactions. PCR primers and hybridization probes can readily be developed and produced by those of skill in the art, using sequence information from the target sequence. (See, for example, Sambrook et al., supra or "Molecular Biotechnology," Second Edition, by Glick and Pasternak, ASM Press, Washington D.C., 1998, pp. 555-590).

Knowing the nucleic acid sequences of certain nucleic acid molecules of the present invention allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes to screen appropriate libraries or DNA and PCR amplification of appropriate libraries or DNA using oligonucleotide primers. Preferred libraries to screen or from which to amplify nucleic acid molecule include mammalian genomic DNA libraries. Techniques to clone and amplify genes are disclosed, for example, in Sambrook et al., ibid.

As used herein, an anti-sense nucleic acid molecule is defined as an isolated nucleic acid molecule that reduces expression of a protein by hybridizing under high stringency conditions to a gene encoding the protein. Such a nucleic acid molecule is sufficiently similar to the gene encoding the protein that the molecule is capable of hybridizing under high stringency conditions to the coding or complementary strand of the gene or RNA encoding the natural protein.

RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA.

A ribozyme is an RNA segment that functions by binding to the target RNA moiety and inactivate it by cleaving the phosphodiester backbone at a specific cutting site. A ribozyme can serve as a targeting delivery vehicle for a nucleic acid molecule, or alternatively, the ribozyme can target and bind to RNA encoding the biomarker, for example, and thereby effectively inhibit the translation of the biomarker.

Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure.

A recombinant nucleic acid molecule is a molecule that can include at least one of any nucleic acid sequence encoding a ZnT8 protein or other protein described herein. In one embodiment, a recombinant nucleic acid molecule is operatively linked to at least one expression control sequence capable of effectively regulating expression of the nucleic acid molecule(s) in a host cell. Preferably, a recombinant nucleic acid molecule is produced using recombinant DNA technology (e.g., polymerase chain reaction (PCR) amplification, cloning). A recombinant nucleic acid molecule includes a recombinant vector, which is any nucleic acid sequence, typically a heterologous sequence, which is operatively linked to the isolated nucleic acid molecule encoding a protein (e.g., ZnT8), which is capable of enabling recombinant production of the protein, or which is capable of delivering the nucleic acid molecule into a host cell in vitro, ex vivo or in vivo, according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules. Recombinant vectors are preferably used in the expression of nucleic acid molecules, and can also be referred to as expression vectors. Preferred recombinant vectors are capable of being expressed in a transfected host cell, and particularly, in a transfected mammalian host cell in vivo.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. The phrase "operatively linked" refers to linking a nucleic acid molecule to an expression control sequence in a manner such that the molecule is expressed when transfected (i.e., transformed, transduced or transfected) into a host cell.

Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in a host cell according to the present invention. A variety of suitable transcription control sequences are known to those skilled in the art. Particularly preferred transcription control sequences include inducible promoters, cell-specific promoters, tissue-specific promoters (e.g., insulin promoters) and enhancers. Transcription control sequences of the present invention can also include naturally occurring transcription control sequences naturally associated with the protein to be expressed prior to isolation. In one embodiment, a transcription control sequence includes an inducible promoter.

One type of recombinant vector useful in a recombinant nucleic acid molecule of the present invention is a recombinant viral vector. Such a vector includes a recombinant nucleic acid sequence encoding a ZnT8 protein of the present invention that is packaged in a viral coat that can be expressed in a host cell in an animal or ex vivo after administration. A number of recombinant viral vectors can be used, including, but not limited to, those based on alphaviruses, poxviruses, adenoviruses, herpesviruses, lentiviruses, adeno-associated viruses and retroviruses. Particularly preferred viral vectors are those based on adenoviruses and adeno-associated viruses. Viral vectors suitable for gene delivery are well known in the art and can be selected by the skilled artisan for use in the present invention. A detailed discussion of current viral vectors is provided in "Molecular Biotechnology," Second Edition, by Glick and Pasternak, ASM Press, Washington D.C., 1998, pp. 555-590, the entirety of which is incorporated herein by reference.

Suitable host cells to transfect with a recombinant nucleic acid molecule according to the present invention include any microbial, insect, or animal cell that can be transfected. Host cells can be either untransfected cells or cells that are already transfected with at least one nucleic acid molecule.

According to the present invention, the term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass both transfection of animal cells and transformation of microbial cells, to the extent that the terms pertain to the introduction of exogenous nucleic acids into a cell. Therefore, transfection techniques include, but are not limited to, transformation, electroporation, microinjection, lipofection, adsorption, infection and protoplast fusion.

As used herein, reference to an isolated protein or polypeptide in the present invention, including a ZnT8 protein, is a protein that has been removed from its natural milieu (i.e., that has been subject to human manipulation), and includes full-length proteins, fusion or chimeric proteins, or any fragment or homologue of such a protein. Such a protein can include, but is not limited to, purified proteins, partially purified proteins, recombinantly produced proteins, synthetically produced proteins, membrane-bound proteins, proteins complexed with lipids, soluble proteins and isolated proteins associated with other proteins. As such, "isolated" does not reflect the extent to which the protein has been purified. Preferably, an isolated protein of the present invention is produced recombinantly. In addition, and again by way of example, a "human ZnT8 protein" or a protein "derived from" a human ZnT8 protein refers to a ZnT8 protein (generally including a homologue of a naturally occurring ZnT8 protein) from a human (*Homo sapiens*) or to a ZnT8 protein that has been otherwise produced from the knowledge of the structure (e.g., sequence) and perhaps the function of a naturally occurring ZnT8 protein from *Homo sapiens*. In other words, a human ZnT8 protein includes any ZnT8 protein that has substantially similar structure and function of a naturally occurring ZnT8 protein from *Homo sapiens* or that is a biologically active (i.e., has biological activity) homologue of a naturally occurring ZnT8 protein from *Homo sapiens* as described in detail herein. As such, a human ZnT8 protein can include purified, partially purified, recombinant, mutated/modified and synthetic proteins. According to the present invention, the terms "modification" and "mutation" can be used interchangeably, particularly with regard to the modifications/mutations to the amino acid sequence of protein (or nucleic acid sequences) described herein. An isolated protein useful as an antagonist or agonist according to the present invention can be isolated from its natural source, produced recombinantly or produced synthetically.

Fusion proteins and chimeric proteins are also encompassed by the invention. A fusion protein is a protein produced by linking (typically recombinantly, although chemical and other types of linkage are encompassed by the invention) of a protein or peptide of the invention (e.g., ZnT8 or a variant or fragment thereof) to a fusion partner (fusion segment). Suitable fusion partners for use with the present invention include, but are not limited to, fusion partners that can: enhance a protein's stability; enhance or permit secretion of a protein from the host cell; provide other biological activity; and/or assist purification of a protein from a host cell (e.g., by affinity chromatography). A suitable fusion partner can be a protein or domain or fragment thereof of any size that has the desired function (e.g., imparts increased stability, solubility, action or activity; provides other activity; and/or simplifies purification of a protein). Fusion partners can be joined to amino and/or carboxyl termini of the protein of interest (e.g., ZnT8), and can be susceptible to cleavage in order to enable straight-forward recovery of the expressed exogenous protein. A chimeric protein is similar to a fusion protein, and the terms may be used interchangeably, except that in the case of the chimeric protein, the fusion partner is most typically a second protein of interest (or a fragment thereof), such as a second protein with a desired biological activity. Accordingly, a chimeric protein may have the activity of each/both of the protein/peptide components, or a new activity resulting from the combination of protein domains.

In one preferred embodiment, proteins (including peptides and homologues) are produced using in vitro translation systems, such as systems based on reticulocyte lysate, wheat germ, yeast and bacteria. The systems preferably correctly post-translationally process the protein, e.g., by proteolysis and/or glycosylation. Products of in vitro translation systems are most typically used in the methods of the invention, although the invention is not limited to such products.

As used herein, the term "homologue" or "variant" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in 1, 2, 3, 4, 5, 6, 7, 8, 9, 10, or a few more amino acid side chains; changes 1, 2, 3, 4, 5, 6, 7, 8, 9, 10, or a few more amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein.

Homologues can be the result of natural allelic variation or genetic polymorphism, or any natural mutation. A naturally occurring allelic variant or genetic polymorphism of a nucleic acid encoding a protein is a gene that occurs at essentially the same locus (or loci) in the genome as the gene which encodes such protein, but which, due to natural variations, has a similar but not identical sequence. Allelic variants typically encode proteins having similar activity to that of the protein encoded by the gene to which they are being compared. A single nucleotide polymorphism (SNP) is a DNA sequence variation occurring when a single nucleotide in the genome differs between members of a species, or between paired chromosomes in an individual. Due to variations between human populations, a SNP allele that is common in one geographical or ethnic group may be much rarer in another. In addition, variations in the DNA sequences of humans can affect how humans develop diseases and respond to pathogens, chemicals, drugs, vaccines, and other agents, and that has been exemplified herein by the autoantibody response to polymorphisms occurring in the ZnT8 gene.

One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

According to the present invention, an isolated protein, including a biologically active homologue or fragment thereof, has at least one characteristic of biological activity of activity the wild-type, or naturally occurring reference protein (which can vary depending on whether the homologue or fragment is an agonist or antagonist of the protein, or whether an agonist or antagonist mimetic of the protein is described). In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions).

The biological activity of a ZnT8 protein of the invention includes transporting zinc out of cells or sequestrating zinc into intracellular compartments. More particularly, a biological activity of ZnT8 according to the invention includes the translocation of the cytoplasmic zinc into intracellular vesicles of the β cells of the islet. Other biological activities of ZnT8 useful in the present invention include induction of an immune response against ZnT8, including both a cellular and humoral immune response, as well as the ability to be recognized by a binding agent in an assay (e.g., forming a primary or tertiary structure or conformational epitope that can be recognized by a ZnT8-specific binding agent).

Modifications, activities or interactions which result in a decrease in protein expression or a decrease in the activity of the protein, can be referred to as inactivation (complete or partial), down-regulation, reduced action, or decreased action or activity of a protein. Similarly, modifications, activities or interactions that result in an increase in protein expression or an increase in the activity of the protein, can be referred to as amplification, overproduction, activation, enhancement, up-regulation or increased action of a protein. The biological activity of a protein according to the invention, and particularly a ZnT8 protein, can be measured or evaluated using any assay for the biological activity of the protein as known in the art. Such assays can include, but are not limited to, binding assays (including a variety of immunological assays), assays to determine internalization or localization of the protein and/or associated proteins, zinc transport assays (e.g., see the zinquin assay described in Chimienti et al., 2004, *Diabetes*, supra) and/or assays for determining downstream cellular events that result from the activity of the protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:

Reward for match=1

Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

As used herein, reference to an "agonist" of a given protein refers to any compound that is characterized by the ability to agonize (e.g., stimulate, induce, increase, enhance, or mimic) the biological activity of the naturally occurring protein, and includes any homologue, binding protein (e.g., an antibody), agent that interacts with a protein or receptor bound by the protein, or any suitable product of drug/compound/peptide design or selection which is characterized by its ability to agonize (e.g., stimulate, induce, increase, enhance) the biological activity of the naturally occurring protein in a manner similar to the natural agonist, which is the reference protein.

Similarly, reference to an "antagonist" refers to any compound which inhibits (e.g., antagonizes, reduces, decreases, blocks, reverses, or alters) the effect of a given agonist of a protein (including the protein itself) as described above. More particularly, an antagonist is capable of acting in a manner relative to the activity of the protein, such that the biological activity of the natural agonist or reference protein, is decreased in a manner that is antagonistic (e.g., against, a reversal of, contrary to) to the natural action of the protein. Such antagonists can include, but are not limited to, a protein, peptide, or nucleic acid (including ribozymes, RNAi, aptamers, and antisense), antibodies and antigen binding fragments thereof, or product of drug/compound/peptide design or selection that provides the antagonistic effect.

Homologues of a given protein such as ZnT8, including peptide and non-peptide agonists and antagonists (analogs), can be products of drug design or selection and can be produced using various methods known in the art. Such homologues can be referred to as mimetics. Various methods of drug design, useful to design or select mimetics or other therapeutic compounds useful in the present invention are disclosed in Maulik et al., 1997, *Molecular Biotechnology: Therapeutic Applications and Strategies*, Wiley-Liss, Inc., which is incorporated herein by reference in its entirety.

As used herein, a mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art.

A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Antibodies and Antigen-Binding Partners of the Invention

Also included in the present invention are antibodies and antigen binding fragments thereof that selectively bind to ZnT8, as well as the use of such antibodies and antigen binding fragments thereof in any of the methods described herein. Antibodies that selectively bind to a protein can be produced using the structural information available for the protein (e.g., the amino acid sequence of at least a portion of the protein). As used herein, the term "selectively binds to" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

According to the present invention, an "epitope" of a given protein or peptide or other molecule is generally defined, with regard to antibodies, as a part of or site on a larger molecule to which an antibody or antigen-binding fragment thereof will bind, and against which an antibody will be produced. The term epitope can be used interchangeably with the term "antigenic determinant", "antibody binding site", or "conserved binding surface" of a given protein or antigen. More specifically, an epitope can be defined by both the amino acid residues involved in antibody binding and also by their conformation in three dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential epitope (i.e., linear epitope), or in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions. Accordingly, the present invention includes any proteins or peptides comprising or consisting of any ZnT8 epitopes, as well as antibodies, antigen-binding fragments, or other binding partners (binding peptides) that bind to any epitope of a ZnT8 protein.

An "isoepitope", according to the invention, is an epitope that exists in variant forms or isoforms (naturally or by synthetic design), such as an epitope containing a polymorphic variant amino acid position(s). An example of an isoepitope is described herein by an epitope of ZnT8 containing position 325, wherein one isoepitope contains an arginine at position 325, and where two other variants naturally occur at that position (Trp325 and Gln325). These three variants are isoepitopes.

One of skill in the art can identify and/or assemble conformational epitopes and/or sequential epitopes using known techniques, including mutational analysis (e.g., site-directed mutagenesis); protection from proteolytic degradation (protein footprinting); mimotope analysis using, e.g., synthetic peptides and pepscan, BIACORE or ELISA; antibody competition mapping; combinatorial peptide library screening; matrix-assisted laser desorption/ionization time-of-flight (MALDI-TOF) mass spectrometry; or three-dimensional modeling (e.g., using any suitable software program, including, but not limited to, MOLSCRIPT 2.0 (Avatar Software AB, Heleneborgsgatan 21C, SE 11731 Stockholm, Sweden), the graphical display program O (Jones et. al., Acta Crystallography, vol. A47, p. 110, 1991), the graphical display program GRASP, or the graphical display program INSIGHT). For example, one can use molecular replacement or other techniques and the known three-dimensional structure of a related protein to model the three-dimensional structure of ZnT8 and predict the conformational epitope of antibody binding to this structure. Indeed, one can use one or any combination of such techniques to define the antibody binding epitope.

Antibodies useful in the present invention can include polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies of the present invention can include serum containing such antibodies, or antibodies that have been purified to varying degrees. Alternatively, functional equivalents of whole antibodies, such as antigen binding fragments in which one or more antibody domains are truncated or absent (e.g., Fv, Fab, Fab', or $F(ab)_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495-497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

The invention also extends to non-antibody polypeptides, sometimes referred to as antigen binding partners or antigen binding peptides, that have been designed to bind selectively to the protein of interest. Examples of the design of such polypeptides, which possess a prescribed ligand specificity are given in Beste et al. (*Proc. Natl. Acad. Sci.* 96:1898-1903, 1999), incorporated herein by reference in its entirety.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate or other molecule, or a portion thereof, wherein the antigen elicits an antigen-specific immune response (humoral and/or cellular immune response), or alternatively acts as a toleragen, against the same or similar antigens that are encountered within the cells and tissues of the animal to which the antigen is administered.

In one embodiment of the present invention, when it is desirable to stimulate an immune response, the term "antigen" can be used interchangeably with the term "immunogen", and is used herein to describe an antigen that elicits a humoral and/or cellular immune response (i.e., is immunogenic), such that administration of the immunogen to an animal (e.g., via a vaccine of the present invention) mounts an antigen-specific immune response against the same or similar antigens that are encountered within the tissues of the animal. In another embodiment, when it is desirable to suppress an immune response against a given antigen, an antigen can include a toleragen. According to the present invention, a "toleragen" is used to describe an antigen that is provided in a form, amount, or route of administration such that there is a reduced or changed immune response to the antigen, and preferably substantial non-responsiveness, anergy, other inactivation, or deletion of immune system cells in response to contact with the toleragen or a cell expressing or presenting such toleragen.

A "vaccinating antigen" can be an immunogen or a toleragen, but is an antigen used in a vaccine, where a biological response (elicitation of an immune response, tolerance) is to be elicited against the vaccinating antigen.

An immunogenic domain (portion, fragment, epitope) of a given antigen can be any portion of the antigen (e.g., a peptide fragment or subunit or an antibody epitope or other conformational epitope) that contains at least one epitope that acts as an immunogen (or toleragen, for a toleragenic domain) when administered to an animal. For example, a single protein can contain multiple different immunogenic domains. Immunogenic domains need not be linear sequences within a protein, in the case of a humoral response.

In generic terms, an epitope is defined herein as a single immunogenic site within a given antigen that is sufficient to elicit an immune response, or a single toleragenic site within a given antigen that is sufficient to suppress, delete or render inactive an immune response. As discussed above, those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions). depending on the type of immune response. An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms).

Compositions and Formulations of the Invention

ZnT8 proteins, homologues (including altered peptides), fragments, peptides, peptide and non-peptide mimetics, and antibodies and antigen-binding fragments thereof can be included in compositions, formulations and particularly, vaccines useful in the present invention. Such compositions, formulations or vaccines, can include a pharmaceutically acceptable carrier, which includes pharmaceutically acceptable excipients and/or delivery vehicles. As used herein, a pharmaceutically acceptable carrier refers to any substance suitable for delivering a composition, formulation or vaccine useful in the method of the present invention to a suitable in vivo or ex vivo site. Preferred pharmaceutically acceptable carriers are capable of maintaining the agent to be delivered (e.g., ZnT8 proteins, homologues (including altered peptides), fragments, peptides, peptide and non-peptide mimetics, and antibodies and antigen-binding fragments thereof) in a form that, upon arrival of the agent to a target cell or target site, the agent is capable of acting at that cell or site (e.g. capable of inducing an immune response). Suitable excipients of the present invention include excipients or formularies that transport or help transport, but do not specifically target an agent to a site (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into an animal. As used herein, a controlled release formulation comprises an agent useful in the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Suitable delivery vehicles also include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of an agent at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type.

A vaccine is a specific type of composition that is used to immunize or tolerize an animal against a particular antigen. Accordingly, a vaccine comprises at least one compound or agent that elicits an immune response against an antigen or immunogenic or toleragenic portion thereof, as a result of administration of the vaccine. Administration of a vaccine preferably results in a protective or therapeutic effect, wherein subsequent exposure to the antigen (or a source of the antigen) elicits an immune response against the antigen (or source) that reduces or prevents a disease or condition in the animal. Such immune responses can generally enhance or suppress the immune response to the antigen and in the case of ZnT8, it is preferred that a vaccine suppress an immune response against ZnT8 and/or the β cells of the pancreatic islets. The concept of vaccination is well known in the art. The immune response that is elicited by administration of a therapeutic composition of the present invention can be any detectable change in any facet of the immune response (e.g., cellular response, humoral response, cytokine production), as compared to in the absence of the administration of the vaccine.

Methods of the Invention

The present invention also includes a variety of methods that make use of the identification of ZnT8 as a novel autoantigen involved in type I diabetes (T1D). Such methods include diagnostic assays and assays used to monitor progression of disease or efficacy of treatment, as well as prophylactic and therapeutic methods, including immunotherapeutic methods and vaccine strategies. ZnT8 can also be used as a novel target to identify compounds useful for the diagnosis, prevention and/or treatment of T1D. The methods of the invention make use of any of the ZnT8 proteins, peptides, mimetics, homologues, antibodies, or even nucleic acid molecules described above. In some embodiments, such agents are combined with other diagnostic or therapeutic moieties to increase the effectiveness of a method. For example, detection of other autoantigens in addition to ZnT8 (e.g., insulin, insulinoma antigen, and/or glutamic acid decarboxylase) can be combined with detection of ZnT8 to extend the effectiveness, sensitivity and specificity of a diagnostic assay, and various therapeutic moieties (e.g., toxins, anti-inflammatory agents, antigens) can be combined with or attached to ZnT8 agents to enhance a therapeutic effect in patients.

Accordingly, one embodiment of the invention relates to a method and assay to detect diabetes related autoimmunity (i.e., type I diabetes or T1D). Such an assay can be used as a diagnostic assay (e.g., to identify a patient or group of subjects that is/are developing T1D or predict susceptibility to T1D) or as a prognostic/monitoring assay. The latter assay can be used to monitor the progression of autoimmunity in a patient or group of subjects from an initial benign (non-destructive) indication of an autoimmune response to destructive insulitis indicating overt T1D. The latter assay can also be used to monitor the efficacy of treatments that are directed to the prevention and/or treatment or amelioration of autoimmunity in prediabetic subjects. For example, subjects can be administered one or more immunosuppressive or preventative agents, including, but not limited to agents based on the ZnT8 molecule itself, and then the progression or non-progression to T1D can be monitored using an assay of the invention. The assay can be based on the detection of autoantibody responses to ZnT8 in the subject or the detection in the subject of T lymphocyte reactivity to ZnT8 antigenic epitope(s). The assays can be used separately or in conjunction with one another.

In one embodiment, the invention includes an antibody assay, which detects the presence or absence of antibodies that specifically bind to ZnT8 in a subject. The method of the invention can be used to effectively identify or select patients who, based on the level of antibodies against ZnT8 in the patient serum, are most likely to develop, or are developing, type I diabetes, including to predict factors such as time to onset, or monitor progression or stage of disease. The method can also be used to effectively identify or select patients who respond or do not respond to a particular therapeutic procedure (i.e., the method is used to indicate or contraindicate a therapeutic procedure for a particular patient).

In one aspect of the autoantibody assay of the invention, the specific isoepitopes defined by the polymorphisms in the ZnT8 gene and protein is detected. Diagnosis of the isoepitope specificity can be achieved with a simple diagnostic test that can be based on antibody binding to the specific ligand, be it as the intact protein or a peptide derived from it. Further analysis of specificity can be achieved by determining the ability of excess amounts of the specific variants of the protein or derived peptides to compete with the antibody interaction with the ligand. The analytical platform for such assays can be radioimmunoprecipitation, ELISA, luminescence time resolved fluorescence or a number of other generic assay formats.

The method generally includes detecting autoantibodies that selectively bind to ZnT8 in a patient or subject sample (test sample) using any suitable technique. The level of patient antibody binding can be standardized against a positive control (e.g., a positive serum control) and compared to an experimentally determined or predetermined cut-off (negative control level) for the antigen (ZnT8) and assay, in order to determine whether the test sample contains a level of anti-ZnT8 antibodies that is clinically or otherwise relevant. The assay may include the ability to screen for additional autoantigens other than ZnT8, including but not limited to, insulin, insulinoma antigen, and glutamic acid decarboxylase.

This method or assay of the invention more particularly includes providing a ZnT8 antigen against which patient antibodies can be detected. The ZnT8 antigen can be any suitable ZnT8-derived antigen including the full-length ZnT8 protein, or a homologue, fragment, fusion protein, altered peptide or peptide mimetic thereof, that detects serum antibodies against ZnT8 in a patient. The ZnT8 antigen contains at least one antibody epitope. A particularly preferred ZnT8 antigen is a C-terminal peptide of the ZnT8 protein, which is described in detail above.

In accordance with the present invention, an assay is conducted under conditions which are effective to screen for antibodies in accordance with the intended uses of this information as described herein. Effective conditions include, but are not limited to, appropriate media, temperature, pH and oxygen conditions that permit cell growth. Generally, a test sample from the patient is contacted with the ZnT8 antigen under competitive or non-competitive conditions, and binding of autoantibodies in the test sample to the ZnT8 antigen is detected, quantitated and compared to a negative and/or positive control. The techniques used to detect autoantibodies against ZnT8 in the sample can include any suitable assay, including but not limited to, ELISA (direct or indirect), radioimmunoprecipitation assays, time resolved fluorescence and luminescence assays. Such assay formats are well-known in the art.

One preferred assay for use in this embodiment of the invention is a competitive Europium assay. Such assay has been described in detail in U.S. Provisional Application No. 60/822,786, which is incorporated herein by reference in its entirety. This method generally includes performing a competitive antibody assay, where the detection method uses Europium fluorescence. The method more particularly includes the steps of immobilizing the antigen to which the subject antibody selectively binds to a substrate, such as the well of an assay plate or other suitable substrate; blocking non-specific binding sites on the substrate; applying a test sample (e.g., a serum sample from a subject to be evaluated for antibodies) to the plate, where the test sample has been preincubated in the presence and the absence of a fluid form of the antigen (i.e., the competition step); and finally, detecting antibody bound to the immobilized antigen using a Europium based detection system, such as secondary antibody conjugated to an agent (e.g., biotin), followed by a second agent that binds to the first agent (e.g., streptavidin) that is labeled with Europium. The level of fluorescence emitted by the Europium can then be detected using standard detection methods. Since the assay is a competitive assay, the fluorescence counts from the sample that was preincubated with the antigen is subtracted from the fluorescence counts from the sample that was not preincubated with the antigen to provide the result level. This level can be standardized against a positive serum control and compared to an experimentally determined or predetermined cut-off (negative control level) for the antigen and assay, in order to determine whether the test sample contains a level of antibodies that is clinically or otherwise relevant.

According to the present invention, the term "test sample" can be used generally to refer to a sample of any type which is believed to contain or may contain the antibodies to be detected by the present invention. A test sample can include a prepared sample, such as a sample that has been derived from a natural sample or synthetically produced, and is more preferably any biological sample obtained from a test subject (individual, patient, animal). A sample can therefore include a cell supernate, bodily fluid, tissue or other media that may contain an antibody to be detected. Bodily fluids suitable for sampling include, but are not limited to, blood, mucous, and breast milk, and most preferably is a blood or serum sample, with serum being particularly preferred.

As discussed above, an assay of the invention can be formatted to detect one antibody specificity (i.e., ZnT8), more than one (e.g., 2, 3, 4, 5, 6, 7, 8, 9, or 10) antibody specificity (i.e., detection of antibodies that bind to different antigens or to different epitopes of the same antigen, or combinations thereof), or multiple (>10) antibody specificities. In other words, the method is formatted to detect one, more than one, or multiple different antibodies in a single assay or experiment (e.g., by putting different antigens and/or epitopes of an antigen (a panel of antigens and/or epitopes) in different wells of a single plate or assay substrate, so that the assay screens a single sample for as many different antibodies as is useful). In addition, the assay can be formatted to screen multiple subjects in a high-throughput manner, in order to obtain information regarding a population of subjects.

The method of the present invention has several different uses. The method of the invention can be used to detect antibodies in a sample for any useful purpose, including both clinical (e.g., diagnostic, prognostic, and therapeutic) and research purposes. The method of the invention can be performed using human or non-human animal samples. First, the method can be used to diagnose T1D, or more importantly the potential to develop or time to onset of development of T1D, in a subject. The subject can be an individual who is suspected of having T1D, who is known to be predisposed to T1D, or an individual who is presumed to be healthy, but who is undergoing a routine or diagnostic screening. The subject can also be an individual who has previously been diagnosed with T1D and in whom treatment has been initiated, and who is now under surveillance for progression of T1D. The terms "diagnose", "diagnosis", "diagnosing" and variants thereof refer to the identification of a disease or condition on the basis of its signs and symptoms. As used herein, a "positive diagnosis" indicates that the disease or condition, or a potential for developing the disease or condition, has been identified. In contrast, a "negative diagnosis" indicates that the disease or condition, or a potential for developing the disease or condition, has not been identified.

In another embodiment of the invention, the method can be used to select a patient who is predicted to benefit or not benefit from a therapeutic procedure for T1D. Similarly, the method can be used to indicate or contraindicate a particular therapeutic procedure for a specific patient. In this embodiment, the method generally includes the steps of: (a) performing the method of the present invention for detection of an antibody as described in detail herein; (b) comparing the level of the antibody in the patient sample to a control level of the antibody selected from the group consisting of: (1) a control level of the antibody that has been correlated with responsiveness to the therapeutic procedure; and (2) a control level of the antibody that has been correlated with non-responsiveness to the therapeutic procedure; and (c) selecting the patient as being predicted to benefit from the therapeutic procedure, if the level of the antibody in the patient's sample is statistically more similar to the control level of the antibody that has been correlated with responsiveness to the therapeutic procedure than to the control level of the antibody that has been correlated with non-responsiveness to the therapeutic procedure; or (d) selecting the patient as being predicted to not benefit from the therapeutic procedure, if the level of the antibody in the patient's sample is statistically more similar to or less than the level of the antibody that has been correlated with non-responsiveness to the therapeutic procedure than to the control level of the antibody that has been correlated with responsiveness to the therapeutic procedure. For example, such a method can be useful to indicate or contraindicate administration of an anti-inflammatory agent in the patient or the administration of an agent that selectively targets ZnT8 or another autoantigen or expression thereof. Other aspects of this embodiment will be apparent to those of skill in the art.

A positive diagnosis or prognosis with respect to detection of an antibody using the method of the invention indicates that the antibody is present in the sample at a level that is statistically significantly above an experimentally determined or predetermined negative or "normal" level of the antibody in a sample of the same type (i.e., the "normal" level is a level of antibody detection that is found or is an average of what is found in subjects who do not have T1D). In order to establish a positive diagnosis or prognosis, the level of antibody detected in the test sample is increased over the established or determined baseline by an amount that is statistically significant (i.e., with at least a 95% confidence level, or $p<0.05$). Methods of standardizing, or creating an "index" of levels of antibody in a sample, are known in the art. A negative diagnosis or prognosis with respect to detection of an antibody using the method of the invention indicates that the antibody is either not detectable in the sample, or is present at a level that is not statistically significantly higher than (and can be lower than) a level that is statistically significantly above an experimentally determined or predetermined negative or "normal" level of the antibody in a sample of the same type.

Yet another embodiment of the invention includes a T lymphocyte assay, which detects the presence or absence of T cells in a subject that specifically bind to ZnT8. As with the antibody assays discussed above, this method of the invention can be used to effectively identify or select patients who, based on the level of T cell responsiveness against ZnT8 in the patient serum, are most likely to develop, or are developing, type I diabetes, including to predict factors such as time to onset, or monitor progression or stage of disease. The method can also be used to effectively identify or select patients who respond or do not respond to a particular therapeutic procedure (i.e., the method is used to indicate or contraindicate a therapeutic procedure for a particular patient).

In one aspect of this embodiment, the method includes detection of the isoepitopes described herein with respect to the ZnT8 polymorphisms. Assays can discriminate between small peptides, typically 8 to 20 amino acids in length that encode protein sequence that includes either variant regions of the molecule or invariant regions. Such T-cell responses are monitored typically in peripheral blood but could be applied to lymphocyte population obtained from other parts of the body. The analytical platform for such assays could be based on the proliferation, cytokine production or other markers of activation be they surface or intracellular protein markers or lipids or carbohydrates. Interpretation of these assays will usually also involve knowledge of the HLA class 1 and class 2 genotype of the individual.

In these embodiments of the invention, a ZnT8 antigen containing at least one ZnT8 T cell epitope is provided in an assay that detects ZnT8-specific T lymphocyte (T cell) responses in a test sample from a patient. ZnT8 proteins and antigens, including T cell epitopes, have been discussed in detail above. For example, in one embodiment, products of in vitro translation systems are useful in the present assays. The assay format can be any suitable T lymphocyte assay for an antigen, including, but not limited to, T lymphocyte proliferation assays, assays using MHC class I and II tetramer reagents, flow cytometry assays and ELISPOT assays. Accordingly, suitable assays can include cell-based assays and non-cell-based assays. In the latter case, soluble T cell receptors can be used, for example, in binding or immunoassays to detect ZnT8 antigens bound to soluble MHC molecules (e.g., tetramer reagents). In the former case, binding of antigen to T cell receptors on the surface of a cell is detected, typically by detecting proliferation of or cytokine production by the cell. Also as in the antibody assays, the T cell assays of the invention can be used to detect more than one or multiple autoantigens in a patient sample, and/or to detect T cell responses in multiple subjects.

As with the antibody assays, a positive diagnosis or prognosis with respect to detection of ZnT8 T cell responses indicates that ZnT8-specific T cells (autoreactive T cells) are present in the patient sample at a level that is statistically significantly above an experimentally determined or predetermined negative or "normal" level of such T cell responses in a sample of the same type (i.e., the "normal" level is a level of T cell responses that is found or is an average of what is found in subjects who do not have T1D). In order to establish a positive diagnosis or prognosis, the level of ZnT8-specific T cell responses detected in the test sample is increased over the established or determined baseline by an amount that is statistically significant (i.e., with at least a 95% confidence level, or $p<0.05$). Methods of standardizing, or creating an "index" of levels of ZnT8-specific T cell responses in a sample are known in the art. A negative diagnosis or prognosis with respect to detection of ZnT8-specific T cell responses using the method of the invention indicates that ZnT8-specific T cell responses are not detectable in the sample, or are present at a level that is not statistically significantly higher than (and can be lower than) a level that is statistically significantly above an experimentally determined or predetermined negative or "normal" level of such responses in a sample of the same type.

Included in the present invention are kits for performing any of the diagnostic methods as described above. The kit includes (a) a ZnT8 antigen (including any of the proteins, peptides, or mimetics described above) to be used in the assay in fluid phase or immobilized on a substrate (the antigen may be provided already immobilized or in a form suitable for immobilization); and (b) a reagent or reagents that are used to detect binding of an antibody to the antigen and/or a reagent or reagents that are used to detect binding of a T cell receptor to the antigen (in a cell-based or non-cell-based assay). Other reagents useful to perform the assay may also be included, such as, but not limited to, buffers, secondary antibodies, detectable labels and reagents useful for reading the assay, soluble binding proteins (e.g., soluble MHC, soluble T cell receptors), and other useful reagents.

Another embodiment of the present invention relates to the development and use of various reagents based on the identification of ZnT8 as an important autoantigen in therapeutic and preventative strategies to vaccinate a subject in order to prevent, delay or ameliorate the onset of type I diabetes in an individual, to suppress or destroy autoreactive T cell responses against the β cells of the pancreatic islets, and/or to modify an immune response against the β cells of the pancreatic islets from a destructive response to a less destructive or more protective response.

In one embodiment, ZnT8 proteins, peptides, homologues, mimetics, ZnT8 antibodies or antigen binding fragments thereof, and other ZnT8-derived or ZnT8-based agents (including chemically or physically modified forms of the peptide or antibodies) are administered ex vivo or in vivo to a subject in order to alter the course of T1D development or onset, and/or to induce a ZnT8-specific T lymphocyte response in the subject that is toleragenic or protective, rather than destructive. In one embodiment, such agents are administered as a vaccine. Such ZnT8-related agents/reagents have been described above.

In another embodiment, antigen-specific reagents based on ZnT8 that are designed to target ZnT8-specific autoreactive T cells are administered to a subject in combination with an agent that induces apoptosis in or is otherwise toxic to the T cells. This method can be performed in vivo or ex vivo. For example, soluble MHC molecules that form a peptide-binding groove (see, e.g., U.S. Pat. No. 5,820,866) are bound with a ZnT8 antigenic or toleragenic peptide (including altered peptides and homologues of ZnT8 that bind to MHC and can elicit a T cell response in accordance with this embodiment). Such complexes can be further complexed with (by any covalent or non-covalent technique) a toxin or other agent that will induce necrosis or apoptosis of T cells when the T cells bind to the MHC-peptide complex via their T cell receptors.

Toxins suitable for use in the present invention as agents to be complexed (conjugated, coupled) with ZnT8 peptides and homologues include any toxin or protein, agent or molecule that is toxic to a cell (necrotic or apoptotic), and include any toxin that can be used in a therapeutic setting as described herein. Such toxins include, but are not limited to, Fas ligand, pokeweed antiviral protein, botulinum toxin, ricin, etc.

Furthermore, the knowledge that can be obtained from the genetic, autoantibody and T-cell analyses described herein can be applied to making decisions on the use a specific therapeutic regime. Such a regime could be based on agents unrelated to ZnT8 or Slc30A8 or antigen specific agents such as recombinant ZnT8 protein, ZnT8 derived peptides either alone on linked with another agent, e.g. toxin, a cell such as a lymphocyte, a protein such as a HLA molecule or immunoglobulin) or Slc30A8 DNA either alone or linked with another agent. Treatment could be based on either the antigen or nucleic acids encoding it or inhibiting its expression, and could be tailored to either match the isoepitope or mismatch it depending on the desired outcome. Matching the isoepitope with the patient that has autoreactivity may be protective by induction of a state of tolerance. On the other hand, mismatching it would be a form of immunization which could also be harnessed for beneficial effects. It will be essential at the outset to know the isoepitope status of the individual as it will determine which path to follow and which isoform of the agent to use.

Such therapeutic approaches would be linked to diagnostic assays aimed at testing efficacy of the therapeutic agent. Such diagnostics would in some cases be a reiteration of the autoantibody and T-cell assays mentioned above; however some of the reagents that are generated may be applied to disease-specific objectives. For example, an isoepitope containing or encoding a therapeutic may be used to engage a B-lymphocyte with the view to expanding, activating or ablating the specific cell type. Efficacy of the treatment could be assessed by following the population of the target cell type and could, for example, use an isoepitope peptide coupled to an enzyme of fluorescent molecule to tag the β-cell population, which could then be enumerated and phenotypically characterized by flow cytometry. Such procedures could also be applied to the isolation of such cell population by panning procedures or fluorescence activated cell sorting.

The above-described agents for use in preventative and therapeutic methods of the invention can be administered alone, in a composition, formulation or vaccine, and/or in conjunction with the administration (together or sequentially) of other agents useful for prevention or treatment of T1D. As discussed above, a composition or agent of the present invention is administered to a patient in a manner effective to deliver the agent to a target cell or target site, so that the agent can act at the site and/or have an effect on the cell. Suitable administration protocols include any in vivo or ex vivo administration protocol. An effective administration protocol (i.e., administering a composition or agent of the present invention in an effective manner) comprises suitable dose parameters and modes of administration that result in the desired activity of the composition or agent in the subject or in the cell, such as tolerance of autoreactive T cells to the autoantigen ZnT8, apoptosis of autoreactive T cells, prevention or reduction of insulitis and/or destruction of the islet β cells, and prevention, delay in onset, or amelioration of severity of T1D. It is preferable that the patient obtains some measurable, observable or perceived benefit from such administration. Effective dose parameters can be determined by experimentation, for example, using in vitro cell cultures, in vivo animal models, and eventually, clinical trials if the patient is human. Effective dose parameters can be determined using methods standard in the art for a particular disease or condition that the patient has or is at risk of developing. Such methods include, for example, determination of survival rates, side effects (i.e., toxicity) and onset, progression or regression of disease.

Administration routes include in vivo, in vitro and ex vivo routes. In vivo routes include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one preferred embodiment of the present invention, a composition is administered by a parenteral route (e.g., subcutaneous, intradermal, intravenous, intramuscular and intraperitoneal routes). Intravenous, intraperitoneal, intradermal, subcutaneous and intramuscular administrations can be performed using methods standard in the art. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189: 11277-11281, 1992, which is incorporated herein by reference in its entirety). Oral delivery can be performed by complexing an agent or composition of the present invention to a carrier capable of withstanding degradation by digestive enzymes in the gut of an animal. Examples of such carriers, include plastic capsules or tablets, such as those known in the art.

Ex vivo refers to performing part of the regulatory step outside of the patient, such as by delivering an agent or composition to a population of cells (or contacting the cells with the agent or composition), where the cells have been removed from a patient, and returning the treated cells to the patient. Such cells could include, for example, T cells, wherein the T cells are induced to alter they type of immune response produced when contacted with ZnT8 in vivo. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell and/or target protein.

For proteins, small molecules (i.e., the products of drug design) or antibodies, a preferred single dose of such an agent typically comprises between about 0.01 microgram×kilogram$^{-1}$ and about 10 milligram×kilogram$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. Another particularly preferred single dose of an agent comprises between about 0.1 microgram×kilogram$^{-1}$ and about 10 microgram×kilogram$^{-1}$ body weight of an animal, if the agent is delivered parenterally.

A preventative or therapeutic benefit resulting from a method described herein is not necessarily a cure for a particular disease or condition (e.g., type I diabetes), but rather, can also encompass a result which most includes delay of onset of prediabetes or overt T1D or amelioration of the destructive aspect of the disease so that complete islet destruction is delayed for longer than would be expected in the absence of the treatment, thus allowing the patient a longer time to complete reliance on insulin therapy, other therapeutic interventions, and downstream detrimental health impacts of the disease. As used herein, the phrase “protected from a disease” refers to reducing the symptoms of the disease; reducing the occurrence or onset of the disease, and/or reducing the severity of the disease. Protecting a patient can refer to the ability of an agent or a composition of the present invention, when administered to a patient, to prevent a disease from occurring and/or to cure or to alleviate disease symptoms, signs or causes. As such, to protect a patient from a disease includes both preventing or delaying disease occurrence (prophylactic treatment) and treating a patient that has a disease or predisease (therapeutic treatment). The term, “disease” generally refers to any deviation from the normal health of a mammal and includes a state when disease symptoms are present, as well as conditions in which a deviation (destruction of islet (β cells) has occurred, but symptoms are not yet manifested.

Another embodiment of the invention relates to a method to identify a compound useful in a diagnostic assay as described herein, or in a preventative or therapeutic method of the invention as described herein. Such a method includes the steps of contacting a ZnT8-based agent (e.g., a ZnT8 nucleic acid molecule, protein or peptide, homologue, mimetic, or antibody or fragment thereof, or ZnT8-specific T cell receptor) with a putative regulatory compound, and detecting an interaction and/or effect resulting from the interaction between the putative regulatory compound and the ZnT8-based agent. Such assays can be cell-based or non-cell based. For example, one can identify antibodies and antigen-binding fragments thereof that selectively bind to ZnT8 using the ZnT8 proteins described above (including fragments and homologues thereof). One can use ZnT8 antibodies or ZnT8-specific T cell receptors to identify ZnT8 homologues, peptide mimetics, altered peptides, and fragments that will be useful in a diagnostic or therapeutic assay. ZnT8-based reagents can be used to design novel synthetic reagents, including mimetics, for use in the diagnostic or therapeutic methods described herein. One can also use ZnT8 nucleic acid molecules, proteins, peptides, mimetics or antibodies to identify various regulatory compounds that can suppress or alter an immune response to ZnT8 in an individual.

The steps of such a method generally include contacting a ZnT8-based agent with the putative regulatory compound, and measuring an effect on the ZnT8-based agent or cells in the assay, such as detecting ZnT8 mRNA transcription (e.g., by polymerase chain reaction (PCR), reverse transcriptase-PCR (RT-PCR), in situ hybridization, Northern blot, sequence analysis or detection of a reporter gene); detecting ZnT8 translation (e.g., by immunoblot, enzyme-linked immunosorbant assay (ELISA), radioimmunoassay (RIA), immunoprecipitation, immunohistochemistry and immunofluorescence); and/or detecting ZnT8 biological activity (e.g., by detecting any of the activities of ZnT8 as described herein, or by detecting the inhibition or suppression of such activities. Compounds detected in this method may be used in the diagnostic, preventative or therapeutic methods described herein.

According to the present invention, the methods and assays described herein are suitable for use in a patient that is a member of the Vertebrate class, Mammalia, including, without limitation, primates, livestock and domestic pets (e.g., a companion animal). Most typically, a patient will be a human patient.

The following examples are provided for the purpose of illustration and are not intended to limit the scope of the present invention. Each publication or other reference disclosed below and elsewhere herein is incorporated herein by reference in its entirety.

EXAMPLES

Example 1

The following example describes the initial identification of ZnT8 (also known as Slc30a8) as a novel diabetes autoantigen.

The inventors performed oligonucleotide microarray experiments using human U133 and mouse MOE430 Affymetrics chips that cover virtually the entire genome as well as the Panchip 5.0 that reports on gene transcripts in mouse pancreas. Data has been obtained from isolated islets from normal mice, diabetic models (NOD and ob/ob) and mice with deficiencies in the IAPP gene and Ngn 3 as well as from mouse pancreatic tumor cell lines (aTC1-6 glucagonoma, βTC3 and Min6 insulinomas and mPAC ductal tumor line). The data has been analyzed to highlight transcripts that display islet cell-type-specific expression, and their segregation between pancreatic α- and β-cells. Further analysis based on gene ontology (GO) annotation has been used to generate genelists both for human and mouse of candidate autoantigens. Of the 10 highest scoring candidates, 5 are known diabetes autoantigens and prompted the inventors to perform a proof-of-principle experiment on one of the high scoring transcripts (corresponding to ZnT8) as a target of humoral autoimmunity in new-onset T1D human subjects. A serological assay developed to this candidate detected immunoreactivity in 20% of diabetic subjects and none of the controls (<2.5%). The current proposal seeks to examine this and other gene candidates on these lists using assays of both humoral and cell-mediated autoimmunity Specifically, the advent of gene microarrays covering almost the complete spectrum of encoded mouse mRNAs (transcriptome) has enabled the identification of the subsets of genes that are expressed in pancreatic islets. A number of published studies have documented genes that are expressed in pancreatic islet tissue, specific islet cell types and islet-derived cell lines (67) (Shalev, 2002) (68). In addition, studies have reported on the responses of islets to physiological and pathophysiological manipulation such as stimulation with glucose or inflammatory cytokines in vitro, and from mice carrying mutant genes that affect pancreatic function or development. Unfortunately, much of this data is not currently accessible through central repository public domain databases or is on a variety of microarray platforms making data normalization difficult. The inventors have performed more than 50 microarray experiments using both human U133 and mouse MOE430 oligonucleotide chips that report on virtually all transcripts from each species. This includes data from normal mice, diabetic models (NOD and ob/ob) and mice with deficiencies in the IAPP gene and Ngn 3. The latter is completely devoid of pancreatic endocrine cells, and thus analysis at different gestational timepoints has allowed the identification of transcripts that are highly expressed in the endocrine cells relative to exocrine and ductal tissue throughout development (69). These data have been compared to array data and dbEST sequencing data from a large non-pancreatic tissue pool of 45 tissue types (Novartis dataset and Unigene expression profiles). Analysis of mouse pancreatic tumor cell lines (αTC1-6 glucagonoma, βTC3 and Min6 insulinomas and mPAC ductal tumor line) have further allowed the generation of predictive scores for select transcripts likely to display islet cell-type-specific expression, and their segregation between pancreatic α- and β-cells. These cell lines express genes related to the tumor cell phenotype and thus analyses were also performed on isolated pancreatic β-cell from a transgenic mouse expressing the autoantigen Phogrin linked to EGFP under the rat insulin 2 promoter. Table 2 lists some of the genes for which transcripts were defined by ANOVA analysis, firstly as being differentially expressed in Ngn3 wild-type and knock out mice at any embryological age (pancreatic endocrine and precursors) and secondly as being present in adult mouse islets. The list was then stratified on the basis of the relative expression in αTC and βTC cell lines. These approaches successfully predicted the islet cell specificity of the majority of the known transcriptional regulatory components involved in islet development, such as Ipf1, Arx, Pax4, Pax6, Brn4, NeuroD and known cell type specificity of several α- and β cell genes. Known neuroendocrine transcripts such as PTPRN (IA-2), prohormone convertases (Pcsk1, Pcsk2, Cpe) and the granins (Chga, Chgb Scg2, Sgne1) were in a pool of common αTC and βTC transcripts. Genes associated with other islet endocrine cells were, as predicted, not expressed in either (Ppy, Pyy, and ghrelin). There were some surprises among known genes, for example the appearance of the Williams Beuren syndrome chromosomal region 14 gene as a transcript showing β-cell specificity. This transcription factor is an important regulator of glycolytic and gluconeogenic enzymes and associated with a form of type 2 diabetes of hepatic origin (70). It is commonly considered as broadly distributed. Follow up using in situ hybridization analyses (data not shown) indicated that, indeed, the transcript is found in region of the developing pancreas where endocrine cells appear and in the adult pancreas is confined to islets with a distribution consistent with β-cell specificity.

TABLE 2

Gene transcripts that were depleted in the Ngn3 ko pancreas at e12.5, e15.5 or e18.5 were examined for expression in the endocrine cell lines αTC and βTC and adult islets.

| >5-fold enriched in αTC | >5-fold enriched in βTC | Not enriched in αTC or βTC | Not expressed in αTC or βTC |
|---|---|---|---|
| 1110005D19Rik 1700040L02Rik 2310014L03Rik 2810431N21Rik 2900052J15Rik 6430527G18Rik 6430527G18Rik 7420452D20Rik 9430022M17Rik 9430023B20 9530058B02Rik A630013F22Rik Apoa2 Arx B230206N24Rik B230309E09Rik B430319H24Rik Btg2 Cald1 Car2 CGl-141-pending Copg2as2 D6Ertd253e Ednra Eno2 Epb7.2 Fbp2 Fev-pending Foxf2 Galnt7 Gcg Gfra1 Glcci1 Gpr30 Gstt2 Hes1 Hs3st1 Ier3 Irx2 Itih2 Kap LOC224093 Mttp Pde3a Pde3a Pou3f4 Rbp4 Rgs4 Sbsn-pending Sdc4 Sdc4 Slc38a1 Soat1 Spp1 Tfpi Tle6 Trf Ttr 4930459B04Rik Ttyh1 Ttyh1 Vegfc Vldlr Zdhhc14 Zfp52. | 1100001E04Rik 1110035L05Rik 1700041C02Rik 1810018P12Rik 2010011I20Rik 2310007H09Rik 2610016M12Rik 2700049B16Rik 2900001G08Rik 3100002J23Rik 3110018A08Rik 3110050F08Rik 5830437M04Rik 5930418K15Rik 9330186A19Rik 9830147J24Rik A530058N18Rik A930001M12Rik A930009L07Rik Adcy7 Adra2a AI173274 AI315068 AI987662 Ang Asc-pending Atp2a3 AW125421 B630019K06Rik B930068K11Rik BC026600 BC052055 Bicc1 Bok Cat Cav2 Cd44 Crip Crp D930029E11Rik Dach2 Dcx Dpep1 Dpp4 Dscr1l1 Ebf3 Eif2s3y Elovl2 F13a Frabin-pending **G6pc-rs** Gch Gck Gipr Glp1r Gna13 Gpr27 H2-D1 Hlxb9 Hpca Hspa12a-pending **Iapp** **Ins1** **Ins2** Insm1 Ipf1 Iqgap1 Krt2-8 Lgals2 Lhx2 Lmwdsp20-pending LOC194126 LOC215866 LOC328644 Maob Mbc2 MGC47419 Myo7b Necab2-pending Nmi Nnat Npy Nudt7 Papss2 Papss2 Pclo Ppp1r1a Prcad-pending Prkcb Pvrl3 Ramp1 Rasd1 Rasgrf1 Sepp1 Slc12a7 Slc2a2 Slitl2 Stx3 Svil Sytl4 Tec Tnnt1 Ubap1 Wbscr14. | 7-Sep 9030612M13Rik 9830160H19Rik A430107J06Rik Abcc8 Aco1 Actr3 ank Aplp1 Atp1a1 AW011752 AW011752 Banf1 BC016198 BC042620 BC061928 C130083N04Rik C230068E13 C820002P14Rik Calm1 Capza2 Ccnb1 Ccnh Ccni Cda08-pending Cdc5l Cdkn2d Cgef2-pending Chga Chgb Chic1 Clcn3 Cotl1 **Cpe** Csnk1d D16lum22e D7Ertd743e D9Wsu20e Ddx9 Donson Dscr2 Emb Emb Foxa2 Gna11 Gng5 H2-D1 Hdac2 Hmgcr Hmgn3 Hmgn3 Hnrpab Hnrpu Hspa5 Ierepo4-pending Isl1 Khdrbs3 Kif11 Kif5b LOC218490 LOC226144 LOC231887 LOC240396 Map3k7 Matr3 Matr3 MGC65558 MGC6694 Mrps16 Mtch2-pending Ndr3 Neurod1 Nkx2-2 Np95 Paxip1 Pcsk1n Pcsk2 Pctk1 Pfdn1 Pitpnb Prnp Psk1-pending Psmb3 **Ptprn** Pttg1 Rab6 Rad21 Ramp2 Ranbp1 Rbpms Rcn2 Refbp2 Resp18 Risc-pending Rnpc2 Scg2 Sdfr1 Sfrs3 Sgne1 Smc4l1 Spi1-1 Sqle Ssb Syt13 Syt7 Syt7 Tmpo Tomm20-pending Txnrd1 Ube1c Ubl3 Ubqln2 Vdu1-pending Wwp4-pending Xlr3a Ywhab Ywhaz Yy1 Zfp364. | 1810044E12Rik 2310010I16Rik 2310067E08Rik 4731413G05Rik 5133401E04Rik 5730453H04Rik 5930418K15Rik 6430401D08 6720464I07Rik 8430421H08Rik 9030425P06Rik AA589382 Ace2 Acvr2 Apoa1 Arfgef1 Asah2 B230312I18Rik BC027756 BC054438 Braf C030034I22Rik C130047D21Rik C130099L13Rik C1qb C3 C430010P07Rik Cdw92 Ceacam2 Cfh Cpne3 Ctss Dnajc13 E130113K08Rik Ecm1 Enah Fabp1 Fabp4 Fbxl12 Fcgr2b Fgl2 Flt1 Foxa3 Frzb Gbp2 Gca Ghrl H2-Ab1 Hba-a1 Homez Hpvc2 Il6ra Insrr Jarid1c Klf9 LOC214424 LOC56628 Lyzs Lyzs Lyzs Mapk14 MGC25863 Mglap Mta3 Narg2 Ndel1 Nedd9 Nov Pah Pkhd1 Ppy Pyy Rbp7 Ret Rgpr-pending S100a6 S100a8 Scp2 Siat8c Sst Sycp3 Tacstd1 Timp3 Tm4sf3 Tnfrsf11b Tor3a Tpra40-pending Trim44 Tsll2-pending Usp15 Usp47 Utx Vcam1 Waspip Zfp219 Zfp36l1 Zfp40 Zfpn1a2. |

Components of islet endocrine cells are underlined; known autoantigens are highlighted in bold type.

Table 2 also shows distribution of known T1D autoantigens, highlighted in bold type. This relatively simple bioinformatic analysis showed insulin 1 and 2, IGRP (G6Pc-rs), IAPP and IA-2 (PTPRN) in their expected cellular locations but not GAD65. However the latter is not detected in mouse islets by most investigators, including the inventors, even though it is abundant in human islets (71). The above analysis underlines the fact that many autoantigens show cell type specificity. However that of itself is not sufficient to define a candidate, and thus the bioinformatic approach has been refined to take into account a number of features that are thought of as being attributes of autoantigen candidates and at the same time not exclude candidates based on a present/absent call. The model in essence takes into account the following features:

1. Autoantigens show specificity with the targeted cell, although this is not necessarily absolute.
2. The majority of autoantigens are expressed at moderate to high levels in the targeted cell.
3. T1D autoantigens appear to be physically associated with elements of the regulated secretory pathway.
4. Many of the targets of cell-mediated autoimmunity appear to be membrane associated.
5. Most are also expressed in peripheral antigen expressing cells of the thymus.
6. Several show tissue specific patterns of alternative splicing.

Features 1-4 can be evaluated based on the intersection of microarray datasets and annotation of the component genes. It is believed to be possible to derive an "autoantigenic index"

based on such data, although the amount of emphasis to place on particular structural, molecular biological and cell biological features as a contributor to antigenicity is under determination, as is the relative contribution to humoral-compared to cell-mediated responses. To address these issues, the inventors have compiled 2 sets of genes, one for mouse and one for human, based on abundance and specificity of expression to the endocrine pancreas (Table 3); the mouse data derived from the data in Table 2, the human data on expression data from the Novartis GeneAtlas of 79 human tissues (72). Analyses were performed in GeneSpring and GeneSpeed, the latter a protein domain database developed in the Barbara Davis Center in Denver, Colo. by Jan Jensen and colleagues.

Table 3

A: Mouse β-cell transcripts 308 transcripts were selected on the basis of their absence in Ngn3 null mouse pancreas, their presence in adult islets, and their presence in 13-TC cell lines. The Unigene EST expression database was interrogated with each of these genes to determine the frequency with which each gene was transcribed in 38 different mouse tissues, including pancreas (but not islets). The EST clonal frequency per million is tabulated along with the % of transcripts noted in pancreas compared to the total in all tissues (specificity). The product of the abundance and specificity was used to sort the data. Transcripts encoding known diabetes autoantigens are highlighted.

B: Human transcripts The Novartis custom oligonucleotide array representing 71 different human tissues was initially queried to determine which genes in the pancreatic islet dataset showed a significantly different signal from the median value of all other tissues (ANOVA cutoff <0.0002). The subset of these transcripts that displayed a signal 5 fold greater than that of the median of all tissues was filtered to remove transcripts showing low signal strengths (<200) and those that were expressed at higher levels in pancreas versus islets. The 140 genes which met these criteria were then used to interrogate the Unigene EST expression database to determine the frequency with which each gene was transcribed in 52 different human tissues including pancreas. The EST clonal frequency per million for pancreas (abundance) is tabulated along with the % of transcripts in pancreas relative to all tissues (specificity). Data were sorted on the Abu*Spec index. Transcripts encoding known diabetes autoantigens are highlighted.

| Name | Unigene | Rank | Abundance | Specificity | Abu*Spec |
|---|---|---|---|---|---|
| | | Mouse genes | | | |
| Ins2 | Mm.4946 | 1 | 8880.0 | 99.5 | 8834.2 |
| Ins1 | Mm.46269 | 2 | 8224.0 | 99.6 | 8190.1 |
| Iapp | Mm.415 | 3 | 4458.0 | 98.7 | 4400.7 |
| G6pc-rs | Mm.140768 | 4 | 282.0 | 94.6 | 266.9 |
| SLC30A8 | Mm.208831 | 5 | 151.0 | 100.0 | 151.0 |
| Pcsk2 | Mm.294493 | 6 | 765.0 | 18.2 | 138.9 |
| 2900001G08F | Mm.102196 | 7 | 173.0 | 64.8 | 112.1 |
| ERO1LB | Mm.326609 | 9 | 231.0 | 29.2 | 67.5 |
| EST | Mm.25089 | 10 | 71.0 | 63.4 | 45.0 |
| TM4SF4 | Mm.26618 | 11 | 127.0 | 34.1 | 43.4 |
| Ppp1r9a | Mm.332901 | 12 | 273.0 | 15.7 | 42.8 |
| PCSK1 | Mm.1333 | 13 | 98.0 | 36.6 | 35.8 |
| PTPrN | Mm.2902 | 14 | 346.0 | 10.2 | 35.2 |
| GNAS | Mm.125770 | 15 | 729.0 | 3.9 | 28.5 |
| EST | Mm.380993 | 16 | 160.0 | 17.6 | 28.2 |
| Iqgap1 | Mm.207619 | 17 | 328.0 | 7.5 | 24.5 |
| Supt16h | Mm.286066 | 18 | 200.0 | 12.2 | 24.3 |
| EST | Mm.156365 | 19 | 54.0 | 34.2 | 18.5 |
| GNG12 | Mm.234342 | 20 | 267.0 | 6.3 | 16.8 |

-continued

| Name | Unigene | Rank | Abundance | Specificity | Abu*Spec |
|---|---|---|---|---|---|
| Gipr | Mm.333633 | 21 | 54.0 | 29.7 | 16.0 |
| Rasgrf1 | Mm.44561 | 23 | 136.0 | 10.6 | 14.4 |
| Tmem54 | Mm.25295 | 24 | 100.0 | 13.6 | 13.6 |
| SGNE | Mm.4836 | 25 | 237.0 | 5.3 | 12.5 |
| PAPSS2 | Mm.203916 | 26 | 115.0 | 9.5 | 10.9 |
| PTPrN2 | Mm.206054 | 27 | 145.0 | 7.3 | 10.6 |
| Pcsk1N | Mm.4881 | 47 | 109.0 | 3.7 | 4.0 |
| ICA69 | Mm.275683 | 48 | 72.0 | 5.1 | 3.7 |
| Dmpk | Mm.6529 | 99 | 9.0 | 0.8 | 0.1 |
| | | Human genes | | | |
| INS | Hs.89832 | 1 | 15491.0 | 99.9 | 15470.0 |
| SGNE1 | Hs.156540 | 2 | 1884.0 | 50.7 | 955.7 |
| IAPP | Hs.46835 | 3 | 1670.0 | 51.2 | 854.7 |
| SLC30A8 | Hs.532270 | 4 | 830.0 | 81.7 | 678.1 |
| PCSK1N | Hs.522640 | 5 | 1026.0 | 42.9 | 439.9 |
| GNAS | Hs.125898 | 6 | 4600.0 | 9.4 | 434.2 |
| GAD65 | Hs.231829 | 7 | 356.0 | 75.9 | 270.2 |
| TM4SF4 | Hs.133527 | 8 | 565.0 | 43.3 | 244.4 |
| G6PC2 | Hs.283963 | 9 | 260.0 | 84.7 | 220.2 |
| CPE | Hs.75360 | 10 | 675.0 | 29.6 | 199.7 |
| CEL | Hs.533258 | 11 | 428.0 | 39.8 | 170.4 |
| NKX2.2 | Hs.516922 | 12 | 187.0 | 90.3 | 168.9 |
| ERO1LB | Hs.558519 | 13 | 424.0 | 29.6 | 125.4 |
| CHGB | Hs.516874 | 14 | 784.0 | 14.8 | 116.1 |
| PCKS2 | Hs.315186 | 15 | 433.0 | 23.9 | 103.4 |
| IPF1 | Hs.32938 | 16 | 91.0 | 100.0 | 91.0 |
| INSM1 | Hs.89584 | 17 | 187.0 | 46.2 | 86.3 |
| PAX6 | Hs.591993 | 18 | 292.0 | 28.9 | 84.3 |
| SCGN | Hs.116428 | 19 | 187.0 | 42.7 | 79.8 |
| PCSK1 | Hs.78977 | 20 | 214.0 | 28.5 | 61.0 |
| APLP1 | Hs.74565 | 21 | 328.0 | 15.5 | 50.7 |
| SCG3 | Hs.232618 | 22 | 177.0 | 23.4 | 41.5 |
| CFTR | Hs.489786 | 23 | 200.0 | 20.5 | 40.9 |
| SCG2 | Hs.516726 | 24 | 282.0 | 14.0 | 39.6 |
| KRT17 | Hs.2785 | 25 | 2276.0 | 1.7 | 38.0 |
| PTPrN | Hs.89655 | 26 | 150.0 | 18.1 | 27.2 |
| PTPrN2 | Hs.490789 | 44 | 187.0 | 6.3 | 11.7 |
| ICA69 | Hs.487581 | 58 | 86.0 | 5.7 | 4.9 |
| GAD67 | Hs.420036 | 96 | 4.0 | 0.5 | 0.0 |

In both cases the known diabetes autoantigens appear high on the list and even minor humoral autoimmune targets such as ICA69 and GAD67 are in the top 100 candidates. The transcripts on both lists overlapped considerably and their relative abundance and tissue specificity was similar with the exception of GAD65 which is poorly expressed in mouse islets compared to humans. Many of the proteins in the top 100 are secretory granule proteins or membrane proteins associated with the secretory pathway as determined by examination of the gene ontology (GO) functions in SWISS PROT, Prosite, and EPCONdb databases.

Figure 1:
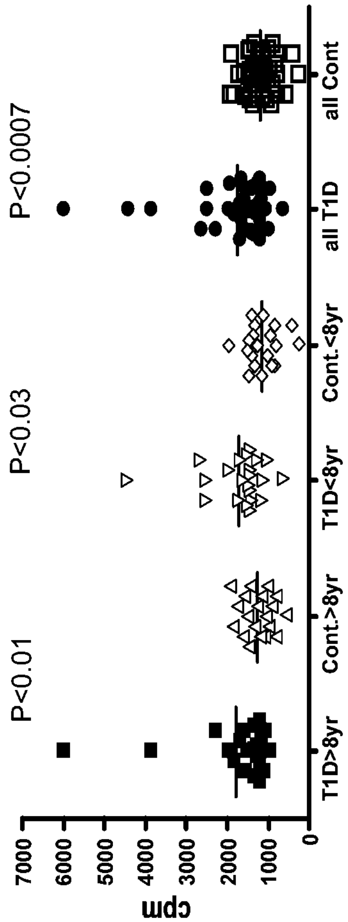

To address the question of whether these genelists can actually predict autoantigenic targets, the inventors developed an immunoprecipitation assay for Slc30a8 (now known as ZnT8), a transmembrane cation transporter that appears high on both the mouse and human genelist as a transcript of moderate abundance but high tissue specificity. A radioimmunoprecipitation assay was developed using in vitro translation of the cloned sequence and human sera from 44 new onset subjects prior to insulin therapy and 40 age- and HLA-matched controls (FIG. 1). Specifically, Slc30A8 was amplified from human islet cDNA and cloned into pcDNA3 directional topo vector, sequence verified and used as a template (0.5 μg) in a reticulocyte lysate in vitro translation reaction with 5 μCi $^{35}$S methionine. Human serum samples (5 μl) were incubated overnight at 4° C. with 20,000 dpm of the translation product in 50 μl Tris buffered saline containing 0.1% NP40. Immobilized Protein A was added to each incubation and the immunoglobulin-bound radioactivity isolated by filtration and determined by scintillation counting.

Nine of the T1D serum samples showed significant binding above levels observed with control serum (Mann Whitney non-parametric 2 tailed test) reaching as high as 50% of the radioactive ligand presented in the assay. Autoantibodies were present both in early onset (<8 years of age) and older patients (>8 years). Of the 9 positive patients, 6 also tested positive for insulin autoantibodies, 5 for GAD and 6 for IA-2. Slc30a8 would appear to be an independent disease marker.

The further development of diagnostic serological assays and assays for cell mediated autoimmunity requires the production of antigens which are at least functionally pure, folded in a native conformation and free from mitogenic impurities. This is not a trivial issue, especially for transmembrane proteins like Slc30a8 and IGRP that tend to be toxic to bacteria and eukaryotic cells when overexpressed.

In the case of IGRP, the inventors have previously been able to express high levels of antigen in a native form by stably transfecting *Drosophila* S2 cells using a construct driven by a regulated metallothionein promoter. Crude membrane fractions (CMF) from such cells have been tested with a IGRP-reactive T-cell hybridoma clone that was generated by fusion of draining lymph node cells from IGRP immunized NOD mice with BWZ36 lymphoma lines which stably express LacZ under control of the IL-2 promotor (73).

Figure 2B:
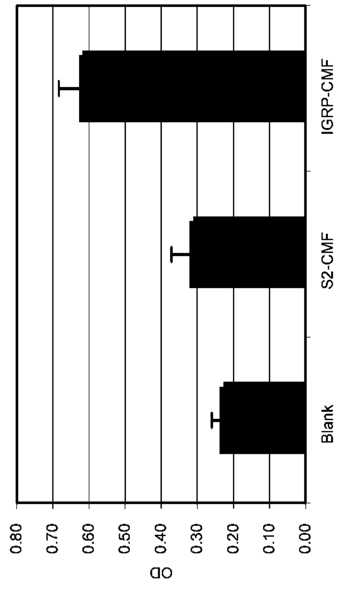
Figure 2A:
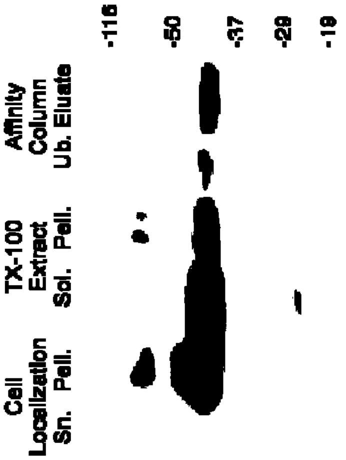

For example, in the digitized image shown in FIG. 2A, S2 cells were stably transfected with mIGRP V5 His construct and expression was induced by 0.5 mM Cu and cell membrane fraction (CMF) blotted with anti V5 antibody. The protein was efficiently extracted with TX-100, bound to metal chelate affinity column and eluted with imidazole under non-denaturing conditions. FIG. 2B is a graph showing a response assay for IGRP-CMF T cell hybridomas (clone 1-76-54). T cell hybridomas ($2\times10^5$ cells/well) were incubated overnight with irradiated NOD splenocytes as APCs ($1\times10^6$ cells/well) and antigen (IGRP-CMF or S2-CMF, 10 μg protein/well). β-galactosidase activity was assayed spectrophotmetrically. FIGS. 2A-3B demonstrate that IGRP production is tightly regulated by the metallothionein promoter (FIG. 2A) and that crude membrane fractions can be processed by mammalian APCs to induce an IGRP-specific response from the IGRP reactive T-cell hybridoma clone (FIG. 2B) measured spectrophotometrically with chloro-phenol red-β-galactoside as substrate. The combination of insect cell expression of putative antigen with either T-cell proliferation or hybridoma activation assays provides a generic yet robust set of standard operating protocols that should be adaptable to a variety of proteins, including soluble and membrane constituents and those that require glycosylation and other post-translational modifications.

Example 2

The following example describes assays to identify additional targets of humoral and cell-mediated autoimmunity by further evaluating the shortlist of potential candidates in Table 3 (see Example 1).

Initially, for unfamiliar candidates and molecules represented only as ESTs, full length clones are obtained, and in situ hybridization analyses are performed on human and mouse pancreas tissue to verify their expression in the β-cell.

Screening Candidate Antigens by Serological Analyses in Human Subjects.

These assays are best performed in human subjects since they are likely to show a wider spectrum of autoimmune responses because of the genetic diversity and complexity of immune response genes. Large numbers of samples also can be screened per day using semiautomated procedures in 96 well format at low cost per sample. The Barbara Davis Center has archived tens of thousands of samples that are well annotated and analyzed with respect to HLA haplotype, autoreactivity to molecules associated with T1D (insulin, GAD65, IA2, phogrin), celiac disease (transglutaminase IgA) and polyendocrine disease including affecting adrenal cortex (21β-hydroxylase for Addisons (74)) and thyroid (TSH receptor (75)). More than 20,000 sera from new onset patients are available, along with lesser numbers of samples from identical twins discordant for T1D and serial samples obtained from first degree relatives of diabetic patients spanning disease stages from antibody negativity, to single and multiple antibody positivity, and disease onset.

Two types of assay are initially developed based on radioimmunoprecipitation and time resolved fluorescence detection (TRF) methods respectively. Both assays require cloning and expression of the candidate antigen, and the inventors have taken a generic approach starting either with reverse transcribed mRNA or a certified MGC plasmid which will serve as PCR templates using primers designed to insert the sequence into an Invitrogen GATEWAY entry vector. From the entry vector the sequence can be directed to in vitro translation, generation of bacterial recombinant protein, adenovirus or baculovirus production through single step recombination.

For the radioprecipitation assay, cDNA cloned under a CMV promoter will be used as template (0.5 μg) in a coupled transcription/translation reaction (TNT kit; Promega) using reticulocyte lysate and 5 μCi $^{35}S$ methionine. Serum samples (5 μl) in 96 well plates are incubated overnight at 4° C. with 20,000 dpm of the translation product in 50 μl Tris buffered saline containing 0.1% NP40. Immobilized Protein A is then added to each incubation to capture immunoglobulin-bound radioactivity that is then recovered by filtration and radioactivity determined by scintillation counting. Positive and negative reference sera are run in each assay to achieve standardization and normalization.

For the TRF assay, the cDNA is expressed as a histidine tagged construct in *E. coli* or insect cells as appropriate and purified by metal chelate chromatography. 96 well plates are coated with the purified protein (1-10 μg/ml), blocked and then incubated with serum overnight at 4° C. in 50 μl Tris buffered saline containing 0.1% NP40. Immunoglobulin binding to the plate is determined using mouse anti human IgG conjugated to Europium (DELFIA) and time-resolved fluorescence measurement at an acidic pH (Victor 2 multichannel counter). In both types of assays, controls will be performed with preabsorption of the antibodies with recombinant antigen to test for specificity and to rule out heterophilic antibody artifacts. In the case of membrane-associated antigens it may prove necessary to work with domain-specific constructs rather than full-length molecules however this can be readily achieved by designing primers to amplify specific domains and cloning in the same way as described above.

The initial objective will be to screen a bank of 190 new onset T1D sera and 190 matched controls to establish the specificity and sensitivity of each assay using receiver operator curve analysis to determine acceptable cutoffs and Mann Whitney non-parametric tests to establish statistical significance (Prism software; Graphpad Inc.). A positive result with diabetic sera will be followed up by further optimization of the assay procedure to minimize background and maximize signal/noise. A truly negative result (low background and signal/noise of 1) can be further followed by modifying the assay, for example by introducing pancreatic microsomes in the in vitro translation assay. Assays with low disease specificity can sometimes be improved by concerted efforts to reduce noise in the assay by using constructs without hydrophobic domains, different blocking agents, different immunoglobulin capture procedures and by matching test sera with samples preabsorbed with recombinant antigen. The amount of effort directed to troubleshooting will obviously depend on the nature of the problem and the indication of whether disease-specific autoreactivity is suspected. Promising assays will be followed up by application to other available clinical samples to answer the questions of when in the natural history of disease does the autoreactivity occurs, the overlap of autoreactivity with other autoantigens, and whether there is an association with the age or HLA status of the patients. A number of publications from the inventors' laboratory and the Barbara Davis Center serve as template for such studies (76; 77).

Screening of HLA-DR3, -DR4 and -DQ8 Transgenic Mice for Cell-Mediated Immune Responses to the Candidate Antigens.

The inventors' previous data show that HLA-DQ8$^+$ I-A$\beta^{o/o}$ mice on a B10.M background can mount CD4$^+$ T-cell recall responses to the phogrin epitope peptides 2 and 7, and that the same peptides are targeted by peripheral T-cells in human new onset patients many of whom have the DR4/DQ8 haplotype (78). These previous studies supported the prediction that the human HLA-DQ8 has similar binding specificity to mouse I-A$^{g7}$, and that the -DQ8 molecule could present antigen in the context of either mouse or human co-stimulatory and accessory molecules. They affirm the utility of the mouse transgenic models as a means of identifying epitopes that are relevant to disease in humans even when the HLA transgenes are not carried on a strictly diabetes-susceptible background. To evaluate the full spectrum of T-cell epitopes from any candidate antigen that may be presented by MHC susceptibility loci in type 1A diabetic humans, the T-cell recall responses after immunization with the human recombinant protein are analyzed using transgenic HLA-DQ8, -DR3 (DRB1*0301) and -DR4 (DRB1*0401) mice as representing known diabetes susceptibility loci and HLA-DR2 (DRB1*1502) as a control for a "protective" class II molecule without diabetes association.

Animals: Several strains of HLA-DR and -DQ transgenic mice have been generated to evaluate the role of these molecules in shaping the immune response in diseases such as T1D, experimental autoimmune encephalitis and systemic lupus erythematosus (79; 80). The inventors have obtained HLA-DQ8$^+$ I-A$\beta^{o/o}$, -DR2, -DR3 and -DR4 transgenic mice from Dr. Chella David, Department of Immunology, Mayo Clinic, Rochester, Minn. and established colonies of these in our center. A second HLA-DR4 line with a human CD4 has recently been obtained from Dr. Greta Sonderstrup, Stanford University and the numbers are currently being expanded. The HLA-DQ8 (DQA1*0301/DQB1*0302) mice were produced with a genomic construct on an I-A$\beta^{o/o}$ I-Ea$^{o/o}$ background and thus produce HLA-DQ8 as the only class II molecule. A genomic-DR2 (DRB1*1502) and cDNA constructs of -DR4 (DRB1*0401) and -DR3 (DRB1*0301) are paired either with a mouse I-Ea or human DRa transgene. All transgenic animals are genotyped by PCR of DNA obtained from the tail for MHC expression and FACS analyses performed on PBMCs and splenocytes to establish the expression levels of the human transgenes and to monitor the expression of mouse MHC gene products.

Antigen presenting cells (APCs): Irradiated (20-35 Gy) syngeneic mouse splenocytes or DCs derived from bone-marrow will be used for in vitro stimulation of CD4$^+$ cells by co-incubation in the presence of protein antigen (1-100 μg/ml) or peptides (0.1-10 μg/ml). When used, DCs will be prepared from the marrow of tibias and femurs of 8-12 week old male mice after lavage with a 25 gauge syringe needle. Debris and large cellular aggregates are removed by filtration (70 μm mesh), erythrocytes lysed with $NH_4Cl$ and the cells resusupended in RPMI 1640 containing 10% heat inactivated endotoxin-free FBS and supplemented with antibiotics, pyruvate (1 mM), β-mercaptoethanol (50 μM) and 10 ng/ml GM-CSF. Non-adherent cells are removed from the culture on days 2 and 4 by replacement with fresh media and the loosely adherent cells recovered on day 6 (predominantly immature DCs with some contaminating monocytes and granulocytes). At this juncture the cells will be exposed for 24-48 h to recombinant antigen together with 0.1 μg/ml bacterial lipopolysaccharide (LPS) to induce "maturation" and upregulation of class II MHC molecules.

T-cell lines and hybridomas: T-cell lines and clones will be generated from the transgenic mice by the strategy we have used previously (78) that relies on immunization (5-100 μg recombinant antigen injected subcutaneously at the base of the tail in 50 μl CFA) to induce antigen-specific responses. T-cells will be harvested from the inguinal and periaortic lymph nodes 8-10 days post-immunization and tested for CD4$^+$ recall responses to the antigen preferably produced in an alternate vector system (i.e. immunize with His tagged antigen from S2 cells; recall with bacterial GST hybrid). Subsequently antigen-specific cells will used to generate T-cell hybridomas. T-cells will be subjected to a single round of in vitro stimulation before polyethylene glycol mediated fusion with the BWZ36 thymoma line which stably expresses LacZ under control of the NFAT elements from the IL-2 promotor (73). HAT-resistant lines will be propagated in RPMI/FBS, cloned by limiting dilution, and assayed by co-culture of $1\times10^5$ hybridoma cells with $1\times10^6$ syngeneic splenocytes in RPMI/FBS and antigen. After 16-24 h induced β-galactosidase will be measured using the soluble colorimetric substrate chloro-phenol red-β-galactoside (see FIG. 1), or in individual fixed hybridoma cells using X-Gal. To confirm MHC restriction, hybridomas will also be assayed using alternative APCs including splenocytes from non-transgenic mice of the same genetic background, and a panel of EBV-transformed B-lymphoblastoid cell lines that we are currently establishing from T1D and control organ donors; see (78). To ensure clonality and to evaluate clonal diversity, TCR usage will be determined by sequencing of cloned cDNA prepared from total RNA by inverse PCR (81).

The inventors' prior experience investigating T-cell responses to the cytoplasmic domain of phogrin in HLA-DQ8$^+$ and DR4$^+$ transgenic animals indicates that, assuming immunogenicity, responses to other antigens should be obtained in these animals, and that they will likely be informative. I-A$^{g7}$ and -DQ8 are functionally highly similar in terms of their ability to present related peptides, even though APCs bearing these molecules do not cross present to T-cells restricted to the orthologous molecule. Since the production of high affinity class-switched antibodies is a T-dependent process, it is anticipated that recall responses will be detected from animals immunized with antigens previously shown to elicit autoantibodies in the experiment described above. However, the converse is not necessarily true; antigens that do not show a humoral response may still be targets of cell-mediated immunity. The HLA-DR2 transgene is included in the present study as a class II molecule which is not associated with diabetes susceptibility and which might be linked to different epitopes that are not disease related. The inventors' previous experience suggests that they are more likely to obtain greater diversity of TCRs using hybridomas rather than T-cell clones, and so our initial focus will be to generate such reagents.

Unlike the NOD mouse, human diabetic subjects express multiple MHC class II molecules and a potential area of future study is to investigate various diabetes susceptibility or protective alleles in doubly-transgenic animals. HLA-DR3/-DQ8 animals, for example, develop a more severe insulitis (but not diabetes) and show enhanced spontaneous responses to GAD65 as compared to the parental animals (82; 83). Without being bound by theory, the inventors believe that they might also show increased responsiveness to a candidate autoantigen. Similarly, the effects of co-expressing HLA-DR3 and -DR4 or HLA-DR2 and -DQ8 could be examined.

Example 3

The following example describes additional experiments related to the identification of ZnT8 as a novel marker and target of diabetes autoimmunity.

The concept that the cDNA encoding ZnT8 might be of interest as a marker of diabetes autoimmunity arose from a bioinformatics analysis of microarray datasets from a gene knockout mouse (Ngn3 null) and comparison to patterns of tissue expression in other tissues (Example 1). Initially, the marker was annotated as the Unigene Mm.208831 corresponding to the Riken EST C820002P14, and was then recognized to correspond to ZnT8.

The inventors produced a full length ZnT8 and tested the protein in a radioimmunoprecipitation assay with new-onset diabetic serum in a series of experiments. Initial data indicates that 10% of patients showed reactivity, indicating that ZnT8 could be a novel autoantigen useful in diagnostic assays for type I diabetes.

The inventors then designed and produced a C-terminal fragment of ZnT8, corresponding to the final approximately 102 amino acids of the full-length molecule. Testing of this fragment in assays is summarized as follows.

Serum from 144 new onset T1D patients (ages 1 to 55 years of age; average age 11.9 years) was tested using the ZnT8 fragment, and 45% were seropositive in a radioimmunoprecipitation assay versus <1% in an age and HLA matched control population. Stratification by age showed that the antibodies showed a tendency to be higher in older individuals, with a peak of 70% in the group with diabetes onset at 12-15 years. The age profile was similar to that of other diabetes autoantigens, GAD65 and IA2, but appear later than for insulin antibodies. Autoreactivity to the new antigen showed no correlation with IAA, GAD and IA2 levels of autoreactivity, and is thus considered an independent marker.

Samples from 9 individuals who were followed from <1 year of age to onset of clinical diabetes were analyzed. These came from the sibling cohort of the DAISY study at the Barbara Davis Center. 8 of these individuals were seropositive during the course of prediabetes. Autoreactivity tended to appear later in the course of prediabetes and usually followed the emergence of GAD and insulin autoantibodies. The time of onset in some cases preceded or followed IA2 autoreactivity. In one of the subjects, anti-ZnT8 was the only antibody to be detected before the onset of disease, underlining the importance of the discovery of this new autoantigen.

8 new onset individuals who were negative for insulin GAD or IA2 antibodies were tested. Of this group, 2 tested positive for the new antigen, again reinforcing the concept that it has predictive value independently of existing markers.

Figure 5:
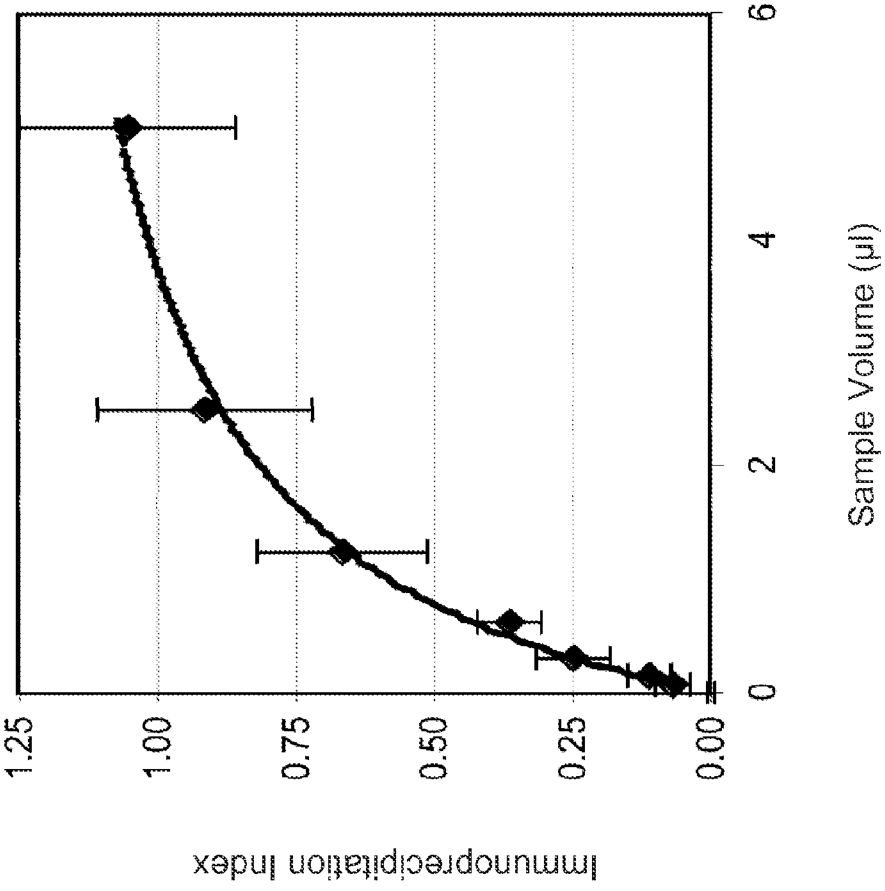
FIG. 5 illustrates the standard assay for ZnT8 C-term probe.

More specifically, referring to FIG. 5, this figure shows a standard assay for ZnT8 C-term probes. The curve depicts the mean±SD of a dilution series assayed in duplicate in 7 separate experiments. The experiments were performed over a period of 3 months and used different in vitro translation reactions. In vitro translated $^{35}$S-labeled probes (20000 cpm) were incubated overnight with 5 μl serum in 50 μl PBS pH7.4 containing 0.15% Tween 20, 1% BSA and 0.01% Na azide before addition of 20 μl a 50% by volume of Protein A agarose bead suspension. After 45 min the beads were recovered by filtration, washed 4 times then dried before the addition of 30 μl scintillation fluid and liquid scintillation counting. Comparable assays were developed for ZnT8 ORF and N-term probes. Positive sample: Pool of 9 new onset diabetic sera subject to doubling dilution in pooled control sera; Control sample: Pool of 9 age, gender and HLA matched samples from siblings of diabetics; Non specific binding: no serum addition. Assay conditions and data protocols for the data depicted in FIG. 5 were:

Probe addition 20,000 cpm/assay
Maximal immunoppt. 20591±4576 (7) cpm
Non specific binding 170 cpm; 0.83% of max.
Control 217±86 cpm expts)
Index=(sample-control)/(standard-control)
3SD cutoff: 293 cpm, Index=0.0055±0.0016 (7)
99th % cutoff: 286 cpm Index=0.0052
Intraassay CV: 2.3% (n=6)
Interassay CV: 18.6% (n=7).

Figure 6:
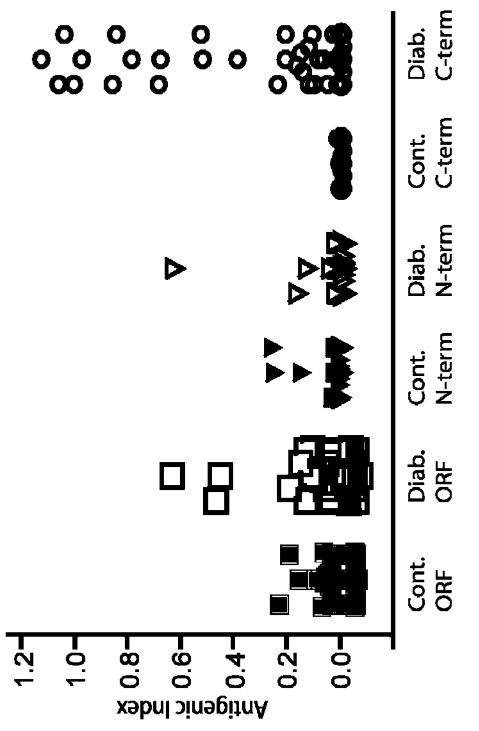
FIG. 6 is a graph showing results from a blinded DASP study with different ZnT8 constructs.

FIG. 6 shows the results of a blinded DASP study with different ZnT8 constructs. In vitro translated $^{35}$S-labeled constructs (20000 cpm) were incubated overnight with 5 μl serum in a 50 μl PBS containing 0.15% Tween 20, 1% BSA and 0.01% Na azide before addition of 20 μl a 50% by volume of Protein A agarose bead suspension. After 45 min the beads were recovered by filtration, washed 4 times then dried before the addition of 30 μl scintillation fluid and liquid scintillation counting. The immunoprecipitated radioactivity was expressed as the fraction relative to a standard prepared from pooled sera and a panel of 16 individual control sera as follows: Antigenicity index=(cpm test minus mean cpm control)/(cpm standard minus mean control). Assays were performed in triplicate. DASP provided 100 reference samples as controls and 50 matched new onset diabetic samples. The assay cutoff was defined as the index corresponding to the mean control +4SD and was respectively 0.1543, 0.1555 and 0.0129 for the ORF, N-term and C-term assays. Upon decoding this corresponded to the 98th, 998th and 99th percentile. On this basis 8%, 4% and 60% of the diabetic samples tested positive.

As illustrated in FIG. 6, a number of control sera consistently tested positive with the ORF and N-term assays. The assay was also less sensitive and showed a reduced signal to noise relative to the C-term assay. Although the difference between diabetic and control samples were significant in all assays (P<0.0001 Mann Whitney rank test), the most robust assay was that with the C-term construct (C4 probe SEQ ID: 24). The better performance of the C-term assay may be linked to better solubility of the probe (transmembrane domains absent) and/or the exposure of otherwise cryptic epitopes.

Figure 7:
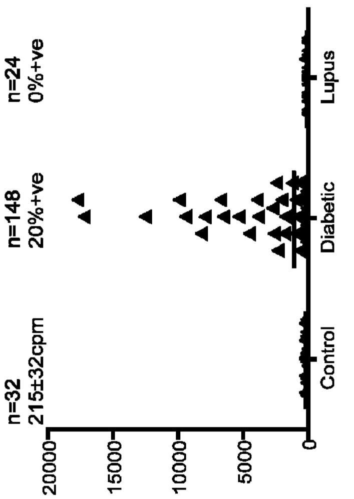
FIG. 7 is a graph demonstrating that ZnT8 detects autoantibodies in patients who are negative for ICA and gold standard biochemical antibodies.

The experiment shown in FIG. 7 shows that ZnT8 detects autoantibodies in patients who are negative for ICA and gold standard biochemical antibodies. The original gold standard for detection of diabetic autoantibodies is ICA (islet cytoplasmic antibodies) a complicated, tedious and relatively subjective assay that entails exposure of histological pancreatic sections from blood group 0 human subjects to sera followed by incubation with a fluorescently labeled second antibody and microscopic evaluation by a trained observer. It has not been fully replaced by the 3 biochemical antibody assays (Insulin GAD and IA2) since there are individuals who are ICA+ve yet biochemical antibody negative. Thus for the large Diabetes Prevention Trial 1 involving more than 60000 subjects, ICA was used as the procedure to define autoimmunity in a population of high risk first degree relatives of T1D patients.

Analysis of 30 new onset patient sera who were ICA-positive, but Insulin-, GAD- and IA2-negative showed that 24% were reactive to the ZnT8 C-term probe, suggesting that ZnT8 may be a component of the antibodies detected in the ICA assay. Even more remarkable is the finding that 30 (20.3%) of samples from individuals who were negative for ICA as well as insulin. GAD and IA2 tested positive for ZnT8 antibodies. This indicates that the epitope detected by the C-term probe is perhaps cryptic in the ORF molecule, a conclusion that was born out in subsequent studies. There is the potential that the reactivity to ZnT8 might not be related to generally to autoimmunity, but specifically to diabetes. A series of 24 samples of individuals who tested positive for anti-DNA antibodies were negative in the ZnT8 autoantibody assay.

Figure 8A:
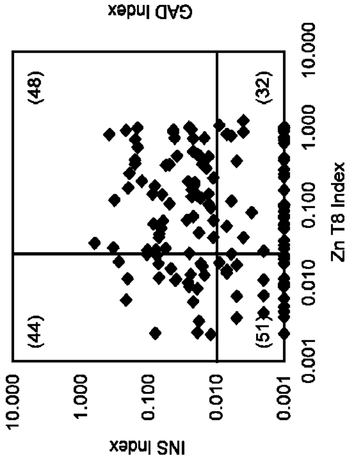
FIGS. 8A-8C is a series of graphs showing the relationship of autoantibodies to ZnT8 with respect to Insulin (FIG. 8A), GAD (FIG. 8B) and IA2 (FIG. 8C) in a new-onset population.
Figure 8B:
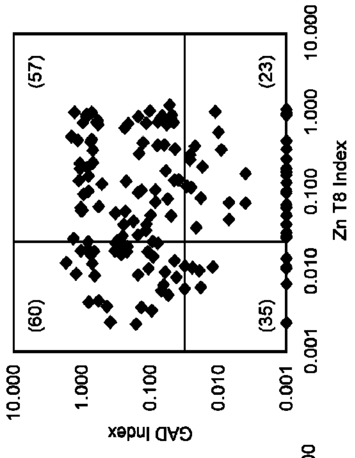
Figure 8C:
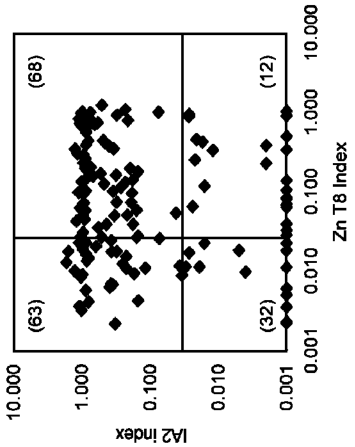

FIGS. 8A-C show the relationship of autoantibodies to ZnT8, with respect to each of Ins (FIG. 8A), GAD (FIG. 8B) and IA2 (FIG. 8C) in a new-onset population. In this experiment, the relationship between autoantibodies to the ZnT8 C-term probe was compared to the 3 gold standards. Data is derived from 175 new onset patients in BDC collection. Results are shown as antigenic index on a logarithmic scale to show the full range of the data and its overlap.

FIGS. 9A-9D shows the expression of autoantibodies at disease onset relative to age (FIG. 9A=ZnT8; FIG. 9B=GAD; FIG. 9C=Insulin; FIG. 9D=IA2). Specifically, this experiment shows that ZnT8 seropositivity is higher in older subjects at disease onset, whereas insulin autoreactivity falls. Data was derived from 237 subjects whose age at onset of diabetes ranged from 9 months to 18 years of age. Data was binned in 1 year intervals to derive a frequency profile as a function of age. ZnT8 C-term reactivity increased as a function of age of onset whereas insulin reactivity showed the expected decline as seen in published studies. GAD reactivity also tended to increase though not as dramatically. A marker that detects autoreactivity in older subjects compensates for the poor utility of insulin as a marker in older individuals. Post onset of disease insulin cannot be used as antibodies are generated to exogenous insulin used to treat the disease. This experiment demonstrates that ZnT8 antibodies should provide a good index to detect latent autoimmunity of diabetes with aging (LADA or type 1.5 diabetes) which is frequently misdiagnosed as type 2 diabetes in older subjects and treated inappropriately. In the US there are probably as many LADA patients as type 1 patients.

FIGS. 10A and 10B shows the results of an experiment investigating ZnT8 autoantibodies as a T1D predictive marker. A panel of samples from 43 individuals who had been followed from 9 months of age to diabetes were assayed retrospectively for autoantibodies to ZnT8 and the 3 gold standard antibodies to insulin, GAD65 and IA2. A series of results from 9 individuals are shown here as examples. Antibody reactivity is expressed as cpm with proband minus control divided by the standard deviation of the control response. Cutoff in the assay is defined by the gray area which is equivalent to 3SD or approximately 1% probability that a positive assay would be generated by chance. The patient shown in the FIG. 10A panels did not develop autoantibodies to insulin but tested positive at 1.5 years of age to IA2 and GAD. The IA2 antibodies were transiently expressed but returned at age 4. In the interim a high and sustained reactivity to ZnT8 developed. Thereafter IA2 antibodies returned and 5 years later the individual developed clinical diabetes. The patient shown in FIG. 10B did not develop autoantibodies to insulin, IA2 or GAD65 but did show ZnT8 Abs at age 2, 18 months prior to clinical disease.

FIG. 11 is a table showing diabetic autoantibody status at disease onset. The measurement of ZnT8 autoantibodies provides additional predictive power to the 3 gold standard autoantigens IA2, insulin and GAD65. Published studies show that the number of antibodies detected rather than the titer of antibodies is the strongest predictor of disease. Nevertheless, some people develop T1D without ever exhibiting antibodies to the 3 gold standard antibodies IA2, GAD65 and insulin. This indicates that there may be missing reactivities, a conclusion that is also born out by immunohistochemical assay of autoantigens which detect more patients than the combined measurement of INS, GAD and IA2 Abs. The ICA assay however is tedious and subjective. For an individual who exhibits only one of the gold standard antibodies the relative risk of developing disease in 5 years is low, however 2 or more antibodies suggests a bad prognosis and would be a indicator for therapeutic intervention if this were available. The upper portion of FIG. 11 shows the antibody status at clinical diagnosis of individuals who did develop diabetes. Results are from a blinded study of 50 new onset diabetic subjects and 100 age matched controls provided by the Diabetes Autoantigen Standardization Program and the data shown on the previous slides. With the addition of assays for ZnT8 autoreactivity the number of individuals who were antibody negative is lowered significantly from 14 to 8% and additionally 12% were designated as higher risk. Put another way, of the 7 individuals who would be rated as antibody negative, 43% actually had antibodies to ZnT8. Of 7 individuals in the "low risk" 1Ab group, again, 3 (43%) tested positive for ZnT8 antibodies putting them in a higher risk category.

Of the gold standard 3, insulin autoantibodies are difficult to measure and there is poor reproducibility with the assay between labs. If the insulin assay were discarded and replaced by the ZnT8 assay there would be the advantage that the number of 0Ab patients would still be reduced from 14 to 8% and there would be comparable numbers of double and triple positive patients. A longitudinal series would need to be performed to show that there was additional diagnostic power, but it is reasonable to assume that ZnT8/GAD/IA2 would be a better combination than INS/GAD/IA2. Moreover, it would be possible to avoid using $^{125}$I labeled ligand and to perform antigen preabsorption as needed for the anti-insulin assay.

The portion of FIG. 11 documents how the antibodies are distributed between patients in different categories. ZnT8C-term antibodies often appear as the only antibody in this group, similar to GAD again attesting to its predictive value. In a selected population of individuals who were ICA positive but negative for the 3 gold standard, 25% were ZnT8C-term positive.

FIGS. 12A and 12B shows receiver operator characteristics of the ZnT8 antibody assays. Data were derived from a combination of new onset patients at the Barbara Davis Center in Denver, Colo., and a sample set provided by DASP. The combination covered individuals ranging from 1.5 years to 59 years of age at onset. Cutoffs were determined from the 3SD limited of a group of 16 control sera corresponding. ROC plots were generated by comparison of the control and diabetic group in each case. FIG. 12A shows the immunoprecipitation index, and FIG. 12B shows the relationship between the sensitivity and specificity of each assay.

FIG. 13 shows the relationship between antibody reactivity to ZnT8ORF, C-term and N-term probes. Data were derived from a combination of new onset patients at the Barbara Davis Center and a sample set provided by DASP totaling 227 individuals. The top 50 C-term positive patients included the majority of individuals who tested positive for reactivity to the ZnT8 ORF and ZnT8 N-term probe. There was a significant correlation between the reactivity to the N-term probe and the ORF but not between the ORF and the C-term probe. This suggests that the epitopes involved in N-term reactivity are a subset of those detected by the ORF probe, but that the C-term picked up additional patients and was a better indicator of autoreactivity than the ORF translation product. This could arise because the ORF probe fails to fold correctly because the transmembrane region misfolds and distorts the folding of the normal C-term. The C-term could include additional epitopes some of which could be cryptic unless released from the intact molecule.

The experiment in FIGS. 14A and 14B investigates whether the N-term and C-term of ZnT8 interact to either generate a new epitope that depends on both domains or if N-term sequences can mask epitopes in the C-terminus.

The experiment was performed with 2 pools of diabetic serum that had a strong response to a C-term probe but either a low (FIG. 14A) or high N-terminal reactivity (FIG. 14B). With both mixes, it was apparent that the reactivity to the N-term and C-term were independent, and that the radioactivity immunoprecipitated when the probes were mixed was equivalent to the sum of the probes individually. Other variations on this experiment included the addition of Zn ions or chelation of endogenous Zn as a possible factor that might be involved in the interaction of these domains. The results were indistinguishable from those above suggesting that N- and C-term interactions did not affect immunoreactivity.

Referring to FIGS. 15A-15C, these figures show results from experiments aimed at localization of autoantibody epitopes in the C-terminus of ZnT8. FIG. 15A shows the aligned sequences of murine Slc30A8 (top; shown are positions 267-367 of SEQ ID NO:4), human Slc30A8 (middle; shown are positions 268 to 369 of SEQ ID NO:2) and murine Slc30A3 (bottom; sequence is SEQ ID NO:25). Since mouse Slc30A8 and Slc30A3 are not recognized by the majority of T1D sera, the data reveal that variant residues are likely to hold the key to predicting the epitope in the human Slc30A8 sequence. The inventors hypothesized that the final 11 amino acids (PDCLFCEDPCD; positions 359-369 of SEQ ID NO:2) might therefore be the antigenic epitope; however probes that deleted this region (BstN1 digestion, FIG. 15B; sequence referenced to show restriction sites is positions 336-369 of SEQ ID NO:2) were immunoprecipitated as efficiently as the wild type C-term by a pool of 9 diabetic sera (FIG. 15B). Trimming back another 6 amino acids reduced autoantibody binding, and trimming back 12 amino acids abolished antibody binding, suggesting that this region was especially important. The sequences for these probes are provided in Table 1 herein.

As shown in FIG. 15C, C-term probes were made with point mutations in charged residues (K340, H345 and E352) that potentially contribute to the antigenicity and to Serine 353 that is a putative phosphorylation site for casein kinase and potentially modified posttranslationally. When tested with the same pool of diabetic sera, it was evident that each of these residues contributed the immunoreactivity and proved to be additive in the mutant with all 3 charged residues were changed (AAA). The sequences for these probes are provided in Table 1 herein.

Further experiments were performed with overlapping 20 mer synthetic peptides covering this region as potential blocking agents (data not shown). Their ability to block binding was at best modest (<33% reduction), suggesting that the autoantibody epitope is probably conformational in nature and not a simple linear sequence. A further approach is to create chimeric molecules of Slc30A8 and Slc30A3 which retain the general conformation of the C-term region but allow critical sequences to be swapped in and out with disturbing the secondary structure. These chimeric molecules will also serve to map T-cell responses to the protein.

FIG. 16 shows residues in the C-term of ZnT8 that are critical for autoreactivity, and illustrates conservation of the defined epitope among animal species. Truncation and mutation mutants (described in Table 1 above) indicate that the core sequence SLTIQMES (positions 346-353 of SEQ ID NO:2) is critical for autoantibody reactivity to human Slc30A8 and that the individual residues E352 and S353 make important contributions to antibody binding. The overall sequence is well conserved in Slc30A8 different vertebrate species but less well in the closest mammalian homologues Slc30A2 and Slc30A3. The latter protein expressed as a C-term fragment is not detected by diabetic autoantibodies.

Interestingly, homologous sequences are observed in cation efflux proteins (other CzcD) from more distantly related bacterial species and in two unrelated proteins, a conjugation transfer protein from *E. coli* and the human REEP3. This raises the possibility that molecular mimicry could play a role in the development of autoreactivity to the zinc transporter in man or could contribute to antigen epitope spreading and bystander activation of the immune response.

In summary, ZnT8 is an independent serological marker of autoimmunity preceding type 1 diabetes, and is expected to be particularly useful in predicting the transition from ongoing autoreactivity to incipient diabetes.

The assay format described herein allows the screening of up to 500 samples per day and could be easily automated to increase its capacity. The fact that human subjects have autoantibodies to ZnT8 indicates that an autoreactive T-cell response is highly probable. This in turn means that additional diagnostic assays can be developed as described in detail above, as well as new therapeutic approaches to treatment and prevention of type I diabetes, also as described in detail above.

Example 4

The following example describes additional autoantibody epitope mapping of ZnT8 using deletion mutants and mouse/human chimeras.

In this experiment, the results of which are reflected in FIG. 17, the boundaries of the region incorporating the C-term autoantibody binding sites were mapped using a series of ZnT8 peptides in which the NH2 or COOH termini were truncated, or by making chimeras from human and mouse ZnT8 sequences, the latter being not being immunoreactive in the standard assay. The degree of overlap is depicted to scale and the extent of deletion shown as numbers of amino acids deleted (deletion diagrams) or the amino acid position number where the fusion proteins were stitched together, preceded by the amino acid as a single letter code (chimera diagrams).

The crystal structure of the *E. coli* Yiip cation efflux transporter was used to generate a 3-dimensional model of the human ZnT8 C-term using MODELLER (FIG. 18). Residues highlighted in light gray vary between the human and the mouse sequence, residues highlighted in medium gray were designated as poor antigenic candidates based upon immunological analysis of NH2 and COOH deletion constructs. The polymorphic residue at position 325 in human ZnT8 is shown in the spacefill model as the darkest gray residues (all positions in this figure are with respect to SEQ ID NO:2).

The major human polymorphic variants of ZnT8 in the Caucasian population, Trp325 and Arg325, lie distal to the membrane at the cytoplasmic pole of the structure and are surrounded for the most part by residues that are conserved between humans and mice. The Arg side chain extends into the solvent, whereas the Trp indole ring folds back on to the molecule so potentially creating a very different surface without distorting the overall fold. The Gln325 variant, although closer in geometry to the Arg side chain is predicted to result in rotation of the structure from around Ser353. A cluster of variant residues of the second alpha helical segment (aa328-341) whose topology is largely unaffected by the polymorphism were postulated to be a strong candidate for an epitope that was recognized equally by probes bearing the polymorphic variants. The adjacency and solvent exposure of Arg332, Glu333, Arg336 and Arg340 were notable in this regard.

Referring to FIG. 19, the conservation of ZnT8 residues in the regions targeted by T1D autoantibodies is shown. The N-terminus is the target for antibodies in approximately 5% of patients whereas up to 80% of T1D subjects show antibodies to the C-terminus. Constructs at the start and end of the C-terminus have been made to map the boundaries of the epitopes in the C-term. The area shaded in gray is where most of the autoreactivity is focused. Comparison of the Znt8 sequence of mice, humans and toads indicate that much of the epitope region is conserved, with the exception of amino acids 322-341 (referring to SEQ ID NO:2). This region incorporates a major polymorphic variant in humans (325R or 325W) that is not found in other species.

Example 5

The following examples describes experiments related to embodiments of the invention directed to polymorphisms in the ZnT8 gene and protein.

Mouse ZnT8 C-term differs from human ZnT8 at 18 amino acids out of 104 and is not reactive with new onset diabetic sera. Constructs based on the mouse sequence were generated in which the variant amino acids were substituted for their human counterparts either singly or in multiples. The results of this experiment are shown in FIGS. 21A-21C. Each data point is the mean of 2-7 responses determined with human sera that had been previously categorized as being restricted either to the human Arg325 (CR) or Trp325 (CW) polymorphic variant or reactive to an equal extent to human Arg325, Trp325 or Gln325 (CQ) variants. The amino acid numbering references the human sequence positions (SEQ ID NO:2).

The results showed that a change of amino acid 325 to its human counterpart restored binding by CR- and CW-restricted sera but only with the corresponding amino acid. No single amino acid change restored reactivity of CQ responding sera. However, the combined substitution of amino acids 332, 333, 336 and inclusion of an amino acid missing in the mouse sequence at aa340 restored reactivity. It was further enhanced by inclusion of Arg at position 325.

FIGS. 22A-22D show that multisite mutation of mouse ZnT8 recapitulates human ZnT8 reactivity. In this experiment, FIG. 22A shows that a single point mutation of the mouse sequence, while still able to detect a number of human Arg-reactive antibody responses, does not react to the majority of sera. However, further mutation of 4 residues based on differences in human and mouse structures (REKK mutants) now rendered the mouse sequence almost as reactive as the human Arg 325 native structure (FIG. 22B). The same probe was not seen by the majority of hTrp reactive sera (FIG. 22D). The same sera reacted weakly with the mTrp only probe (FIG. 22C).

In a further experiment, illustrated in FIGS. 23A-23D, ZnT8 from 171 new onset T1D subjects was assayed with mQ>R325, mQ>W325, hR325, hW325 and hQ325 probes, and the data was calculated relative to rabbit anti C-term antibody (BUN-E). 32 individuals exhibited hArg325-restricted antibody binding, 19 of whom showed responses to mArg325 probes. 13 showed hTrp325-restricted antibody binding, 10 of whom showed responses to mArg325 probes. Binding to mArg325 or mTrp325 was not observed in the absence of the human counterpart. The Arg325 restricted responses correlated between human and mouse and were of a similar magnitude after correction for binding represented by hQ325 probe. The binding of the mTrp325 probe, while mapping onto the hTrp325-restricted response, was of a lesser magnitude even after correction for hQ325 binding. These data indicate that the amino acid at position 325 is a determinant of the autoantibody epitope specificity, and in the case of the Arg variant, the mouse point mutant resembles the native human conformation.

In another experiment, the ZnT8 autoantibody response in new onset T1D patients was determined with variants of amino acids 325. Mutant C-terminal probes based on the Arg, Trp and Gln variants ZnT8 325 were used to determine the humoral immune response in 300 new onset patients. FIG. 24D shows the level and frequency of the response segregated on the basis of the response to individual probes or probe combinations. FIG. 24C shows the relationship between the responses to the common Arg and Trp variants and is divided in 5 sectors based on a 95th percentile cutoff for Trp (vertical) and Arg (horizontal) only responses and diagonals representing the boundaries equivalent responses ±3SD to both probes assuming a 15% CV in the assay. FIGS. 24A and 24B uses the same stratification in examining the relationship between the responses to the Gln probe and the Arg and Trp probes.

FIG. 25 shows the relationship between ZnT8 autoantibody specificity and patient genotype (SNP rs13266634) for the codon at amino acid 325. Newly diagnosed T1D subjects were genotyped with TaqMan probes and sera assayed with human ZnT8 C-term constructs incorporating Gln (Q), Arg (R) or Trp (W) at aa325. Assay cutoffs were set at an index of 0.02. In the cases where signal between the R or W exceeded that of the Q probe it was assumed that the CV of the respective measurements was 15% and designated as having dual reactivity positive if indices differed by >3SD.

There is a number of important conclusions to be drawn from this data:

1) Reactivity to the Gln probe (hCQ) is relatively unaffected by genotype, whereas the Arg reactivity (hCR) is more prominent in individuals with the C allele (Arg encoding) and Trp activity with the T allele (Trp encoding).
2) Only one individual of 300 was shown to react to hCQ probe but not hCW or hCR. The individual possibly encodes a Gln residue at aa325 (nucleotide sequencing analysis). Individuals who show a restricted response to Arg (Arg only) all had the encoding C-allele. Individuals who shows a restricted response to Trp (Trp only) all had the encoding T-allele. The same was essentially true for individuals who showed hCR and hCW reactivity that exceeded hCQ reactivity.
3) Individuals who showed reactivity to hCR and hCW but not hCQ were principally heterozygous.

These data are summarized in FIG. 26, which shows the correlation between genotype and reactivity to the hCR and hCW probes. More particularly, FIG. 26 summarizes the principal findings that reactivity restricted to the Arg325 epitope is strongly associated with the C allele and particularly the CC genotype, and conversely that antibody reactivity restricted to the Trp325 epitope is associated with the T-allele and particularly the TT genotype.

FIG. 27 shows the Slc30A8 genotype in relation to age of diabetes onset. There is no obvious correlation between the genotype and the age at which T1D is diagnosed. However, more samples would be required to conclude, for example, that individuals with TT genotype are less likely to develop the disease before the age of 6, although the trend is there and the conclusion is an important one in terms of intervention.

There is some distortion of the genotype in the present inventors' diabetic population versus that reported in the literature for control subjects. The inventors observe 56.8% CC, 35.1% CT and 8.1% TT (n=285). The reported genotype frequency in a European population is 52.3% CC, 44.1% CT and 3.6% TT (n=168) P=0.05 Fisher exact test. The allele frequency of 74.4% C and 25.6% T however is identical in both populations. The distribution of genotypes is not markedly different from the Hardy Wienberg distribution (55.33% CC, 38.11% CT and 6.56% TT). The differences are more apparent if one looks at the heterozygotes vs homozygous TT (P=0.026) and might suggest that there are more TT genotypes and fewer heterozygotes.

Population studies do not report the existence of T1D associated genes on chromosome 8 in the region where Slc30A8 is located. A genome-wide SNP analysis nevertheless shows an association of Slc30A8 T allele with type 2 diabetes and such an association required the analysis of around 8000 subjects to detect show an odds ratio of around 1.2 and a P<0.05.

An interesting feature of the combined immunological and genetic data was the observation that the prevalence of Arg-restricted antibodies was higher in the CC homozygous group than the heterozygotes, and likewise, the Trp-restricted antibodies were higher in the TT homozygous group than the heterozygotes. This could in part be a gene dosage effect with more antigen expression being associated with more autoreactivity.

In FIGS. 28A-B, the level of autoantibody reactivity is shown relative to the probe used and the Slc30A8 genotype. The CC genotype is represented by 169 samples, the CT by 108 and the TT by 23. The ZnT8 hC Gln probe is predicted to reflect antibody binding to the REKK epitope alone, whereas the hC Arg probe binds both to this epitope and the epitope centered on Arg 325 residues. The hC Trp probe reports on both REKK binding and the epitope centered on Arg 325. The mean levels and prevalence of hCArg reactivity was affected by genotype in the expected direction, i.e. increasing reactivity associated with the C-allele frequency (Arg 325 encoding) (FIG. 28A). Likewise, the mean levels and prevalence of hCTrp reactivity increased with the T-allele frequency (Trp325 encoding) (FIG. 28A). The hC Gln reactivity tended to increase with the C-allele though not significantly with respect to either prevalence or level (FIG. 28A). Reactivity to the other biochemical autoantibodies, IAA, GADA and IA2A were not affected by the Slc30A8 genotype (FIG. 28B).

Experiments summarizing the current state of development of ZnT8A assays is shown in FIG. 29. Assays were performed on a series of blinded samples provided by the Diabetes Autoantigen Program (DASP) from the Center of Disease Control (CDC) comprised of 50 new onset diabetes patients and 99 controls. Assays were performed using the basic radioimmunoprecipitation format with in vitro translated $^{35}S$ methionine radiolabeled probes based on either mouse (m) or the human (h) ZnT8 sequences All probes incorporated the C-terminal 104aa (C) of ZnT8 with a Gln (Q) (SEQ ID NO:50), Arg (R) (SEQ ID NO:49), of Trp (W) (SEQ ID NO:51) at the human amino acid position 325. In addition, probes were generated by fusion of the N-terminal 74aa (N) of ZnT8 to the C-terminus using a linker sequence of 3 glycine residues e.g hNCW or by creating a dimer of the C-terminus that had a hCW construct linked to a hCR construct through a flexible linker arm (SEQ ID NO:52) to generate the hCWR construct (SEQ ID NO:60). The linker arm was derived from the immunoglobulin heavy chain sequence that is known to provide a flexible connection between the constant and variable regions of its sequence. The linker (sequence PSTPPGSSGGG; SEQ ID NO:52) potentially allows a single antibody molecule to bind with higher avidity as it can connect at 2 sites to the probes. Alternatively, the probe can bind 2 antibody molecules simultaneously including immunoglobulins of different epitope specificity.

The results which are obtained with exactly the same samples illustrate many of the current state of the art and features of diabetic autoreactivity namely:

1) The low reactivity of human T1D autoantibodies towards the native mouse sequence (SEQ ID NO:40) compared to its human counterpart (hCQ) (SEQ ID NO:50) {mCQ vs hCQ}.

2) Increased binding of antibodies to mouse ZnT8 by a single point mutation that replaces the Gln residue at amino acid 324 (SEQ ID NO:41) (equivalent to human aa325) with an Arg residue (SEQ ID NO:49) {mCQ vs. mCR data}.

3) The differential reactivity towards human probes bearing a single amino acid change at position 325 {invariably the prevalence of autoantibodies at onset is in the order hCR>hCW>hCQ). This is because hCR (SEQ ID NO:49) and hCW (SEQ ID NO:51) probes have additional epitopes centered on position aa325 and because antibodies towards the Arg variant occurs more frequently than the Trp variant in the inventors population, which is largely Caucasian.

4) The fusion of the N-terminus with the C-terminus W (SEQ ID NO:62) or R (SEQ ID NO:63) variant introduces the potential of incorporating N-terminal epitopes recognized by 5-8% of the T1D population alongside the more reactive C-terminal ones. However the overall prevalence of antibodies measured in this way is actually lower than the C-term probes alone because the background and thus the cutoff in the assay is higher. Further engineering of the molecule will correct this.

5) Fusion of the CW and the CR domains into one molecule (SEQ ID NO:60) created a probe that detected autoreactivity in individuals who were reactive to CR, CW and CQ probes. Moreover the signal was higher in the diabetic subjects without any sacrifice in the background resulting in an assay with superior performance than a combination of 3 different assays. It is conceivable that further multimerization of the probe may increase detection levels even further. At 78% the detection rate is as high or higher than any other diabetic biochemical autoantibody marker.

FIG. 30 shows autoreactivity to different ZnT8 constructs combining N-term, C-term, luminal loops, cytosolic loops and polymorphic residues. hCTrp minus TM (SEQ ID NO:67) is a construct that incorporates the 3 extracellular (luminal) and 2 cytosolic loops that connect the 6 transmembrane domains, designed to capture any epitope that resides in these loops. It detected an extra 4% of new onset patients. hCArgN incorporates both the N- and C-termini but in the reverse order (SEQ ID NO:66). The levels of antibodies measured by this probe correlate with those measured with hCArg alone, but also captures some additional patients, particularly those showing low levels of reactivity. The data also illustrate that the polymorphism exchanging Arg for Trp at position 325 identifies a significant number of patients that are restricted in the antibody response to hCArg or hCTrp alone in addition to patients that reactive equally or independently of epitopes incorporating amino acid 325.

Example 6

The following example provides additional data relative to ZnT8 as a novel target and marker for type I diabetes.

FIGS. 31A-F shows results of a study in which autoantibodies to ZnT8 were compared to C-peptide (2 hour post prandial) and other autoantibodies over time in a group of 23 new onset T1D subjects. The principal result of this analysis is that autoantibodies to ZnT8 fall away post-disease onset with kinetics that are similar to the loss of beta cell mass as reflected in the fall off in C-peptide responses. This data led the inventors to suspect initially that there was genetic variation in the molecule as in FIGS. 31A-31C, responses to a C-term construct can be seen that are sometimes equivalent to a N—C fusion construct (FIG. 31A) or quite disparate (FIGS. 31B-C). When these probes were resequenced, it was shown that C-term was the Arg325 version (SEQ ID NO:49), and N—C the Trp325 version (SEQ ID NO:64) of the molecule. The polymorphic variants were introduced through the use of 2 different islet sources for the cloning or cloning of products from a heterozygous individuals. The mean annual decline in reactivity for C-term was 26±13%, N/C 28±9%, C-pep 32±14%, IA2 22±11 (±SD n=15). GADA by contrast increased by 42±191% possibly because there is another tissue source of this antigen.

FIG. 32 shows ZnT8A and C-peptide levels 5-10 yr post onset. A follow up from the previous study (described in Examples above) out to 10 years shows that antibodies declined consistently in individuals and that those with high levels initially were more persistent. Seroconversion occurred in around 60% samples by 5+ years and in all cases levels were down on average by 90%. Samples with low Ab levels (<0.4) tended to seroconvert sooner. Some samples with high levels of antibodies had residual beta cell mass as indicated by a positive random C-peptide.

Measurement of ZnT8 autoantibodies in addition to insulin, GAD and IA2 has been described in prior Examples herein. In those examples, the inventors only measured hCR reactivity, which would have excluded Trp325 reactivity. FIG. 33A further illustrates the concept as the change in detection rate (black with ZnT8; white without). FIG. 33B shows the differential effect of adding the ZnT8 antibody measurement.

Example 7

The following example describes autoantibody presadsorption experiments showing the utility of recombinant proteins to discriminate between different ZnT8 epitopes.

A number of recombinant ZnT8 molecules have been generated using vectors such as pGEX (produces Glutathione S transferase fusion protein that can be purified on glutathione agarose) or pQE series (produces polyhistidine tagged protein at N or C terminus of protein that can be purified by metal chelate chromatography). However, these proved to produce insoluble inclusion bodies which are difficult to purify and do not fold appropriately to recreate the autoantigenic epitopes. The inventors found a solution in using a vector (pET43.1 vector, Novagen, EMD Biosciences) that incorporates both a His tag for metal chelate affinity purification and a protein fusion partner that is a bacterial chaperone and ensures proper folding. The proteins are expressed in BL-21 (DE3) bacteria (Novagen).

NUS hZnT8 C-term proteins based on SEQ ID NO:49 (Arg325 variant), SEQ ID NO:50 (Gln325 variant), and SEQ ID NO:51 (Trp325 variant) were generated and purified on Ni chalate columns and 20 microgram samples incubated with T1D sera for 2 h at room temperature prior to the addition of 35S Met labeled hCArg, hCTrp and hCGln probes and performance of the conventional radioimmunoprecipitation assay.

In the experiment shown in FIG. 2C, three sera were selected that were known to be restricted to Arg 325 (serum #541827 designated hCArg), to Trp325 (serum #533855 designated hCTrp) and to react with epitopes shared by all hC-term constructs independently of the amino acid in position 325 (serum #BT designated hCGln), The results show remarkable specificity of the sera that are restricted to the epitopes defined by the polymorphism at position 325. The results also show that the Trp and Arg constructs cannot be discriminated by the 325 unrestricted sera. In practical terms, this provides a better means of determining the relative reactivity of a serum to Arg325, Trp325 and non-restricted epitopes when these are represented in the same sample. Currently, three radioassays using a single external pan-reactive C-terminal standard (BUN-E) are used to calibrate the responses, and then the numbers are subtracted from one another. With the availability recombinant proteins described herein, the level of reactivity can be determined using the one relevant probe and determining the degree to which the signal is squelched by different recombinant proteins.

Therefore, the availability of ZnT8-based fusion proteins, such as the hCNUS fusion proteins described herein, that show the expected epitope specificity, is an important step in the production of solid phase autoantibody assays that are based on non-isotopic procedures.

Example 8

The following example describes the production of adenoviral vector encoding hZnT8, and its expression in host cells.

The inventors have also produced adenoviral vectors for the expression of full-length hZnT8. Cos7 cells were transduced with control adenovirus (AdLacZ), or Ad-hZnT8-V5-His ( ) at an MOI of 100. 48 h later the cells were harvested and expression monitored by SDS-PAGE and immunoblotting with a polyclonal rabbit anti-hZnT8 (data not shown). β-glucuronidase (GUS) or hZnT8-V5-His were translated in vitro (RTS 100 wheat germ CECF kit, Roche) according to the manufacturer's instructions. 1 μl (2%) of the mix was analyzed by western blotting. Expression of the hZnT8 protein was detected (data not shown).

Example 9

The following example shows the immunohistochemical localization of ZnT8 in various cells.

The INS-1 cell is a beta cell line derived from pancreatic beta cells that provides a good cell culture model of the beta cell. The antibody used in the above analysis was raised to a recombinant fusion protein termed BUN-E and used to identify the intracellular localization of ZnT8 as encoded by the Slc30A8 gene. The antibody highlights intracellular punctate organelles of an approximate size of 0.2-0.5 microns (data not shown). These are distributed in the cell in a similar pattern to insulin that marks the insulin granule where previous studies have localized ZnT8. The inventors' immunohistochemical studies described in this example (data not shown) indicate that ZnT8 is not entirely in the granule but shows partial overlap with a transGolgi network marker TGN38. It does not localize with the early endosome marker EEA1 or with the recycling endosome as marked by the transferrin receptor however substantial overlap does occur with LAMP1 a marker of mature lysosomes. Overall, these data disagree with the previous report that ZnT8 is exclusively a secretory granule protein (Chimienti et al., supra).

Example 10

The following example shows that real time PCR of human fetal pancreas shows that ZnT8 has high islet specificity unlike related members of the gene family (ZnT1-7, and ZnT9).

Human fetal pancreas was obtained at the indicated ages, mRNA extracted and then used for determination of expression levels in the developing (9 and 23 weeks gestation) and adult islets. At 9 weeks, the pancreas is largely comprised of undifferentiated mesenchymal tissue. By 23 weeks the gross anatomy is similar to that of the adult and shows substantially increased expression of ZnT1 (Slc30A1) and especially ZnT8 (Slc30A8), see FIG. 34. Isolated islets have less ZnT1 since this is principally confined to the exocrine tissue.

Example 11

The following example demonstrates that newly diagnosed T1D patients show peripheral T-cell responses to ZnT8 synthetic peptides.

This experiment shows hZnT8-dependent IFN-γ production by PBMCs from newly diabetic subjects. PBMCs were isolated from 4 newly diabetic subjects and cultured for 48 h with pools of 2 consecutive hZnT8 peptides (10 μg/ml) that span the entire human ZnT8 sequence with 20 mer peptides overlapping by 7aa. After washing cells were transferred to ELISPOT plates coated with an anti-IFN-γ monoclonal and cultured for an additional 17 h. After washing to remove cells and media, secreted cytokine was detected using a second-site biotinylated anti-IFN-g monoclonal, GABA, and a precipitating silver solution. Spots were counted with a Bioreader 4000 Pro X (BIOSYS). The control subject did not give a significant signal (SI≥3) to any peptide, but showed SI=22 for a tetanus toxoid/diptheria toxin positive control. All patients tested, but not the control, gave significant IFN-γ responses (SI≥3) to at least 3 peptides, with subject NO3 responding to 12 of the peptide pools. Little correlation was observed between individuals, with only pool 17 (E5+F5) being recognized by all subjects.

REFERENCES

1. Wucherpfennig K W, Eisenbarth G S: Type 1 diabetes. *Nat Immunol* 2:767-768, 2001
2. Yoon J W, Jun H S: Cellular and molecular pathogenic mechanisms of insulin-dependent diabetes mellitus. *Ann N Y Acad Sci* 928:200-211, 2001
3. Rosmalen J G, van Ewijk W, Leenen P J: T-cell education in autoimmune diabetes: teachers and students. *Trends Immunol* 23:40-46, 2002
4. Rossini A A: Autoimmune diabetes and the circle of tolerance. *Diabetes* 53:267-275, 2004
5. Kukreja A, Cost G, Marker J, Zhang C, Sun Z, Lin-Su K, Ten S, Sanz M, Exley M, Wilson B, Porcelli S, Maclaren N: Multiple immuno-regulatory defects in type-1 diabetes. *J Clin Invest* 109:131-140, 2002
6. Arif S, Tree T I, Astill T P, Tremble J M, Bishop A J, Dayan C M, Roep B O, Peakman M: Autoreactive T cell responses show proinflammatory polarization in diabetes but a regulatory phenotype in health. *J Clin Invest* 113:451-463, 2004
7. Redondo M J, Yu L, Hawa M, Mackenzie T, Pyke D A, Eisenbarth G S, Leslie R D: Heterogeneity of type I diabetes: analysis of monozygotic twins in Great Britain and the United States. *Diabetologia* 44:354-362, 2001
8. Atkinson M A, Leiter E H: The NOD mouse model of type 1 diabetes: as good as it gets? *Nat Med* 5:601-604, 1999
9. Andre I, Gonzalez A, Wang B, Katz J, Benoist C, Mathis D: Checkpoints in the progression of autoimmune disease: lessons from diabetes models. *Proc Natl Acad Sci USA* 93:2260-2263, 1996
10. Kassem S A, Ariel I, Thornton P S, Scheimberg I, Glaser B: Beta-cell proliferation and apoptosis in the developing normal human pancreas and in hyperinsulinism of infancy. *Diabetes* 49:1325-1333, 2000
11. Rosmalen J G, Leenen P J, Pelegri C, Drexhage H A, Homo-Delarche F: Islet abnormalities in the pathogenesis of autoimmune diabetes. *Trends Endocrinol Metab* 13:209-214, 2002
12. Ziegler A G, Schmid S, Huber D, Hummel M, Bonifacio E: Early infant feeding and risk of developing type 1 diabetes-associated autoantibodies. *Jama* 290:1721-1728, 2003
13. Norris J M, Barriga K, Klingensmith G, Hoffman M, Eisenbarth G S, Erlich H A, Rewers M: Timing of initial cereal exposure in infancy and risk of islet autoimmunity. *Jama* 290:1713-1720, 2003
14. Hyoty H, Taylor K W: The role of viruses in human diabetes. *Diabetologia* 45:1353-1361, 2002
15. Larger E, Becourt C, Bach J F, Boitard C: Pancreatic islet beta cells drive T cell-immune responses in the nonobese diabetic mouse model. *J Exp Med* 181:1635-1642, 1995
16. Baker F J, Lee M, Chien Y H, Davis M M: Restricted islet-cell reactive T cell repertoire of early pancreatic islet infiltrates in NOD mice. *Proc Natl Acad Sci USA* 99:9374-9379, 2002
17. Yang Y, Charlton B, Shimada A, Dal Canto R, Fathman C G: Monoclonal T cells identified in early NOD islet infiltrates. *Immunity* 4:189-194, 1996
18. Tian J, Gregori S, Adorini L, Kaufman D L: The frequency of high avidity T cells determines the hierarchy of determinant spreading. *J Immunol* 166:7144-7150, 2001
19. Amrani A, Verdaguer J, Serra P, Tafuro S, Tan R, Santamaria P: Progression of autoimmune diabetes driven by avidity maturation of a T-cell population. *Nature* 406:739-742, 2000
20. Notkins A L, Lernmark A: Autoimmune type 1 diabetes: resolved and unresolved issues. *J Clin Invest* 108:1247-1252, 2001
21. Bowie L, Tite J, Cooke A: Generation and maintenance of autoantigen-specific CD8 (+) T cell clones isolated from NOD mice. *J Immunol Methods* 228:87-95, 1999
22. Haskins K, Portas M, Bergman B, Lafferty K, Bradley B: Pancreatic islet-specific T-cell clones from nonobese diabetic mice. *Proc Natl Acad Sci USA* 86:8000-8004, 1989
23. Nagata M, Santamaria P, Kawamura T, Utsugi T, Yoon J W: Evidence for the role of CD8+ cytotoxic T cells in the destruction of pancreatic beta-cells in nonobese diabetic mice. *J Immunol* 152:2042-2050, 1994

24. Wegmann D R, Shehadeh N, Lafferty K J, Norbury-Glaser M, Gill R G: Establishment of islet-specific T-cell lines and clones from islet isografts placed in spontaneously diabetic NOD mice. *J Autoimmun* 6:517-527, 1993

25. Gelber C, Paborsky L, Singer S, McAteer D, Tisch R, Jolicoeur C, Buelow R, McDevitt H, Fathman C G: Isolation of nonobese diabetic mouse T-cells that recognize novel autoantigens involved in the early events of diabetes. *Diabetes* 43:33-39, 1994

26. Castano L, Russo E, Zhou L, Lipes M A, Eisenbarth G S: Identification and cloning of a granule autoantigen (carboxypeptidase-H) associated with type I diabetes. *J Clin Endocrinol Metab* 73:1197-1201., 1991

27. Martin S, Lampasona V, Dosch M, Pietropaolo M: Islet cell autoantigen 69 antibodies in IDDM. *Diabetologia* 39:747, 1996

28. Buschard K, Josefsen K, Horn T, Fredman P: Sulphatide and sulphatide antibodies in insulin-dependent diabetes mellitus. *Lancet* 342:840, 1993

29. Lieberman S M, Evans A M, Han B, Takaki T, Vinnitskaya Y, Caldwell J A, Serreze D V, Shabanowitz J, Hunt D F, Nathenson S G, Santamaria P, DiLorenzo T P: Identification of the {beta} cell antigen targeted by a prevalent population of pathogenic CD8+ T cells in autoimmune diabetes. *Proc Natl Acad Sci USA* 100:8384-8388, 2003

30. Eisenbarth G S, Moriyama H, Robles D T, Liu E, Yu L, Babu S, Redondo M, Gottlieb P, Wegmann D, Rewers M: Insulin autoimmunity: prediction/precipitation/prevention type 1A diabetes. *Autoimmun Rev* 1:139-145, 2002

31. Serreze D V, Fleming S A, Chapman H D, Richard S D, Leiter E H, Tisch R M: B lymphocytes are critical antigen-presenting cells for the initiation of T cell-mediated autoimmune diabetes in nonobese diabetic mice. *J Immunol* 161:3912-3918, 1998

32. Kelemen K, Wegmann D, J C H: T cell epitope regions on phogrin and IA-2 in the NOD mouse. *Diabetologia* 43:A98, 2000

33. Wegmann D R, Norbury-Glaser M, Daniel D: Insulin-specific T cells are a predominant component of islet infiltrates in pre-diabetic NOD mice. *Eur J Immunol* 24:1853-1857, 1994

34. Zekzer D, Wong F S, Ayalon O, Millet I, Alfieri M, Shintani S, Solimena M, Sherwin R S: GAD-reactive CD4+ Th1 cells induce diabetes in NOD/SCID mice. *J Clin Invest* 101:68-73, 1998

35. Wong F S, Karttunen J, Dumont C, Wen L, Visintin I, Pilip I M, Shastri N, Pamer E G, Janeway C A, Jr.: Identification of an MHC class I-restricted autoantigen in type 1 diabetes by screening an organ-specific cDNA library. *Nat Med* 5:1026-1031, 1999

36. Daniel D, Gill R G, Schloot N, Wegmann D: Epitope specificity, cytokine production profile and diabetogenic activity of insulin-specific T cell clones isolated from NOD mice. *Eur J Immunol* 25:1056-1062, 1995

37. Chen W, Bergerot I, Elliott J F, Harrison L C, Abiru N, Eisenbarth G S, Delovitch T L: Evidence that a peptide spanning the B-C junction of proinsulin is an early Autoantigen epitope in the pathogenesis of type 1 diabetes. *J Immunol* 167:4926-4935, 2001

38. Nakayama M, Abiru N, Moriyama H, Babaya N, Liu E, Miao D, Yu L, Wegmann D R, Hutton J C, Elliott J F, Eisenbarth G S: Prime role for an insulin epitope in the development of type 1 diabetes in NOD mice. *Nature* 435: 220-223, 2005

39. DiLorenzo T P, Graser R T, Ono T, Christianson G J, Chapman H D, Roopenian D C, Nathenson S G, Serreze D V: Major histocompatibility complex class I-restricted T cells are required for all but the end stages of diabetes development in nonobese diabetic mice and use a prevalent T cell receptor alpha chain gene rearrangement. *Proc Natl Acad Sci USA* 95:12538-12543., 1998

40. Trudeau J D, Kelly-Smith C, Verchere C B, Elliott J F, Dutz J P, Finegood D T, Santamaria P, Tan R: Prediction of spontaneous autoimmune diabetes in NOD mice by quantification of autoreactive T cells in peripheral blood. *J Clin Invest* 111:217-223, 2003

41. Herold K C: Achieving antigen-specific immune regulation. *J Clin Invest* 113:346-349, 2004

42. Daniel D, Wegmann D R: Protection of nonobese diabetic mice from diabetes by intranasal or subcutaneous administration of insulin peptide B-(9-23). *Proc Natl Acad Sci USA* 93:956-960, 1996

43. Wolfe T, Bot A, Hughes A, Mohrle U, Rodrigo E, Jaume J C, Baekkeskov S, von Herrath M: Endogenous expression levels of autoantigens influence success or failure of DNA immunizations to prevent type 1 diabetes: addition of IL-4 increases safety. *Eur J Immunol* 32:113-121, 2002

44. Kaufman D L, Clare-Salzler M, Tian J, Forsthuber T, Ting G S, Robinson P, Atkinson M A, Sercarz E E, Tobin A J, Lehmann P V: Spontaneous loss of T-cell tolerance to glutamic acid decarboxylase in murine insulin-dependent diabetes. *Nature* 366:69-72, 1993

45. Tisch R, Yang X D, Singer S M, Liblau R S, Fugger L, McDevitt H O: Immune response to glutamic acid decarboxylase correlates with insulitis in non-obese diabetic mice. *Nature* 366:72-75, 1993

46. Petersen J S, Karlsen A E, Markholst H, Worsaae A, Dyrberg T, Michelsen B: Neonatal tolerization with glutamic acid decarboxylase but not with bovine serum albumin delays the onset of diabetes in NOD mice. *Diabetes* 43:1478-1484, 1994

47. Tian J, Clare-Salzler M, Herschenfeld A, Middleton B, Newman D, Mueller R, Arita S, Evans C, Atkinson M A, Mullen Y, Sarvetnick N, Tobin A J, Lehmann P V, Kaufman D L: Modulating autoimmune responses to GAD inhibits disease progression and prolongs islet graft survival in diabetes-prone mice. *Nat Med* 2:1348-1353, 1996

48. Ramiya V K, Shang X Z, Wasserfall C H, Maclaren N K: Effect of oral and intravenous insulin and glutamic acid decarboxylase in NOD mice. *Autoimmunity* 26:139-151, 1997

49. Ablamunits V, Elias D, Cohen I R: The pathogenicity of islet-infiltrating lymphocytes in the non-obese diabetic (NOD) mouse. *Clin Exp Immunol* 115:260-267, 1999

50. Mukherjee R, Wagar D, Stephens T A, Lee-Chan E, Singh B: Identification of CD4+ T cell-specific epitopes of islet-specific glucose-6-phosphatase catalytic subunit-related protein: a novel beta cell autoantigen in type 1 diabetes. *J Immunol* 174:5306-5315, 2005

51. Kelemen K, Wegmann D R, Hutton J C: T-cell epitope analysis on the autoantigen phogrin (IA-2beta) in the non-obese diabetic mouse. *Diabetes* 50:1729-1734, 2001

52. Panagiotopoulos C, Qin H, Tan R, Verchere C B: Identification of a beta-cell-specific HLA class I restricted epitope in type 1 diabetes. *Diabetes* 52:2647-2651, 2003

53. Van Vliet E, Roep B O, Meulenbroek L, Bruining G J, De Vries R R: Human T cell clones with specificity for insulinoma cell antigens. *Eur J Immunol* 19:213-216, 1989

54. Roep B O, Arden S D, de Vries R R, Hutton J C: T-cell clones from a type-1 diabetes patient respond to insulin secretory granule proteins. *Nature* 345:632-634, 1990

55. Neophytou P I, Ozegbe P, Healey D, Quartey-Papafio R, Cooke A, Hutton J C: Development of a procedure for the direct cloning of T-cell epitopes using bacterial expression systems. *J Immunol Methods* 196:63-72, 1996
56. Arden S D, Roep B O, Neophytou P I, Usac E F, Duinkerken G, de Vries R R, Hutton J C: Imogen 38: a novel 38-kD islet mitochondrial autoantigen recognized by T cells from a newly diagnosed type 1 diabetic patient. *J Clin Invest* 97:551-561, 1996
57. Kallan A A, Roep B O, Arden S D, Hutton J C, de Vries R R: Beta-cell reactive T-cell clones from type I diabetes patients are not beta cell specific and recognize multiple antigens. *J Autoimmun* 8:887-899, 1995
58. Benoist C, Mathis D: Autoimmunity provoked by infection: how good is the case for T cell epitope mimicry? *Nat Immunol* 2:797-801, 2001
59. Atkinson M A, Bowman M A, Campbell L, Darrow B L, Kaufman D L, Maclaren N K: Cellular immunity to a determinant common to glutamate decarboxylase and coxsackie virus in insulin-dependent diabetes. *J Clin Invest* 94:2125-2129, 1994
60. Roep B O, Hiemstra H S, Schloot N C, De Vries R R, Chaudhuri A, Behan P O, Drijfhout J W: Molecular mimicry in type 1 diabetes: immune cross-reactivity between islet autoantigen and human cytomegalovirus but not Coxsackie virus. *Ann N Y Acad Sci* 958:163-165, 2002
61. Honeyman M C, Stone N L, Harrison L C: T-cell epitopes in type 1 diabetes autoantigen tyrosine phosphatase IA-2: potential for mimicry with rotavirus and other environmental agents. *Mol Med* 4:231-239, 1998
62. Harkonen T, Lankinen H, Davydova B, Hovi T, Roivainen M: Enterovirus infection can induce immune responses that cross-react with beta-cell autoantigen tyrosine phosphatase IA-2/IAR. *J Med Virol* 66:340-350, 2002
63. Rudy G, Stone N, Harrison L C, Colman P G, McNair P, Brusic V, French M B, Honeyman M C, Tait B, Lew A M: Similar peptides from two beta cell autoantigens, proinsulin and glutamic acid decarboxylase, stimulate T cells of individuals at risk for insulin-dependent diabetes. *Mol Med* 1:625-633, 1995
64. Baekkeskov S, Nielsen J H, Marner B, Bilde T, Ludvigsson J, Lemmark A: Autoantibodies in newly diagnosed diabetic children immunoprecipitate human pancreatic islet cell proteins. *Nature* 298:167-169, 1982
65. Baekkeskov S, Aanstoot H J, Christgau S, Reetz A, Solimena M, Cascalho M, Folli F, Richter-Olesen H, De Camilli P: Identification of the 64K autoantigen in insulin-dependent diabetes as the GABA-synthesizing enzyme glutamic acid decarboxylase. *Nature* 347:151-156, 1990
66. Bonifacio E, Lampasona V, Genovese S, Ferrari M, Bosi E: Identification of protein tyrosine phosphatase-like IA2 (islet cell antigen 512) as the insulin-dependent diabetes-related 37/40K autoantigen and a target of islet-cell antibodies. *J Immunol* 155:5419-5426, 1995
67. Cardozo A K, Heimberg H, Heremans Y, Leeman R, Kutlu B, Kruhoffer M, Orntoft T, Eizirik D L: A comprehensive analysis of cytokine-induced and nuclear factor-kappa B-dependent genes in primary rat pancreatic beta-cells. *J Biol Chem* 276:48879-48886, 2001
68. Lilla V, Webb G, Rickenbach K, Maturana A, Steiner D F, Halban P A, Irminger J C: Differential gene expression in well-regulated and dysregulated pancreatic beta-cell (MIN6) sublines. *Endocrinology* 144:1368-1379, 2003
69. Gradwohl G, Dierich A, LeMeur M, Guillemot F: neurogenin3 is required for the development of the four endocrine cell lineages of the pancreas. *Proc Natl Acad Sci USA* 97:1607-1611, 2000
70. Iizuka K, Miller B, Uyeda K: Deficiency of carbohydrate-activated transcription factor ChREBP prevents obesity and improves plasma glucose control in leptin-deficient (ob/ob) mice. *Am J Physiol Endocrinol Metab* 291:E358-364, 2006
71. Kash S F, Condie B G, Baekkeskov S: Glutamate decarboxylase and GABA in pancreatic islets: lessons from knock-out mice. *Horm Metab Res* 31:340-344, 1999
72. Su A I, Wiltshire T, Batalov S, Lapp H, Ching K A, Block D, Zhang J, Soden R, Hayakawa M, Kreiman G, Cooke M P, Walker J R, Hogenesch J B: A gene atlas of the mouse and human protein-encoding transcriptomes. *Proc Natl Acad Sci USA* 101:6062-6067, 2004
73. Malarkannan S, Mendoza L M, Shastri N: Generation of antigen-specific, lacZ-inducible T-cell hybrids. *Methods Mol Biol* 156:265-272, 2001
74. Bednarek J, Furmaniak J, Wedlock N, Kiso Y, Baumann-Antczak A, Fowler S, Krishnan H, Craft J A, Rees Smith B: Steroid 21-hydroxylase is a major autoantigen involved in adult onset autoimmune Addison's disease. *FEBS Lett* 309:51-55, 1992
75. Mullins R J, Cohen S B, Webb L M, Chernajovsky Y, Dayan C M, Londei M, Feldmann M: Identification of thyroid stimulating hormone receptor-specific T cells in Graves' disease thyroid using autoantigen-transfected Epstein-Barr virus-transformed B cell lines. *J Clin Invest* 96:30-37, 1995
76. Kawasaki E, Eisenbarth G S, Wasmeier C, Hutton J C: Autoantibodies to protein tyrosine phosphatase-like proteins in type I diabetes. Overlapping specificities to phogrin and ICA512/IA-2. *Diabetes* 45:1344-1349, 1996
77. Kawasaki E, Yu L, Rewers M J, Hutton J C, Eisenbarth G S: Definition of multiple ICA512/phogrin autoantibody epitopes and detection of intramolecular epitope spreading in relatives of patients with type 1 diabetes. *Diabetes* 47:733-742, 1998
78. Kelemen K, Gottlieb P A, Putnam A L, Davidson H W, Wegmann D R, Hutton J C: HLA-DQ8-associated T cell responses to the diabetes autoantigen phogrin (IA-2 beta) in human prediabetes. *J Immunol* 172:3955-3962, 2004
79. Taneja V, David C S: HLA class II transgenic mice as models of human diseases. *Immunol Rev* 169:67-79, 1999
80. Sonderstrup G, McDevitt H: Identification of autoantigen epitopes in MHC class II transgenic mice. *Immunol Rev* 164:129-138, 1998
81. Inaba T, Koseki H, Suzuki M, Taniguchi M: Double-step and inverse polymerase chain reaction for sensitive detection and cloning of T cell receptor variable region sequences. *Int Immunol* 3:1053-1057, 1991
82. Abraham R S, Wen L, Marietta E V, David C S: Type 1 diabetes-predisposing MHC alleles influence the selection of glutamic acid decarboxylase (GAD) 65-specific T cells in a transgenic model. *J Immunol* 166:1370-1379, 2001
83. Abraham R S, Kudva Y C, Wilson S B, Strominger J L, David C S: Co-expression of HLA DR3 and DQ8 results in the development of spontaneous insulitis and loss of tolerance to GAD65 in transgenic mice. *Diabetes* 49:548-554, 2000
84. Christianson S W, Shultz L D, Leiter E H: Adoptive transfer of diabetes into immunodeficient NOD-scid/scid mice. Relative contributions of CD4+ and CD8+ T-cells from diabetic versus prediabetic NOD.NON-Thy-1a donors. *Diabetes* 42:44-55, 1993
85. Wong F S, Visintin I, Wen L, Flavell R A, Janeway C A, Jr.: CD8 T cell clones from young nonobese diabetic (NOD) islets can transfer rapid onset of diabetes in NOD mice in the absence of CD4 cells. *J Exp Med* 183:67-76, 1996
86. Wang B, Gonzalez A, Benoist C, Mathis D: The role of CD8+ T cells in the initiation of insulin-dependent diabetes mellitus. *Eur J Immunol* 26:1762-1769, 1996
87. Amrani A, Verdaguer J, Anderson B, Utsugi T, Bou S, Santamaria P: Perforin-independent beta-cell destruction by diabetogenic CD8(+) T lymphocytes in transgenic non-obese diabetic mice. *J Clin Invest* 103:1201-1209, 1999

88. Graser R T, DiLorenzo T P, Wang F, Christianson G J, Chapman H D, Roopenian D C, Nathenson S G, Serreze D V: Identification of a CD8 T cell that can independently mediate autoimmune diabetes development in the complete absence of CD4 T cell helper functions. *J Immunol* 164:3913-3918., 2000
89. Haskins K, McDuffie M: Acceleration of diabetes in young NOD mice with a CD4+ islet-specific T cell clone. *Science* 249:1433-1436, 1990
90. Takaki T, Marron M P, Mathews C E, Guttmann S T, Bottino R, Trucco M, DiLorenzo T P, Serreze D V: HLA-A*0201-restricted T cells from humanized NOD mice recognize autoantigens of potential clinical relevance to type 1 diabetes. *J Immunol* 176:3257-3265, 2006

Each publication cited herein is incorporated by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A peptide fragment of the ZnT8 protein comprising an amino acid sequence selected from the group consisting of SEQ ID NOs: 8-24, 40-45, 47-51, and 53-65.

2. The peptide fragment of claim 1, wherein the ZnT8 protein is human ZnT8 (SEQ ID NO:2).

3. A chimeric protein comprising at least one epitope of ZnT8 that is selectively bound by an anti-ZnT8 antibody, comprising, at least two peptide fragments of the ZnT8 protein, wherein each of the at least two peptide fragments has an amino acid sequence selected from the group consisting of SEQ ID NOs: 8-24, 40-45, and 47-51.

4. The chimeric protein of claim 3, wherein the chimeric protein comprises an N-terminal fragment of ZnT8 and a C-terminal fragment of ZnT8.

5. The chimeric protein of claim 3, wherein the chimeric protein comprises an amino acid sequence selected from the group consisting of SEQ ID NOs: 53-65.

6. A method to diagnose an individual who is susceptible to or who is developing Type I diabetes, comprising detecting antibodies that selectively bind to a peptide fragment of ZnT8 in a test sample from the individual, wherein the peptide fragment of ZnT8 comprises an amino acid sequence selected from the group consisting of SEQ ID NOs: 8-24, 40-45, 47-51, and 53-65, and, wherein detection of increased antibodies in the individual as compared to a negative control, indicates that the individual is susceptible to or is developing Type I diabetes.

7. The peptide fragment of claim 1, wherein the peptide fragment has an amino acid sequence selected from the group consisting of SEQ ID NOs: 9, 10, 14-18, 22, 23, and 49.

8. The peptide fragment of claim 1, wherein the peptide fragment has an amino acid sequence selected from the group consisting of SEQ ID NOs: 49-51 and 53-61.

9. The peptide fragment of claim 1, wherein the peptide fragment has an amino acid sequence selected from the group consisting of SEQ ID NOs: 62 and 63.

10. The peptide fragment of claim 1, wherein the peptide fragment has an amino acid sequence selected from the group consisting of SEQ ID NOs: 64 and 65.

11. The peptide fragment of claim 1, wherein the peptide fragment has an amino acid sequence selected from the group consisting of SEQ ID NOs: 53-65.

12. A chimeric protein comprising at least one epitope of ZnT8 that is selectively bound by an anti-ZnT8 antibody, comprising two peptide fragments of ZnT8 linked through a peptide linking sequence;

wherein one of the two peptide fragments comprises the amino acid sequence of SEQ ID NO:14, and, wherein one of the two peptide fragments comprises an amino acid sequence of SEQ ID NO:14 having a tryptophan substitution for the arginine amino acid at position 51 of SEQ ID NO:14.

* * * * *